(12) United States Patent
Janssen et al.

(10) Patent No.: US 11,806,310 B2
(45) Date of Patent: Nov. 7, 2023

(54) SYSTEM FOR DETERMINING GASTRIC MOTILITY AND FOR FEEDING A PATIENT

(71) Applicant: VIPUN Medical NV, Boortmeerbeek (BE)

(72) Inventors: Pieter Janssen, Boortmeerbeek (BE); Peter Annemie Jos Irma Slaets, Kessel-Lo (BE); John Fredy Morales Tellez, Leuven (BE); Jenny Carolina Varon Perez, Heverlee (BE); Steven Vandeput, Kessel-Lo (BE); Sabine Van Huffel, Leuven (BE); Nick Goelen, Leuven (BE); Jan Tack, Leuven (BE)

(73) Assignee: VIPUN Medical NV, Boortmeerbeek (BE)

( * ) Notice: Subject to any disclaimer, the term of this patent is extended or adjusted under 35 U.S.C. 154(b) by 539 days.

(21) Appl. No.: 17/053,547

(22) PCT Filed: May 14, 2019

(86) PCT No.: PCT/EP2019/062369
§ 371 (c)(1),
(2) Date: Nov. 6, 2020

(87) PCT Pub. No.: WO2019/219700
PCT Pub. Date: Nov. 21, 2019

(65) Prior Publication Data
US 2021/0220227 A1    Jul. 22, 2021

(30) Foreign Application Priority Data
May 15, 2018 (EP) .................................... 18172369

(51) Int. Cl.
*A61J 15/00* (2006.01)
*G16H 40/63* (2018.01)
*G16H 20/60* (2018.01)

(52) U.S. Cl.
CPC ....... *A61J 15/0084* (2015.05); *A61J 15/0003* (2013.01); *A61J 15/0049* (2013.01);
(Continued)

(58) Field of Classification Search
CPC ................ A61J 15/0084; A61J 15/0076; A61J 15/0088; A61J 15/0049; A61J 15/0069
See application file for complete search history.

(56) References Cited

U.S. PATENT DOCUMENTS 9,610,227 B2 * 4/2017 Elia .......................... A61M 1/80
10,549,074 B2 * 2/2020 Shaughnessy ........... A61B 5/06
(Continued)

FOREIGN PATENT DOCUMENTS

WO    2009027864 A1    3/2009

OTHER PUBLICATIONS

International Search Report dated Jul. 22, 2019 in reference to co-pending European Patent Application No. PCT/EP2019/062369 filed May 14, 2019.
European Search Report in reference to co-pending European Patent Application No. 18172369.3-1126 filed Nov. 20, 2018.
Janssen, et al., "Intragastric pressure as a determinant of food intake", Neurogastroenterology Motility, vol. 24, pp. 612-e268, 2012.
(Continued)

*Primary Examiner* — Dung T Ulsh
(74) *Attorney, Agent, or Firm* — DINSMORE & SHOHL, LLP

(57) ABSTRACT

A system (100) for artificially feeding a patient, comprising: a pressure sensor (114) fluidly connectable to an inflatable balloon (B) via a first lumen of a balloon catheter (130); a controller (110) operatively connected to the pressure sensor (114) for obtaining the measured pressure values; a food pump (112) fluidly connectable to a second lumen of the balloon catheter having at least one opening (132) for providing food; the controller (110) operatively connected to the food pump (112) for driving the food pump at a configurable flow rate; wherein the controller (110) contains computer executable instructions comprising: first code
(Continued)

fragments for performing a first algorithm (1300) for extracting gastric motility information from the measured pressure values, and second code fragments for performing a second algorithm for dynamically adjusting (708) said flow rate based on said extracted gastric motility information.

20 Claims, 28 Drawing Sheets

(52) U.S. Cl.
CPC ....... *A61J 15/0069* (2013.01); *A61J 15/0073* (2013.01); *A61J 15/0076* (2015.05); *A61J 15/0088* (2015.05); *A61J 15/0092* (2013.01); *G16H 20/60* (2018.01); *G16H 40/63* (2018.01)

(56) References Cited

U.S. PATENT DOCUMENTS

| | | | |
|---|---|---|---|
| 11,406,320 B2* | 8/2022 | Sutaria | A61B 5/0538 |
| 2008/0167607 A1* | 7/2008 | Pfeiffer | A61J 15/0073 |
| | | | 604/99.01 |
| 2009/0062725 A1* | 3/2009 | Goebel | A61B 5/037 |
| | | | 604/28 |

OTHER PUBLICATIONS

Szarka, et al., "Methods for measurement of gastric motility", American Physiological Society, vol. 296, pp. G461-G475, 2009.
Patcharatrakul, et al., Technique of Functional and Motility Test: How to Perform Antroduodenal Manometry, Journal Neurogastroenterol Motil., vol. 19, No. 3, pp. 395-404, Jul. 2013.

* cited by examiner

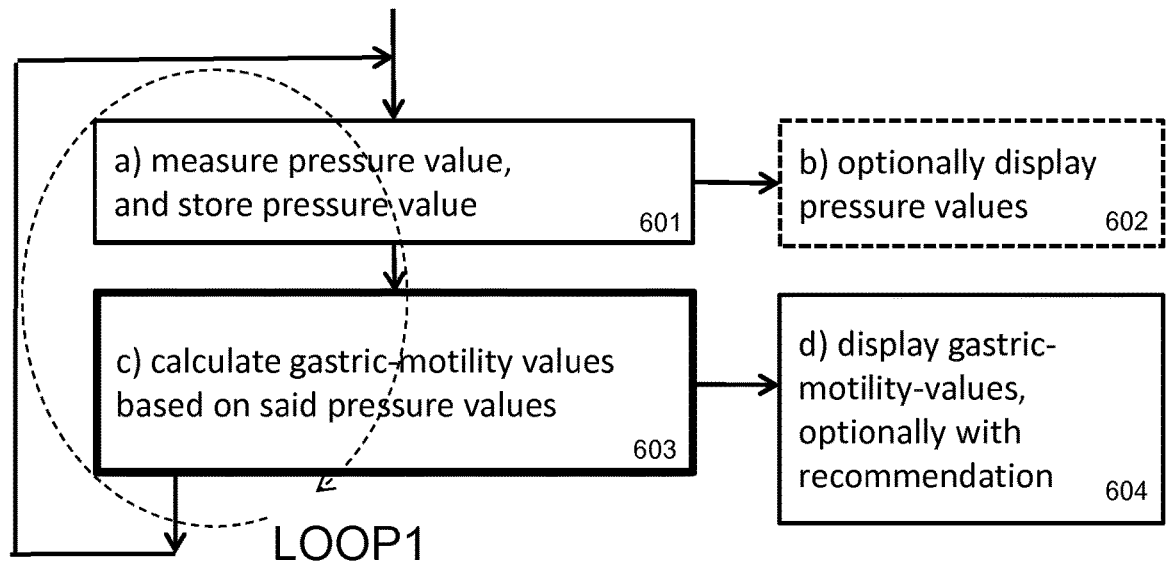
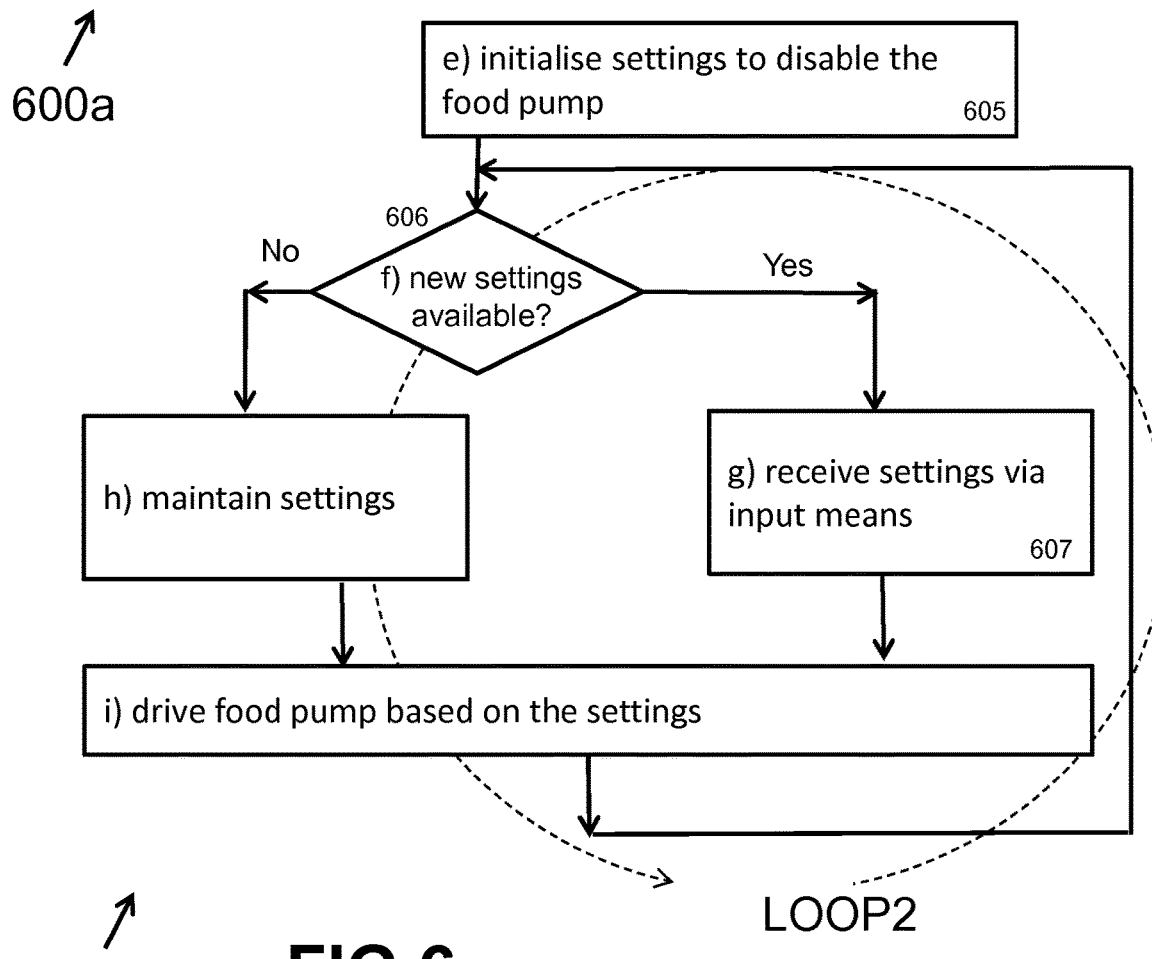
FIG 6

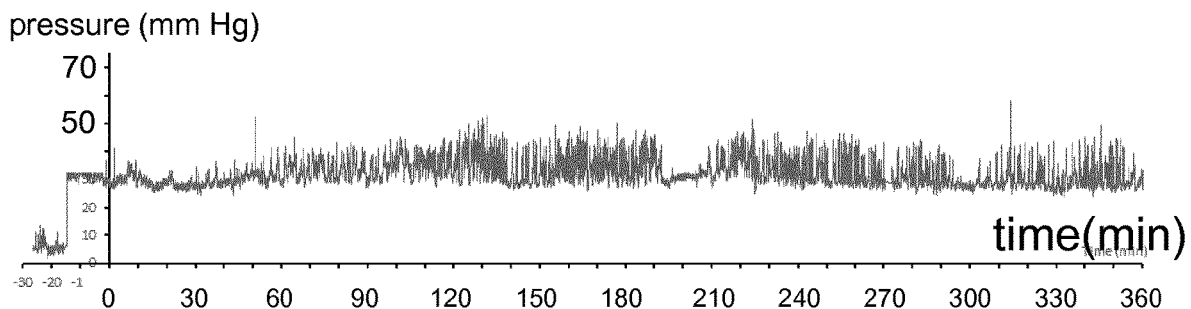
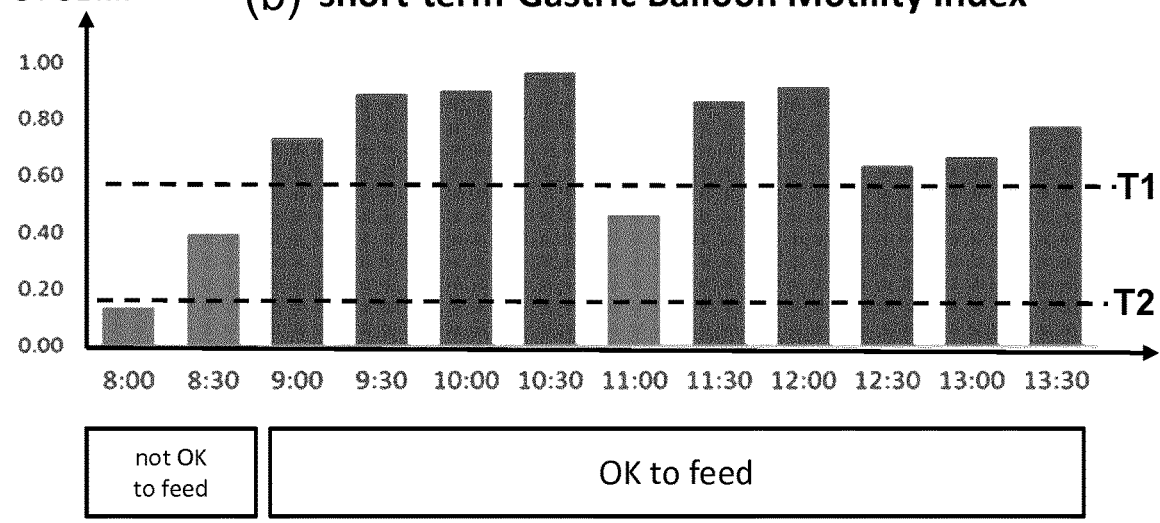
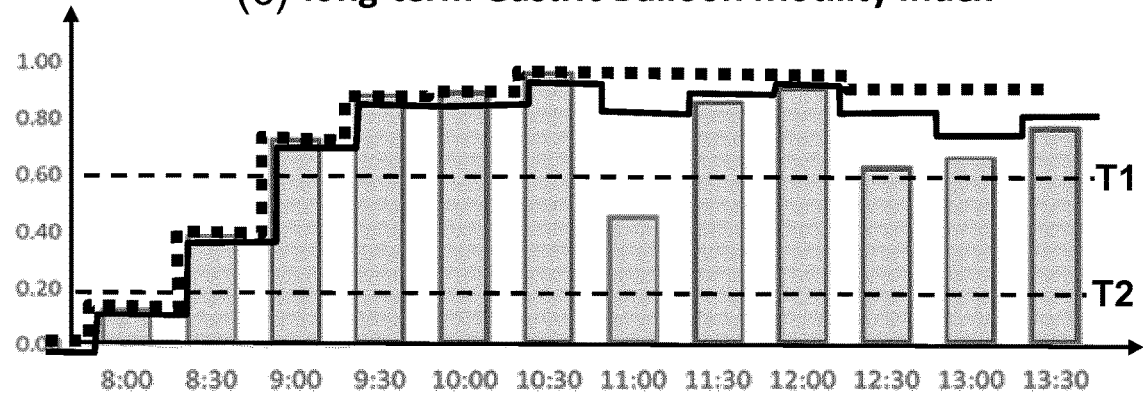
FIG 8

(a) raw Pressure signal
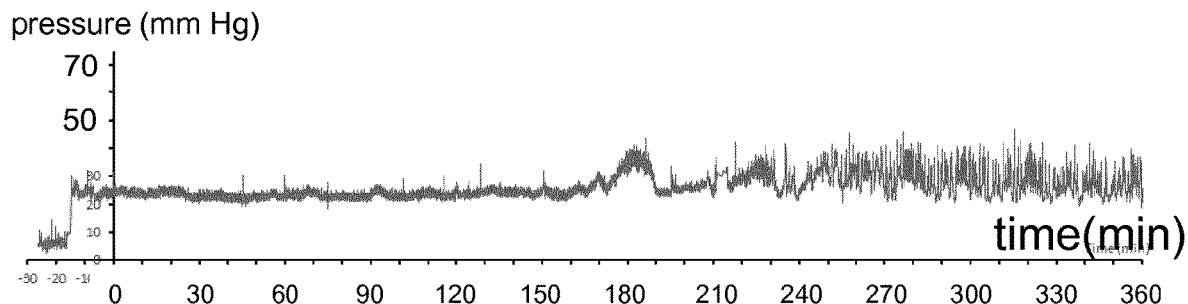
(b) short-term Gastric Balloon Motility Index
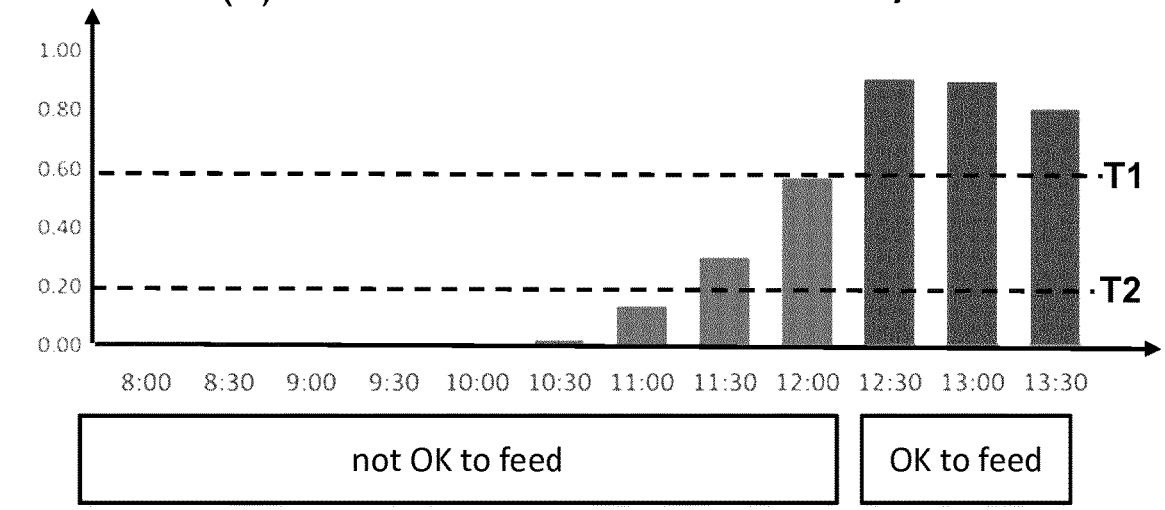
(c) long-term Gastric Balloon Motility Index
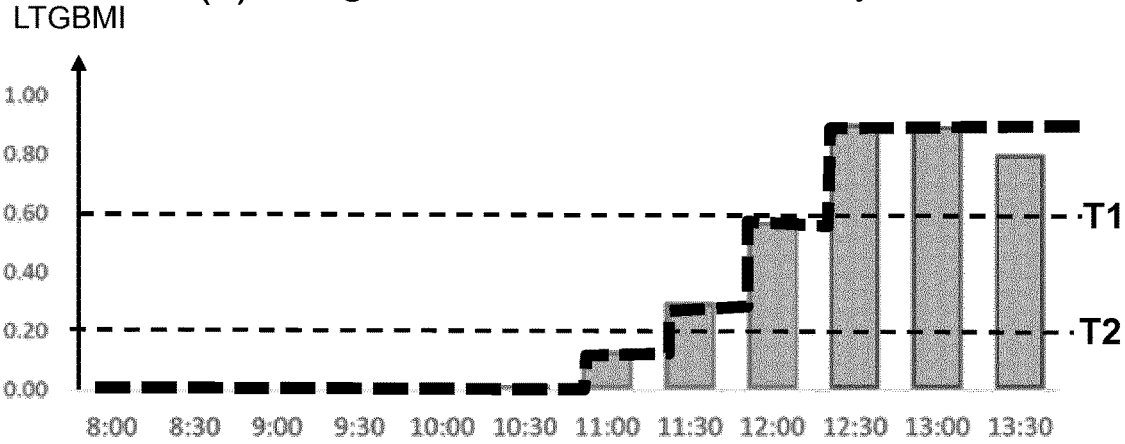
FIG 9

Example of filtering:

- a) removing peaks related to breathing
- b) removing peaks related to coughing, sneezing, hiccup, etc.
- c) low-pass filter (in Freq-domain)

Example of finding Gastric Contraction Peaks:

Example of characteristics for qualifying as valid GCP:

| | |
|---|---|
| "peak height" (H) > Hmin<br>e.g. Hmin=predef constant<br>e.g. Hmin=K*Abr | 1701 |
| "peak duration" (PD) in predefined range | 1702 |
| abs(rising slope) smaller than predefined value | 1703 |
| abs(falling slope) smaller than predefined value | 1704 |
| "peak width at half hight" (PWh) in predefined range, or PWh/PD in predefined range | 1705 |
| distance between two peaks > dmin | 1706 |

FIG 17

In the 20-25 (300 seconds) time window:
- Abr = 0.97 and K= 1.95, hence Hmin=2.1 mmHg
- 5 peaks detected with Hmin>2.1 mmHg
  - Peak 1: GCPD=10 sec, H=2.1 mmHg, GAV1=0.1
  - Peak 2: GCPD=12 sec, H=2.2 mmHg, GAV1=0.24
  - Peak 3: GCPD=13 sec, H=2.7 mmHg, GAV1=0.91
  - Peak 4: GCPD=10 sec, H=3.0 mmHg, GAV1=0.9
  - Peak 5: GCPD=09 sec, H=5.1 mmHg, GAV1=2.52
- STGBMI based on unweighted GCPD=18%
- STGBMI based on weighted GCPD= 1.6%

SYSTEM FOR DETERMINING GASTRIC MOTILITY AND FOR FEEDING A PATIENT

FIELD OF THE INVENTION

The present invention relates in general to the field of systems for determining gastric motility, and more in particular to a system comprising or connectable to a balloon catheter with a balloon which can be inserted (in deflated condition) into the stomach and can then be inflated. The system further comprises a pressure sensor, and a controller adapted with an algorithm for extracting motility information from said pressure values. The motility information can be recorded, and/or visualized, and/or be used in a control loop for adjusting the feeding of the patient. The present invention also relates to a computer program product containing these executable instructions.

BACKGROUND OF THE INVENTION

The stomach is a central organ in gastrointestinal system and a major player in the food processing chain. Impaired motility and emptying are important pathophysiological factors involved in the intolerance of enteral feeding in critically ill patients but also in different gastrointestinal diseases and disorders such as gastroparesis and functional dyspepsia.

Several methods are described in the prior art which can be used for measuring gastric motility. These are reviewed for example in Szarka & Camilleri Am. J. Physiol—Gastrointestinal & Liver Physiol 2009; 296(3): G461-G475.

Tubes for enteral feeding, more in particular for providing nutrients into the stomach, or directly into the duodenum are known in the art, for example as shown in FIG. 24. Such tubes may be entered via the nose of a patient, or via the mouth, and are typically connected to a feeding pump. Such feeding pumps are typically configurable with a desired flow rate, allowing an operator to set a desired volume per time unit to be delivered to a patient.

US2008167607 discloses an enteral feeding catheter for delivering nutrient into a patient's stomach, which may be advanced with its distal tip ahead through the nose or mouth of a patient into the oesophagus and stomach of the patient.

EP2190512 describes a system for preventing gastro-esophageal reflux (GER) by regulating or counterbalancing stomach pressure generated during and in between episodes of gastric-enteral feeding of a patient. The document describes how an esophageal sealing pressure is derived from said stomach pressure for reflux prevention. In addition, the flow rate of the food pump can be adjusted in order to reduce the esophageal sealing pressure.

In the publication "Intragastric pressure as a determinant of food intake: Intragastric pressure determines food intake", NEUROGASTROENTEROLOGY AND MOTILITY, vol. 24, no. 7, 22 Apr. 2012 (2012 Apr. 22), pages 612-e268, XP055522639, GB, ISSN: 1350-1925, DOI: 10.1111/j.1365-2982.2012.01911.x, P. Janssen et al. investigated a correlation between intragastric pressure (IGP) and satiation.

There is always room for alternatives and improvements.

SUMMARY OF THE INVENTION

It is an object of embodiments of the present invention to provide a system for monitoring gastric motility of a patient.

It is an object of embodiments of the present invention to provide a system for monitoring gastric motility of a patient and for recording this gastric motility information.

It is an object of embodiments of the present invention to provide a system for monitoring gastric motility of a patient and for presenting this gastric motility information.

It is an object of embodiments of the present invention to provide a system for monitoring gastric motility of a patient and for using this gastric motility information to automatically or semi-automatically control or adjust the amount of enteral feeding.

It is an object of embodiments of the present invention to provide a system that is easier to use, and/or that provides gastric motility information that is easier to interpret.

It is an object of particular embodiments of the present invention to provide a system that provides gastric motility information that is highly robust (e.g. independent of a person's weight and/or position) and/or highly insensitive to coughing or sneezing.

It is an object of particular embodiments of the present invention to provide a system that provides enteral feeding to a patient in an informed manner and/or in a more sophisticated manner.

It is also an object of embodiments of the present invention to provide a computer program product which can be used in such a system.

These and other objectives are accomplished by a system and a computer program product according to embodiments of the present invention.

According to a first aspect, the present invention provides a system for monitoring gastric motility and for artificially feeding a patient, the system comprising or connectable to a balloon catheter, the balloon catheter comprising an inflatable balloon, and a first lumen in fluid connection with said inflatable balloon, and a second lumen for providing food to the patient, the second lumen having at least one second opening located outside the balloon; the system comprising:—a pressure sensor fluidly connected or connectable to the first lumen for measuring a pressure of a fluid inside said at least one balloon; a food pump fluidly connected or connectable to the second lumen, and adapted for providing food; a controller operatively connected to the pressure sensor for obtaining the measured pressure values, and operatively connected to the food pump for driving the food pump so as to provide food at a configurable flow rate; wherein the controller contains computer executable instructions comprising: first code fragments for performing a first algorithm for extracting gastric motility information from the measured pressure values, and second code fragments for performing a second algorithm for dynamically adjusting the flow rate of the food pump based on said extracted gastric motility information; wherein the first algorithm is adapted for: a) filtering the raw pressure signal to reduce or preferably completely remove influences other than gastric motility-induced pressure changes; b) finding gastric contraction peaks in the filtered pressure signal; c) determining a duration and/or a height of said gastric contraction peaks, and assigning a gastric activity value to each gastric contraction peak indicative of gastric activity based on said duration and/or said height; d) optionally determining a short-term-gastric-motility value (STGBMI) by calculating a sum of a plurality of said gastric activity values normalized over a first time window of 1 to 60 minutes or 2 to 55 minutes, or by calculating a statistical value of a plurality of said gastric activity values over said first time window; e) determining a long-term-gastric-motility-value LTGBMI as a maximum over a second time window of 1 to 3 hours or from 1.5 hours to 3.0 hours of said gastric activity values or as a maximum of said short-term-gastric-motility values; wherein the second algorithm is adapted for: f) comparing the long-term gastric motility value with at least one threshold, and if the LTGBMI-value is lower than said at least one threshold, to reduce the flow-rate or to set the flow-rate to zero, and if the LTGBMI value is higher than said at least one threshold, to maintain or to increase the flow rate.

The present invention provides a system for artificially feeding a person (e.g. a patient who cannot eat autonomously, typically in a hospital, and more in particular in intensive care), whose digestive system may not be working very well, or more in particular, whose stomach may not be working very well.

As far as is known to the inventors, there is no standard system available on the market for measuring "gastric motility". The inventors came to the idea of developing a system with a device for measuring mechanical pressure exerted by the stomach, and an algorithm for extracting or deriving gastric motility information therefrom, and an algorithm for controlling the flow rate of a food pump based on the so determined gastric motility information. In other words, the inventors have developed a system with a control loop for determining whether the stomach is working well, and for influencing the flow rate of the food pump depending thereon.

This combination of features is not trivial inter alia because of the lack of a reliable "gastric motility meter", which led to (1) the development of a specific balloon catheter (see "co-pending application" described further) and led to (2) the development of an algorithm for converting "pressure data" into "gastric motility information", which needs to be highly reliable, especially because this system is primarily intended for people whose stomach is not working very well (e.g. after administration of medicines such as morphine, or after a trauma (e.g. surgery, car accident) etc.)

The combination is also not trivial because the pressure data is preferably sampled at a relatively high rate (e.g. at a frequency of at least 1 Hz, or at least 2 Hz, e.g. equal to about 5 Hz, or equal to about 10 Hz, or equal to about 20 Hz, or equal to about 30 Hz, or equal to about 40 Hz, or equal to about 50 Hz) in order to capture sufficient detail, while gastric activity is much slower (e.g. only about 3 contractions per minute), but "good or bad" functioning of the stomach should be considered over a time span of about 2 hours. That is 4 to 5 orders of magnitude difference.

Typically today, a doctor will decide whether or not a patient is ready to receive food via the stomach, but this decision often needs to be made blindly, because there is no way to (accurately) measure whether the stomach is working well, or working weakly, or not working at all. What typically happens today is that the decision to start feeding a person via the stomach is made based on a subjective assessment of the doctor (e.g. based on bowel sounds or whether the patients makes stool), and once it is decided to start feeding the person artificially, the food pump is started with a very conservative initial flow rate, which is maintained between visits of the doctor, with no flow rate adjustments between these visits, except when things seem to go wrong.

The system of the present invention addresses both problems. First of all, the system is capable of measuring gastric motility, and to optionally present this data to the doctor and other medical personnel in a visible manner, (for example as a 2D graph, allowing the doctor to see variations over time, e.g. over the last 24 or 48 hours), and secondly, the system is capable of automatically adjusting the flow rate of the food pump between doctor visits, depending on good or bad functioning of the stomach. In this way, the flow rate can be reduced automatically if the stomach does not appear to function very well, or can even be stopped automatically. In practice this system will allow the doctor to start with a somewhat less conservative initial flow rate, which will benefit those patients whose stomach is indeed ready to receive the food, and will not negatively influence patients whose stomach is not yet ready, because the system will adjust itself automatically (e.g. by reducing or stopping nutrient flow), long before the next doctor's visit.

Specifically, the solution proposed by the present invention makes use of a balloon catheter with at least one inflatable balloon, which catheter can be introduced in the stomach of the person via the mouth or the nose, which at least one balloon can be inflated (and/or deflated) via a first lumen. The balloon catheter further comprises a second lumen with an opening for supplying nutrients (e.g. liquid food). A more detailed description of such a balloon catheter can be found in "the co-pending balloon-application", published as WO2019030312. It is explicitly pointed out however that the present invention is not limited to embodiments with this particular balloon catheter (which can be introduced via the nose), but may also work with other suitable balloon catheters, provided that they allow to make sufficiently accurate measurements. It is an advantage however if the balloon catheter can indeed be introduced via the nose, because this is much more comfortable for the patient.

It is a major advantage if the system allows to store and/or graphically display gastric motility information over a longer time period (e.g. at least 2 hours, or at least 6 hours, or at least 12 hours, or at least 24 hours, or at least 36 hours, or at least 48 hours). Indeed, unlike blood pressure which can be measured and interpreted instantaneously, gastric motility cannot be measured and interpreted instantaneously, but requires monitoring during a longer period, e.g. in the order of at least two hours, even for a perfectly healthy person. By storing and displaying this information to the doctor, the doctor does not need to make a blind decision, but is accurately and objectively informed based on a continuous measurement over this longer period. In addition, display of such information can also reveal an evolution in a positive or negative way, allowing a doctor to take appropriate action.

It is an advantage if the system of the present invention provides (e.g. displays) "gastric motility information" (which is an interpreted signal) rather than pure pressure data.

It is an advantage that the difficult task of "analysing the pressure data" can be done by a computer, which makes it possible to perform a much more sophisticated and objective analysis, and which reduces the risk of misinterpretation. In fact, it is highly doubtful whether such interpretation can be done by a person at all, especially for the borderline-cases where the stomach is not performing very well, which is what this invention is primarily intended for.

The importance of the present invention should not be underestimated. Providing food to a person via the stomach may considerably decrease the time of recovery of the person, and thus may considerably reduce time spent in a hospital (even 1 day is a considerable improvement), not to speak about the personal benefits to the patient and his or her relatives.

Typical food pumps as can be used in embodiments of the present invention are controlled by providing a certain "volume per time unit" also referred to herein as "flow rate".

It is irrelevant for the present invention whether the food pump provides a continuous stream of nutrient, or multiple discrete amounts.

Experiments have shown that a gastric motility value determined by the first algorithm turns out to have a high correlation with a "good functioning" stomach.

It is an advantage that this algorithm works very well for highly different individuals (e.g. different body weight) and/or different situations (e.g. patients in supine vs. sitting straight). Tests have shown huge differences in the original pressure data (especially in terms of pressure amplitude), but the algorithm is highly robust against such variations.

Many working embodiments are possible, for example as schematically illustrated in FIG. 13d, but considering that the statistical function for example be an average or a median function, and that a variety of functions can be used as the weighting function w(H), and that the duration of the first time window can for example be a value in the range from 1 to 60 minutes, or from 2 to 55 minutes, (e.g. equal to 15 minutes, or 20 minutes, or 25 minutes, or 30 minutes, or 35 minutes, or 40 minutes, or 45 minutes, or 50 minutes or 55 minutes), and that the duration of the second time window can be chosen in the range from 1 to 3 hours (e.g. equal to 1.5 hours=90 minutes, or equal to 2 hours=120 minutes, or equal to 2.5 hours=150 minutes, or equal to 3 hours=180 minutes), many specific implementations are possible. Yet, in all of these embodiments, a "Long Term Gastric Balloon Motility Index" (LTGBMI) is calculated which is indicative of a good working stomach, which is used to control a food pump. Optionally, but not mandatory, the LTGBMI-values are shown on a display. And optionally, but not mandatory, also a short-term-gastric-motility index (STGBMI) can be calculated and/or displayed.

It is an advantage that the algorithm can provide both a short term (e.g. average or mean) gastric motility value and a long term gastric motility value. While control of the food pump is based solely on the "long term gastric motility value", and the "short term gastric motility value" could be hidden from the medical personnel, both the short term and long term gastric motility value reveal interesting information, which is highly intuitive to understand, and both have their merits and are interesting for medical personnel looking at the medical status (e.g. stable, improving, worsening, recovering fast/slow, etc.) beyond mere feeding.

Or stated in other words, it is an advantage that some medical personnel (e.g. people only responsible for feeding), can simply ignore the short term gastric motility value, and can simply rely on the long term gastric motility value, which makes life easy, and reduces the risk of human errors considerably; while other medical personnel (e.g. doctors responsible for deciding whether or not to start feeding and at which initial flow rate) can "see" if there was any gastric activity.

It is an advantage of the present invention that the algorithm does not make a difference between Migrating Motor Complex (MMC) phase II-peaks and MMC phase-III peaks for determining the short term gastric motility value, but variations are possible where for example an MMC phase III peak by itself, or an MMC phase III peak followed by an MMC phase I (no or few contractile events) is assigned a higher weight.

In an embodiment, the long term gastric motility value, and if used, preferably also the short-term gastric motility value, is periodically updated, e.g. once every 5 minutes, or once every 10 minutes, or once every 15 minutes.

In an embodiment, step c) comprises determining a duration GCPD for each of said gastric contraction peaks, and assigning a value equal to said duration GCPD as the gastric activity value GAV, e.g. according to the formula GAV=GCPD; and step d) comprises determining short-term-gastric-motility values STGBMI by calculating a sum of a plurality of said gastric activity values normalized over said first time window, e.g. according to the formula: STGBMI=$\Sigma_{TW1}$(GCPD)/TW1); and step e) comprises determining said long-term-gastric-motility-value LTGBMI as a maximum of said short-term-gastric-motility-values, e.g. according to the formula: LTGBMI=$\max_{TW2}$(STGBMI). This embodiment is illustrated in branch (i) of FIG. 13d, and in FIG. 13a.

In an embodiment, step c) comprises determining a height H for each of said gastric contraction peaks, and assigning a value in the range from 0.0 to 1.0 as a weight function of said height w(H) as the gastric activity value GAV, e.g. according to the formula GAV=w(H); and optional step d) comprises: determining a short-term-gastric-motility value STGBMI by calculating a statistical value (e.g. a mean or a median value) of a plurality of said gastric activity values GAV over said first time window, e.g. according to the formula: STGBMI=AVERAGE$_{TW1}$(GAV), or STGBMI=MEDIAN$_{TW1}$(GAV); and step e) comprises determining said long-term-gastric-motility-value LTGBMI as a maximum of said gastric activity values GAV, e.g. according to the formula: LTGBMI=$\max_{TW2}$(GAV). This embodiment is illustrated in branch (ii) (with the optional horizontal arrow) of FIG. 13d, and in branch (ii) of FIG. 13b.

In an embodiment, step c) comprises determining a height H for each of said gastric contraction peaks, and assigning a value in the range from 0.0 to 1.0 as a weight function of said height w(H) as the gastric activity value GAV, e.g. according to the formula GAV=w(H); and step d) comprises: determining a short-term-gastric-motility value STGBMI by calculating a statistical value of a plurality of said gastric activity values over said first time window, e.g. according to the formula: STGBMI=AVERAGE$_{TW1}$(GAV), or STGBMI=MEDIAN$_{TW1}$(GAV); and step e) comprises determining said long-term-gastric-motility-value LTGBMI as a maximum of said short-term-gastric-motility values, e.g. according to the formula: LTGBMI=$\max_{TW2}$(STGBMI). This embodiment is illustrated in branch (iii) of FIG. 13d, and in branch (iii) of FIG. 13b.

In an embodiment, step c) comprises determining a duration GCPD and a height H for each of said gastric contraction peaks, and assigning a fraction of said duration using a weight function of said height w(H) as the gastric activity value GAV, e.g. according to the formula: GAV=GCPD*w(H); and step d) comprises determining short-term-gastric-motility values STGBMI by calculating a sum of a plurality of said gastric activity values GAV normalized over said first time window, e.g. according to the formula STGBMI=$\Sigma_{TW1}$(GAV)/TW1; and step e) comprises determining said long-term-gastric-motility-value LTGBMI as a maximum of said short-term-gastric-motility values, e.g. according to the formula: LTGBMI=$\max_{TW2}$(STGBMI).

These are four specific embodiments where either the duration but not the height of gastric contraction peaks are taken into account, or either the height but not the duration, or both the height and the duration. These are four ways to express a "strong gastric contraction peak". It is noted that the GAV of branch (i) and (iv) have a time dimension, whereas the GAV calculated in branch (ii) and (iii) are dimensionless. It is noted that the LTGBMI-values and the optional STGBMI-values are dimensionless. This is achieved by the normalization (e.g. division by the duration of the first time window) in step d) of branch (i) and branch (iv).

If the peak height is taken into account, then preferably a weighting factor or a fraction value is derived from said height, which weighting factor or fraction is used as a percentage value per se (e.g. as in branch ii of FIG. 13d), or is multiplied by the peak duration (e.g. as in branch iii and iv of FIG. 13d). The weighting function is preferably chosen such that relatively strong peaks are given a larger weight (or fraction) than relatively weak peaks. If the peak is too small, it is ignored (fraction=0). If the peak is very strong, it is given maximum weight (fraction=1). Several monotonically increasing functions can be used (see e.g. FIG. 13e and FIG. 13f). These functions need not be continuous (e.g. a staircase function also works), and "strictly monotonic increasing functions" are not required.

It is an advantage of embodiments using a combination of peak height and peak duration that stronger gastric peaks (having a larger height) can be assigned a larger value than weaker gastric peaks (having a smaller height), even if they have the same duration.

In preferred embodiments, the relatively weak pressure value is a value in the range from 100 to 700 Pa, or in the range from 200 to 600 Pa, for example equal to about 400 Pa.

In preferred embodiments, the relatively strong pressure value is a value in the range from 1000 to 3000 Pa, or in the range from 1300 to 2500 Pa, or in the range from 1750 to 2500 Pa, for example equal to about 1750 Pa or about 2000 Pa or about 2250 Pa.

It is noted that branch (i) can be regarded as a special case of branch (iv) wherein the relatively weak predefined pressure is equal to the relatively strong predefined pressure, and wherein the weight factor is either 0 (if the peak height is lower than said predefined pressure) or 1 (if the peak height is larger than said predefined pressure). It is an advantage of the implementation of branch (ii) that it is relatively simple, yet provides very good results. It is an advantage of the implementation of branch (iv) that the calculations are somewhat more complicated, but weaker peaks contribute less to the short-term and long-term motility index.

In an embodiment, the weight function (or fraction) is a monotonically increasing function of the height, the function being equal to 0.0 if the height is smaller than a first predefined pressure value (e.g. the above mentioned relatively weak pressure value); and equal to 1.0 if the height is larger than a second predefined pressure value (e.g. the above mentioned relatively strong pressure value).

Such a weight function codifies that very small gastric peaks are insignificant, and that peaks having a height equal to or larger than the second predefined pressure value are fully taken into account. If the height lies between the first and second threshold, the peak is partially taken into account. If the height lies above the second threshold, the peak is fully taken into account, but not more than other peaks having a height above the second threshold. Experiments have shown that such a weight function provides an even better correlation with good/bad functioning of the stomach.

In an embodiment, the weight function linearly increases from 0.0 to 1.0 for height values between the first and second predefined pressure value.

In an embodiment, the weight function is a staircase function having at least one level between 0.0 and 1.0 for height values between the first and second predefined pressure value.

In an embodiment, the weight function is a first order or second order or third order polynomial function for height values between the first and second predefined pressure value.

In an embodiment, the statistical value of step d) is selected from the group consisting of: an average or mean value, and a median value.

In an embodiment, step a) comprises: filtering the raw pressure signal to reduce or preferably completely removing pressure changes related to one or more of the following: breathing, heart beats, gagging, coughing, sneezing, hiccups.

In an embodiment, step a) comprises: reducing or preferably completely removing pressure changes related to breathing.

In an embodiment, step b) comprises: b1) finding start points and stop points of candidate gastric contraction peaks; b2) determining at least one characteristic of the waveform of each candidate gastric contraction peak; b3) testing whether said at least one characteristic satisfies a predetermined condition; and if an outcome of this test is true, considering this candidate gastric contraction peak as a valid gastric contraction peak or considering this candidate gastric contraction peak as a preliminary gastric contraction peak; and if the outcome of the test is false, discarding this candidate gastric contraction peak by not taking its duration and/or its height into account in the calculation of the gastric activity value, the optional short-term-gastric-motility value, and the long-term gastric motility value.

It is an advantage that this algorithm simplifies the analysis by first searching individual candidate peaks, and then deciding which of these peaks are considered to be real gastric contraction peaks.

Two versions of step b3) are envisioned: a first one (see FIG. 15) where no post-processing is performed on the so found gastric contraction peaks, a second one (see FIG. 16) where post-processing is performed on the so found preliminary gastric contraction peaks.

In an embodiment step b1) comprises: finding local minima of the filtered pressure signal, and considering each waveform between consecutive local minima as a candidate gastric contraction peak; and step c) comprises: considering the time between these minima as the peak duration; and step b2) comprises: finding a minimum pressure and finding a maximum pressure of the candidate gastric contraction peak between the local minima, and considering a difference between the maximum pressure and the minimum pressure as the height of the candidate gastric contraction peak; and step b3) comprises: testing whether said height of the candidate gastric contraction peak is larger than a given height value (e.g. the above mentioned relatively weak pressure value Hmin) and testing whether said peak duration is a value in a predefined range, for example in the range from 3 to 80 seconds, or in the range from 5 to 80 seconds, or in the range from 10 to 80 seconds, or in the range from 3 to 50 seconds, or in the range from 5 to 50 seconds, or in the range from 10 to 50 seconds.

This is a first specific embodiment to find "gastric contraction peaks", but other ways are possible.

In an embodiment, step b1) comprises: finding a start point at a crossing of a rising edge of the filtered pressure signal and a given height value, and finding a stop point at a crossing of a falling edge of the filtered pressure signal and the given height value, and considering each waveform between said start point and said stop point as a candidate gastric contraction peak, and considering the time between the start point and the stop point as the peak duration; and step b2) comprises: finding a minimum pressure and finding a maximum pressure of the candidate gastric contraction peak between the start point and the stop point, and considering a difference between the maximum pressure and the minimum pressure as the height of the candidate gastric contraction peak; and step b3) comprises: testing whether said peak duration is a value in a predefined range, for example in the range from 3 to 80 seconds, or in the range from 5 to 80 seconds, or in the range from 10 to 80 seconds, or in the range from 3 to 50 seconds, or in the range from 5 to 50 seconds, or in the range from 10 to 50 seconds.

This is a second specific embodiment to find "gastric contraction peaks", but other ways are possible.

As is well known, the rising edge of a signal can be found by testing whether the first derivative of the signal is positive, or by testing whether the signal is increasing.

As is well known, the falling edge of a signal can be found by testing whether the first derivative of the signal is negative, or by testing whether the signal is decreasing.

In an embodiment, step b3) comprises: testing whether said at least one characteristic satisfies a predetermined condition or set of predetermined conditions, and if an outcome of this test is true, considering this candidate gastric contraction peak as a preliminary gastric contraction peak; and the algorithm further comprises step b4) of testing whether recently considered preliminary gastric contraction peaks satisfy a predetermined condition or set of predetermined conditions, and if an outcome of this test is true, to consider at least some of the recently considered preliminary gastric contraction peaks as real or valid gastric contraction peaks, and if the outcome of this test is false, to consider at least one of the recently considered preliminary gastric contraction peaks as invalid.

This optional post-processing step allows to perform additional tests on peaks which initially (when considered alone) seemed to satisfy the criterion/criteria to qualify as a gastric contraction peak, but which, on second consideration, when considering a plurality of at least two or at least three such peaks, or when considering peaks in a recent time window of for example about 1 to 5 minutes, are considered to be invalid gastric contraction peaks after all, or in other words, they are not considered as gastric compression motility peaks that are to be taken into account for the calculation of the gastric-motility-values after all.

In an embodiment, step b2) further comprises: determining a first slope as the maximum slope of the rising edge of the candidate gastric peak; and step b3) further comprises: testing whether said first slope is smaller or larger than a predefined value, and if the first slope is larger than the predefined value, discarding the candidate gastric contraction peak. This actually means: testing whether the steepness of the rising edge is not too high.

In an embodiment, step b2) further comprises: determining a second slope as the minimum slope (negative value, largest absolute value) of the falling edge of the candidate gastric contraction peak; and step b3) further comprises: testing whether an absolute value of the second slope is smaller or larger than a predefined value, and if the absolute value of the second slope is larger than the predefined value, discarding the candidate gastric contraction peak. This actually means: testing whether the steepness of the falling edge is not too high.

In an embodiment, the given (minimum) height value (to qualify as a valid gastric contraction peak) is a fixed, predetermined value. This value may for example be hard-coded. This value may be a value in the range from 0.01 psi (about 0.07 kPa) to 1.0 psi (about 6.9 kPa), or from 0.02 psi (about 0.14 kPa) to 0.5 psi (about 3.45 kPa), or from 0.02 psi (about 0.14 kPa) to 0.3 psi (about 2.07 kPa), or from 0.02 psi (about 0.14 kPa) to 0.2 psi (about 1.38 kPa), for example equal to about 0.05 kPa, or about 0.075 kPa, or about 0.10 kPa, or about 0.15 kPa, or about 0.20 kPa, or about 0.25 kPa, or about 0.30 kPa, or about 0.35 kPa, or about 0.40 kPa, or about 0.45 kPa, or about 0.50 kPa, or about 0.55 kPa, or about 0.60 kPa, or about 0.65 kPa, or about 0.70 kPa, or about 0.75 kPa, or about 0.80 kPa, or about 0.85 kPa, or about 0.90 kPa, or about 0.95 kPa, or about 1.0 kPa, or about 1.05 kPa, or about 1.1 kPa, or about 1.15 kPa, or about 1.2 kPa, or about 1.25 kPa, or about 1.3 kPa, or about 1.35 kPa.

It is an advantage that comparing the peak heights with a predetermined value is easy to implement, but tests have shown that determining the ideal value is not an easy task, and the ideal value may not provide the best results given variation in the circumstances of the measurements.

In another embodiment, the predefined height value is a value which is input into the system, or derived from another value input into the system (e.g. based on the weight or estimated weight of the person), for example via a look-up table.

In an embodiment, the first algorithm further comprises a step of determining a pressure amplitude "Abr" related to breathing; and wherein the given (minimum) height value Hmin (to qualify as a valid gastric contraction peak) is dynamically calculated as a function of said pressure amplitude "Abr" related to breathing.

This amplitude is also referred to herein as the "breathing amplitude".

It is an advantage of embodiments where the given height value "Hmin" is automatically determined (because this reduces the risk of human error when entering a value manually), and because it allows to automatically assign an appropriate value to each particular person (e.g. a light-weight person versus a heavy person), and because it may even automatically adjust itself depending on a physical position of the person (e.g. lying on the back/the side, with stretched legs or pulled-up legs, etc).

In other words, it is an advantage that this embodiment automatically adjusts the minimum gastric peak height for each individual situation.

In an embodiment, the given height value is chosen as proportional to the breathing amplitude Abr, using a multi-plication factor K, according to the formula (or an equivalent formula): Hmin=K*Abr, where K is a value in the range from 0.5 to 5.0.

The "breathing amplitude" and "given height value" are preferably calculated repeatedly, for example every 5 minutes or every 10 minutes or every 15 minutes. In this way, recent changes in the situation of the measurement (e.g. movements of the person) are taken into account.

In an embodiment, the pressure amplitude related to breathing is determined using a lower envelope to determine a base line (or rather base curve), and using a median function to remove outliers.

In an embodiment, the controller comprises: a first computing device for interfacing with the at least one pressure sensor and with the at least one food pump; and a second computing device for performing at least the first algorithm for extracting the gastric motility information, e.g. in the form of a short-term and/or a long-term gastric balloon motility index.

It is an advantage of this embodiment that the extraction of the gastric motility information can be off-loaded to a second computing device, which may comprise or may be a generic computing device provided with a dedicated software program such as e.g. a personal computer, a desktop computer, a laptop computer, or a Digital Signal Processor (DSP), or may be a dedicated hardware device, such as a Field Programmable Gate Array (FPGA) or even an Application Specific Integrated Circuit (ASIC). Such a second computer can have more resources in terms of processing power, memory resources, storage capacity, libraries of mathematical functions, support for floating point numbers, etc. as compared to a simple 8-bit or 16-bit microcontroller, for example.

It is an advantage that, in such a configuration, the first computing device only needs to perform relatively basic functions, such as periodic readout of the pressure sensor, transmitting said pressure data to the second computing device, receiving gastric motility information and/or receiving flow rate information from the second computer device, and driving the food pump. Such functionality can readily be implemented in a simple microcontroller.

In an embodiment, the system further comprises: output means for displaying at least the long-term gastric motility information and/or values derived herefrom (e.g. the LTGBMI multiplied by a predefined factor and limited to 100%), and optionally also said short-term gastric motility values and/or values derived herefrom (e.g. the STGBMI multiplied by a predefined factor and limited to 100%); and wherein the computer executable instructions further comprise third code fragments for presenting said gastric motility information on said output means, for example as graphical objects.

The output means may comprise for example a display device, such as an LCD display device, or a LED bar with for example 3 LEDs (e.g. green, orange or yellow, and red), or for example 5 to 10 LEDs, or a numerical display with one or more 7-segment characters, or a graphical display, or any other suitable display.

It is an advantage of showing the gastric motility information, e.g. in the form of a graphical curve over time, because it allows medical personnel, e.g. a doctor, to "see" how the stomach is functioning. This allows the doctor to take an informed decision about when to start supplying food to the patient via the balloon catheter, and at which initial flow rate. This also allows, once started, to follow-up the stomach function, allowing the medical personnel and/or the system to adjust the flow-rate, if needed.

In an embodiment, the system further comprises input means for receiving settings and/or commands to drive the food pump; and the computer executable instructions further comprise fourth code fragments for receiving said settings and/or commands from the input means.

Preferably the device can accept new settings at any time, allowing the doctor to change the flow rate, or to stop the feeding at any time.

It is an advantage of a system according to the present invention that, between such moments at which a doctor provides new settings, the system can autonomously and dynamically adjust the settings depending on the stomach function. Medical personnel can overrule these settings at any time.

In preferred embodiments, the system is provided with a means to enable or disable this "automatic pilot". When disabled, the system simply drives the food pump with the settings input by the medical personnel, and maintains these settings (as illustrated in FIG. 6). When enabled, the system starts with the settings provided by the medical personnel, but can gradually change the flow rate, depending on the behaviour of the stomach, as derived from the pressure data.

In an embodiment, step e) of the second algorithm comprises: testing whether the long-term gastric motility value LTGBMI is larger than or optionally equal to a predefined threshold value; and if an outcome of this test is true, maintaining the current flow rate; and if an outcome of this test is false, reducing the current flow rate.

It is an advantage of this embodiment (shown in FIG. 10) that the second algorithm uses only a single threshold value which is extremely simple.

It is an advantage of this embodiment that the second algorithm cannot increase the flow rate (which might be dangerous for the patient), but can only maintain or reduce the flow rate, which is always safe for the patient. It is possible to stop the food supply also in this embodiment, but it may take a few iterations.

The flow rate is typically adjusted every 30 minutes, and is maintained in between. Thus one iteration typically last for about 30 minutes, but the invention would also work with other periods, for example any period in the range from 15 minutes to 24 hours, or in the range from 15 minutes to 12 hours, for example every 20 minutes, or every 30 minutes, or every hour, or every 2 hours or every 3 hours, or every 4 hours, or every 6 hours, or every 12 hours.

In an embodiment, step e) of the second algorithm comprises: testing in a first test whether the long-term gastric motility value LTGBMI is larger than or optionally equal to a first predefined threshold value "T1"; and if an outcome of this first test is true, maintaining the current flow rate, and if an outcome of this first test is false, to continue as follows: testing in a second test whether the long-term gastric motility value LTGBMI is larger than or optionally equal to a second predefined threshold value "T2"; and if an outcome of this second test is true, reducing the current flow rate; and if an outcome of this second test is false, setting the flow rate to zero, or in other words, stopping the food pump.

It is an advantage of this embodiment that the second algorithm uses only two threshold values, which is still easy to implement, but can provide more sophisticated control, in that it allows to differentiate between gradually reducing the flow rate, or immediately stopping the food supply, if needed.

In an embodiment, step e) of the second algorithm comprises: testing in a first test whether the long-term gastric motility value LTGBMI is larger than or optionally equal to a first predefined threshold value; and if an outcome of this first test is true, increasing the current flow rate; and if an outcome of this first test is false, to continue as follows: testing in a second test whether the long-term gastric motility value LTGBMI is larger than or optionally equal to a second predefined threshold value; and if an outcome of this second test is true, maintaining the current flow rate; and if an outcome of this second test is false, to continue as follows: testing in a third test whether the long-term gastric motility value LTGBMI is larger than or optionally equal to a third predefined threshold value; and if an outcome of this third test is true, reducing the current flow rate; and if an outcome of this third test is false, setting the flow rate to zero, or in other words, stopping the food pump.

It is an advantage of this embodiment that the second algorithm uses three threshold values, and can provide even more sophisticated control, in that it allows to automatically increase the flow rate. It is pointed out that, although in theory there might be a potential risk in automatically increasing the flow rate, this risk should be put in perspective, firstly because the device cannot enable "automatic pilot" by itself, hence a doctor (or other medical personnel) considered it safe that if all the readings are well, that the flow rate is allowed to increase, the risk is minimal, and secondly, in that the flow rate is limited to a predetermined value (e.g. at most 250 ml per hour), and also the flow rate increase can be limited.

In an embodiment, the system further comprises a first port P1 connected or connectable to the first lumen of the balloon catheter, and the pressure sensor is fluidly connected or connectable to the first port, and the system further comprises a second port P2 connected or connectable to the second lumen, and the food pomp is fluidly connected or connectable to the second port P2.

The inflatable balloon is typically adapted to be positioned in a stomach of the patient. The first lumen typically has at least one first opening located inside the balloon, for allowing the balloon to be inflated and deflated.

In an embodiment, the system further comprises an air pump fluidly connected or connectable to the first port; and the controller is operatively connected to said air pump, and is further adapted for driving the air pump for inflating the at least one balloon and/or for deflating the balloon.

It is an advantage of this embodiment that the balloon of the balloon catheter can also automatically or semi-automatically be inflated by the system.

It is an advantage that the pressure may be measured while supplying air to the first port (and thus to the balloon), because this may allow to detect anomalies.

In an embodiment, the balloon catheter further comprises a second balloon fluidly connected to a third lumen having at least a third opening located inside the second balloon, the second balloon being separately inflatable from the first balloon, and being located at a distal position of the balloon catheter; and the system further comprises a third port connectable to the third lumen of the balloon catheter, and further comprises a second pressure sensor fluidly connectable to the third port for measuring a pressure of a fluid inside the second balloon; and the controller is operatively connected to the second pressure sensor and further adapted for obtaining the measured pressure values related to the second balloon; and wherein the first algorithm is further adapted for determining a direction of the gastric contractions as being towards or away from the small intestine; and wherein the flow rate is set at zero in the second algorithm if the determined direction of the gastric contractions is away from the small intestine.

It is an advantage of this embodiment that the system can detect the direction of the gastric contractions, for example towards the esophagus (which is a bad sign) or towards the small intestine (which is a good sign).

Gastric contractions towards the esophagus can for example be detected by comparing the locations (in time) of the gastric contraction peaks of the first pressure signal related to the pressure in the first balloon which is located closer to the esophagus), with the locations (in time) of the gastric contraction peaks of the second pressure signal related to the pressure in the second balloon which is located further away from the esophagus. If corresponding peaks occur first in the first pressure signal, and later in the second pressure signal, then movement is towards the small intestine (which is good). If corresponding peaks occur first in the second pressure signal, and later in the first pressure signal, then movement is toward the esophagus (which is bad).

It is pointed out that the determination of the "contraction direction" may be determined based on a correlation of the first and second pressure data, or on a correlation of the locations of the individual peaks detected in the first and second pressure signal, or on a correlation of (first) short-term gastric motility values related to the first balloon and (second) short term gastric motility values related to the second balloon, or in other suitable ways.

In an embodiment, the size or the "target volume" of the first balloon and the size or "target volume" of the second balloon are substantially the same. For example Target Volume1=Target Volume2*F, where f is a value in the range from 90% to 110%.

In an embodiment, the size or "target volume" of the first balloon is larger than that of the second balloon. For example Target Volume1=Target Volume2*F, where f is a value in the range from 110% to 200%.

In an embodiment, the size or "target volume" of the first balloon is smaller than that of the second balloon. For example, Target Volume1=Target Volume2*F, where f is a value in the range from 50% to 90%.

In an embodiment, the first algorithm is performed separately for each of the first and second balloon pressure signal, thus yielding first and second LTGBMI-values. The food pump may be controlled based on either the first LTGBMI-values, or based on the second LTGBMI-values, or based on an average of the first and second LTGBMI-values.

Normally the first and second balloon should provide more or less the same values, except for a small time-shift in the order of 1 to 20 seconds.

It is an advantage of this system that it cannot only determine the direction of the stomach contractions (towards or away from the esophagus), but also provides (under normal circumstances) redundant information. This may reveal further medical problems.

In an embodiment, the balloon catheter further comprises a fourth lumen having at least a fourth opening located at a distal end of the balloon catheter outside the first balloon and if present also outside the second balloon, for providing food directly into a small intestine; and the system further comprises a fourth port connected or connectable to the fourth lumen of the balloon catheter; and wherein the system further comprises at least one valve operatively connected between the food pump and the second port and the fourth port for selectively providing food into the stomach via the second port or into the small intestine via the fourth port; and the second algorithm is further adapted for dynamically adjusting a position of said valve, for providing food via the fourth port if the long term gastric motility information is lower than a predefined threshold, and for maintaining the position of the valve, otherwise.

It is an advantage of this system that it can supply food either directly into the small intestine (e.g. if the stomach is not working well), or into the stomach (e.g. if the stomach is working well).

It is envisioned that the system, once started by a doctor, can automatically adjust the flow rate and/or the location of delivery (stomach or small intestine) between doctors visits, based on the LTGBMI.

In an embodiment, the system can decide to switch from feeding in the stomach to feeding directly into the small intestine, e.g. if the LTGBMI is not so good (read: is smaller than a predefined value, e.g. smaller than T in FIG. 10, or smaller than T1 but larger than T2 in FIG. 11, or smaller than T2 but larger than T3 in FIG. 12). This action is considered to be safe.

In some embodiments, the system may also decide to switch from feeding directly into the small intestine to feeding into the stomach, e.g. if the LTGBMI is very good (read: is higher than T1 in FIG. 12). Preferably the system is provided with a switch or a setting to enable or disable this functionality. The idea is that a doctor can decide at some point in time to either manually switch to feeding the patient into the stomach, or allow the system to automatically switch when the LTGBMI is sufficiently high.

In an embodiment, the system further comprises the balloon catheter.

In particular embodiments, the balloon catheter is one of the balloon catheters described in the co-pending balloon application.

In an embodiment, the system further comprises: a memory and/or a storage device operatively connected to said controller; and the controller further contains fifth code fragments for storing one or more of the following: the raw pressure values, the location and/or duration and/or height of the gastric contraction peaks, the amplitude of the breathing signal, the gastric activity values GAV, the short-term gastric motility values STGBMI, and the long-term gastric motility values (LTGBMI), in said memory and/or in said storage device.

According to a second aspect, the present invention also provides a computer program product as can be used in a system according to the first aspect, the computer program product comprising at least said first code fragments and said second code fragments, and optionally one or more of said third code fragments, said fourth code fragments and said fifth code fragments.

Preferably the computer program product contains each of the first, second, third, fourth and fifth code fragments.

According to a third aspect, the present invention also provides a system for monitoring and displaying gastric motility information of a patient, the system comprising or connectable to a balloon catheter; the balloon catheter comprising an inflatable balloon, and a first lumen in fluid connection with said inflatable balloon, and a second lumen for providing food to the patient, the second lumen having at least one second opening located outside the balloon; the system comprising: a pressure sensor fluidly connected or connectable to the first lumen for measuring a pressure of a fluid inside said at least one balloon; a controller operatively connected to the pressure sensor for obtaining the measured pressure values; output means operatively connected to the controller for displaying the extracted gastric motility information; input means operatively connected to the controller for receiving settings and/or commands to drive the food pump; wherein the controller contains computer executable instructions comprising: first code fragments for performing the first algorithm described above, and third code fragments for presenting one or both of the long-term gastric motility information and the short-term-gastric-motility information on said output means; and fourth code fragments for receiving said settings and/or commands from the input means.

Various embodiments are envisioned, for example variants of the embodiments described above without any food pump. But also variants of the embodiments described above, including the one or more food pumps, but without the second algorithm. Instead, the controller accepts input from an operator, and drives the one or more food pumps based on said input, without adjusting that input.

Besides the gastric motility information, also information related to heart beat, respiration, coughing, status of the food pump (if present), recommendation(s) regarding feeding the patient, etc. may be displayed.

In an embodiment, the system further comprises a first port P1 connected or connectable to the first lumen of the balloon catheter, and the pressure sensor is fluidly connected or connectable to the first port, and the system further comprises a second port P2 connected or connectable to the second lumen, and the food pomp is fluidly connected or connectable to the second port P2.

The inflatable balloon is typically adapted to be positioned in a stomach of the patient. The first lumen typically has at least one first opening located inside the balloon, for allowing the balloon to be inflated and deflated.

In an embodiment, the system further comprises: a memory and/or a storage device operatively connected to said controller; and the controller further contains fifth code fragments for storing one or more of the following: the raw pressure values, the location and/or duration and/or height of the gastric contraction peaks, the amplitude of the breathing signal, the gastric activity values GAV, the short-term motility values STGBMI, and the long-term gastric motility values LTGBMI, in said memory and/or in said storage device.

According to a fourth aspect, the present invention also provides a computer program product as can be used in a system according to the third aspect, the computer program product comprising at least said first code fragments and said third code fragments and said fourth code fragments, and optionally also said fifth code fragments.

Particular and preferred aspects of the invention are set out in the accompanying independent and dependent claims. Features from the dependent claims may be combined with features of the independent claims and with features of other dependent claims as appropriate and not merely as explicitly set out in the claims.

These and other aspects of the invention will be apparent from and elucidated with reference to the embodiments described hereinafter.

BRIEF DESCRIPTION OF THE DRAWINGS

FIG. 6 is a flow diagram of a method that can be performed by a system according to an embodiment of the present invention, where an operator can configure a flow rate for feeding a patient.

FIG. 8(a) shows a first example of a raw pressure signal as can be obtained by a system according to an embodiment of the present invention.

FIG. 8(b) and FIG. 8(c) show an example of gastric motility information extracted from the signal of FIG. 8(a), referred to herein as "short-term-Gastric Balloon Motility Index" (abbreviated as STGBMI) and "long-term Gastric Balloon Motility Information Index" (abbreviated as LTGBMI) respectively.

FIG. 9(a) shows a second example of a raw pressure signal as can be obtained by a system according to an embodiment of the present invention.

FIG. 9(b) and FIG. 9(c) show an example of gastric motility information extracted from the signal of FIG. 9(a), referred to herein as "short-term-Gastric Balloon Motility Index" and "long-term Gastric Balloon Motility Information Index" respectively.

In FIG. 10 the long-term-gastric-motility index is compared with a single threshold value. In FIG. 11 the long-term-gastric-motility index is compared with two threshold values. In FIG. 12 the long-term-gastric-motility index is compared with three threshold values.

FIG. 14 shows an example of "filtering", as can be used in step a) of FIG. 13a to FIG. 13d.

FIG. 17 shows examples of other characteristics that may be used in step b3) of FIG. 15 and FIG. 16 to evaluate whether the peak qualifies as a valid Gastric Contraction Peak.

FIG. 18(a) shows an example of a raw pressure signal. FIG. 18(b) shows a signal obtained from the raw pressure signal of FIG. 18(a) related to breathing, referred to herein as "breathing signal". FIG. 18(c) shows a possible technique for determining a baseline which can be used to obtain the breathing signal of FIG. 18(b).

FIG. 19(a) shows an exemplary raw pressure signal, FIG. 19(b) shows a second derivative of the signal of FIG. 19(a), and FIG. 19(c) shows the signal of FIG. 19(a) without the artefact, as can be obtained for example by interpolation.

DETAILED DESCRIPTION OF ILLUSTRATIVE EMBODIMENTS

Figure 1:
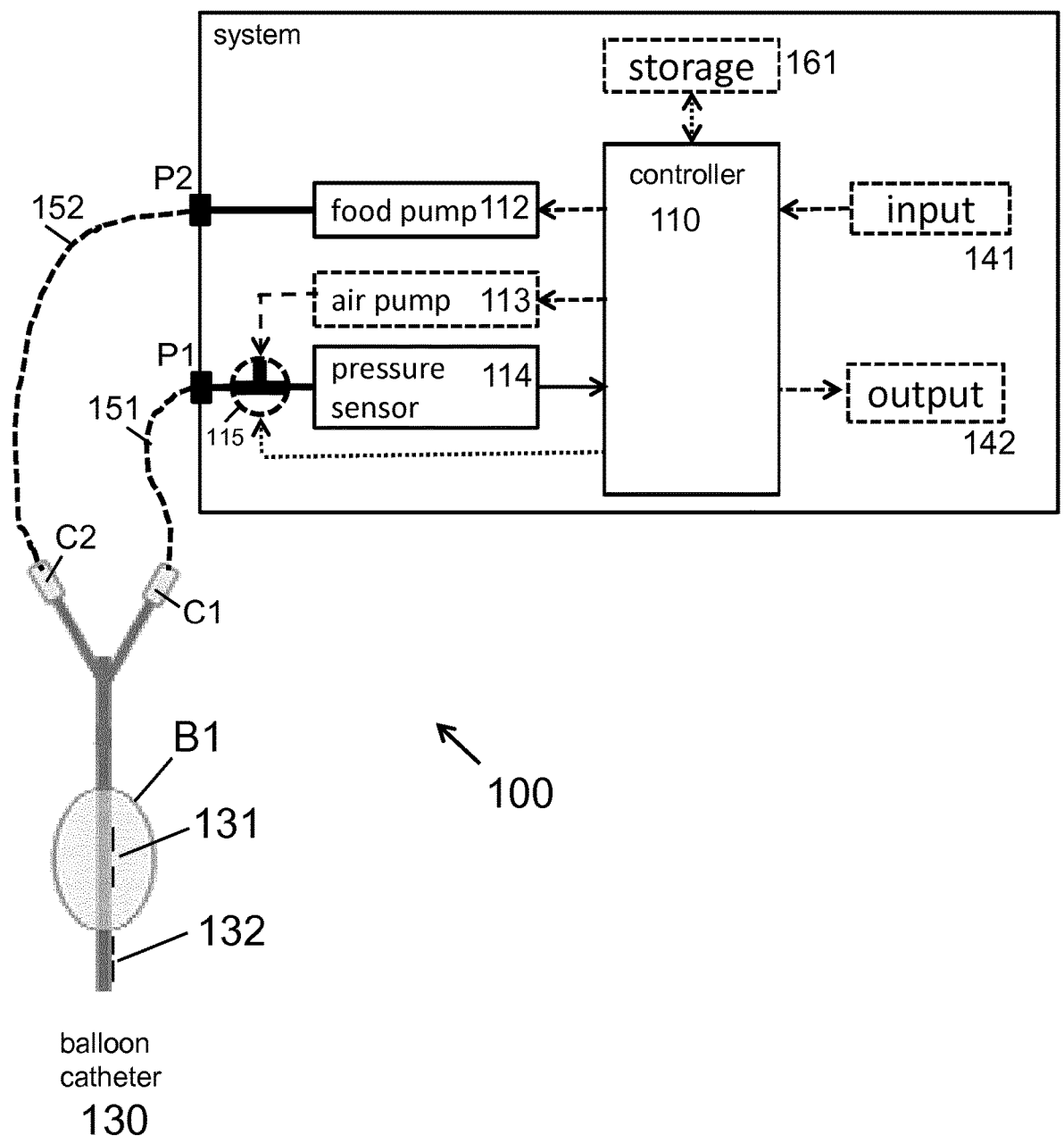
FIG. 1 shows a schematic block diagram of a system according to an embodiment of the present invention. The system comprises or is connectable to a balloon catheter with one balloon and having one lumen for feeding.

The present invention will be described with respect to particular embodiments and with reference to certain drawings but the invention is not limited thereto but only by the claims. The drawings described are only schematic and are non-limiting. In the drawings, the size of some of the elements may be exaggerated and may not be drawn to scale for illustrative purposes. The dimensions and the relative dimensions may not correspond to actual reductions to practice of the invention.

Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

In this document, the expression "gastric balloon motility index" and "gastric motility index" and "motility index" or "motility value" are used as synonyms. They refer to a "motility index" or "motility value" derived from pressure measurements obtained from a gastric balloon, in particular air pressure measurements.

Figure 13A:
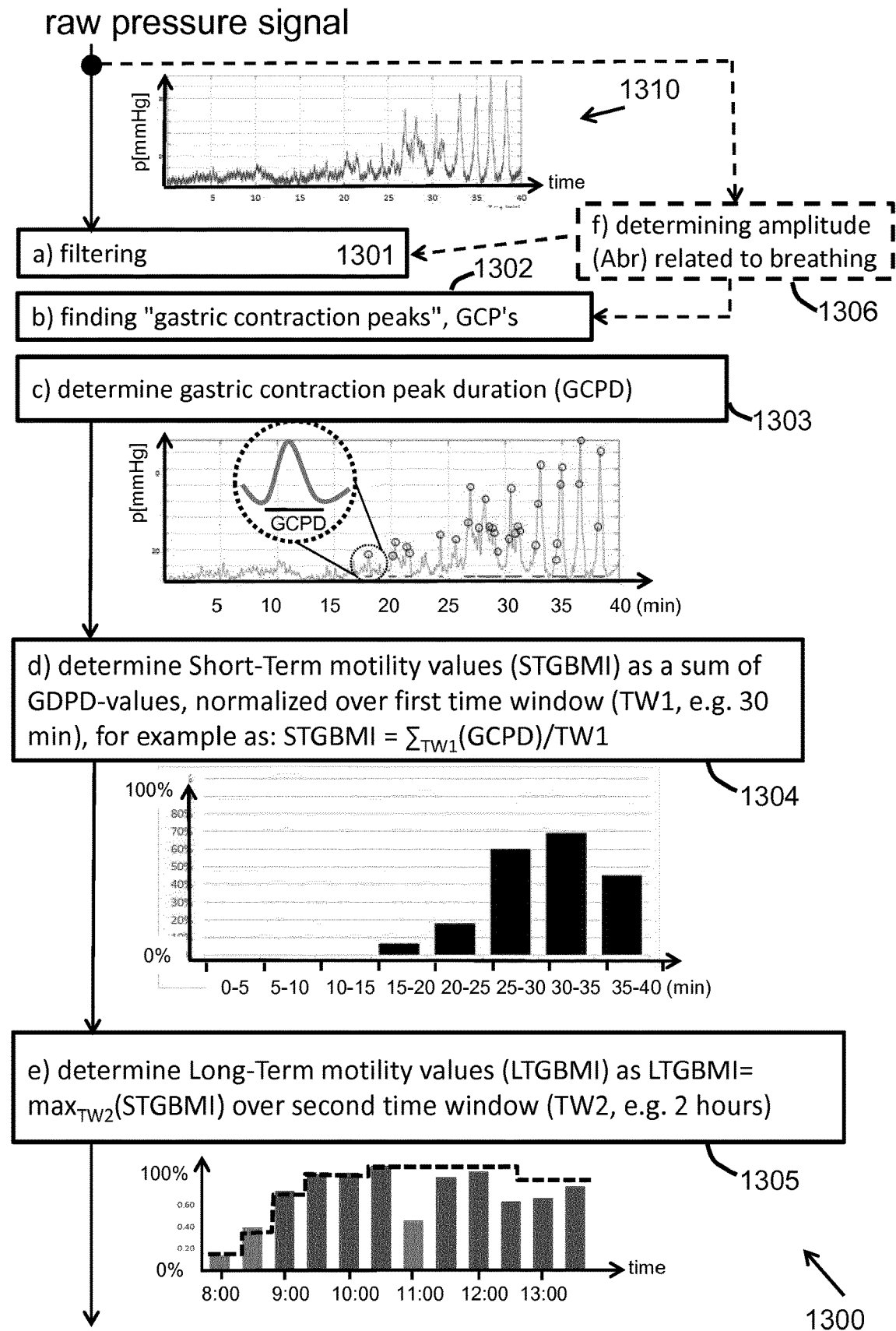
FIG. 13a shows an exemplary algorithm for determining gastric-motility-information (more specifically, a short-term-gastric-motility-value STGBMI, and a long term gastric-motility-value LTGBMI), derived from the raw pressure signal, as can be used in embodiments of the present invention. This algorithm is a more specific version of the algorithm shown in FIG. 13d (branch i).
Figure 13B:
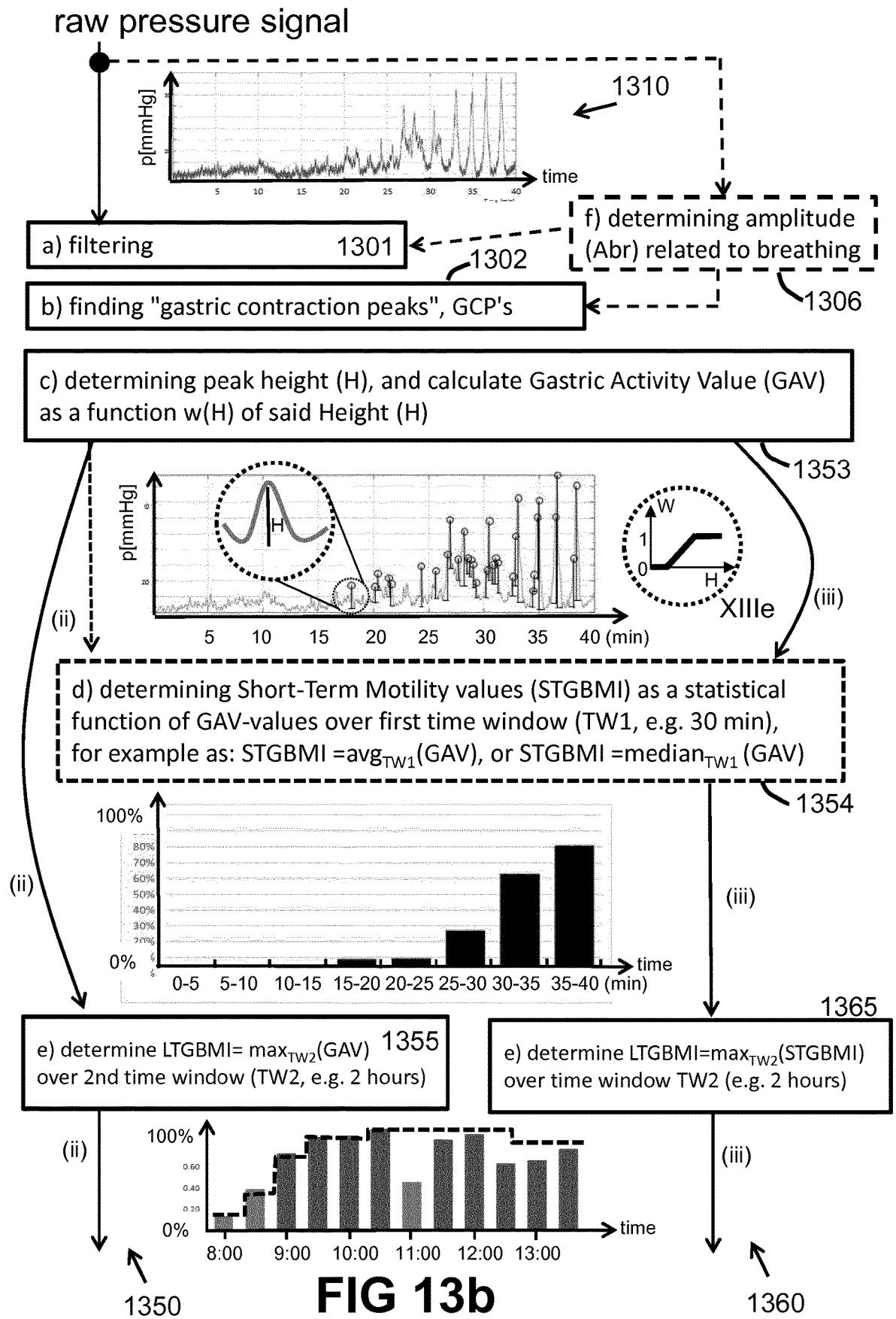
FIG. 13b shows another exemplary algorithm for determining gastric-motility-information derived from the raw pressure signal, as can be used in embodiments of the present invention. This algorithm is a more specific version of the algorithm shown in FIG. 13d (branch ii and iii)
Figure 13C:
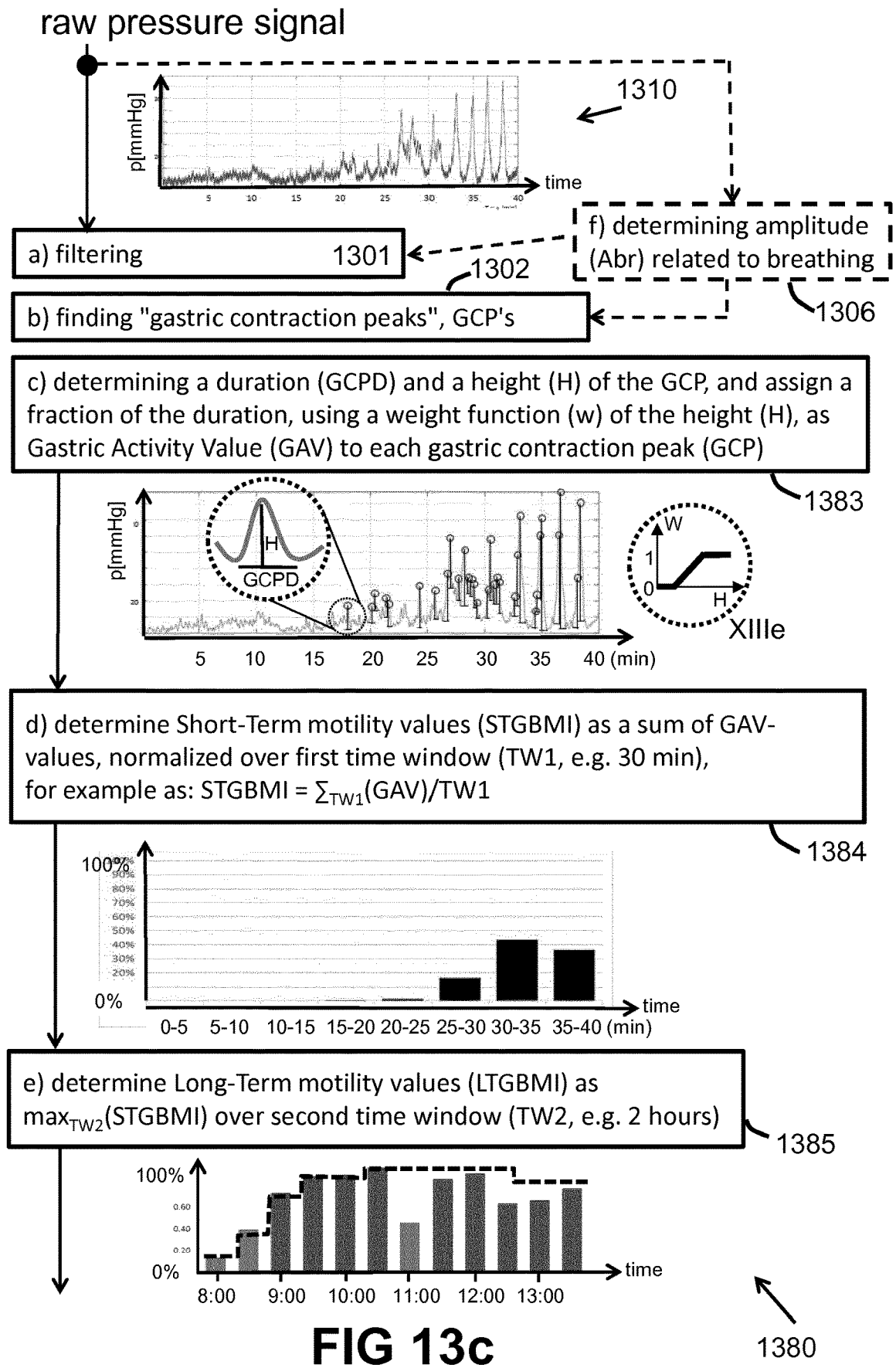
FIG. 13c shows another exemplary algorithm for determining gastric-motility-information derived from the raw pressure signal, as can be used in embodiments of the present invention. This algorithm is a more specific version of the algorithm shown in FIG. 13d (branch iv).
Figure 13D:
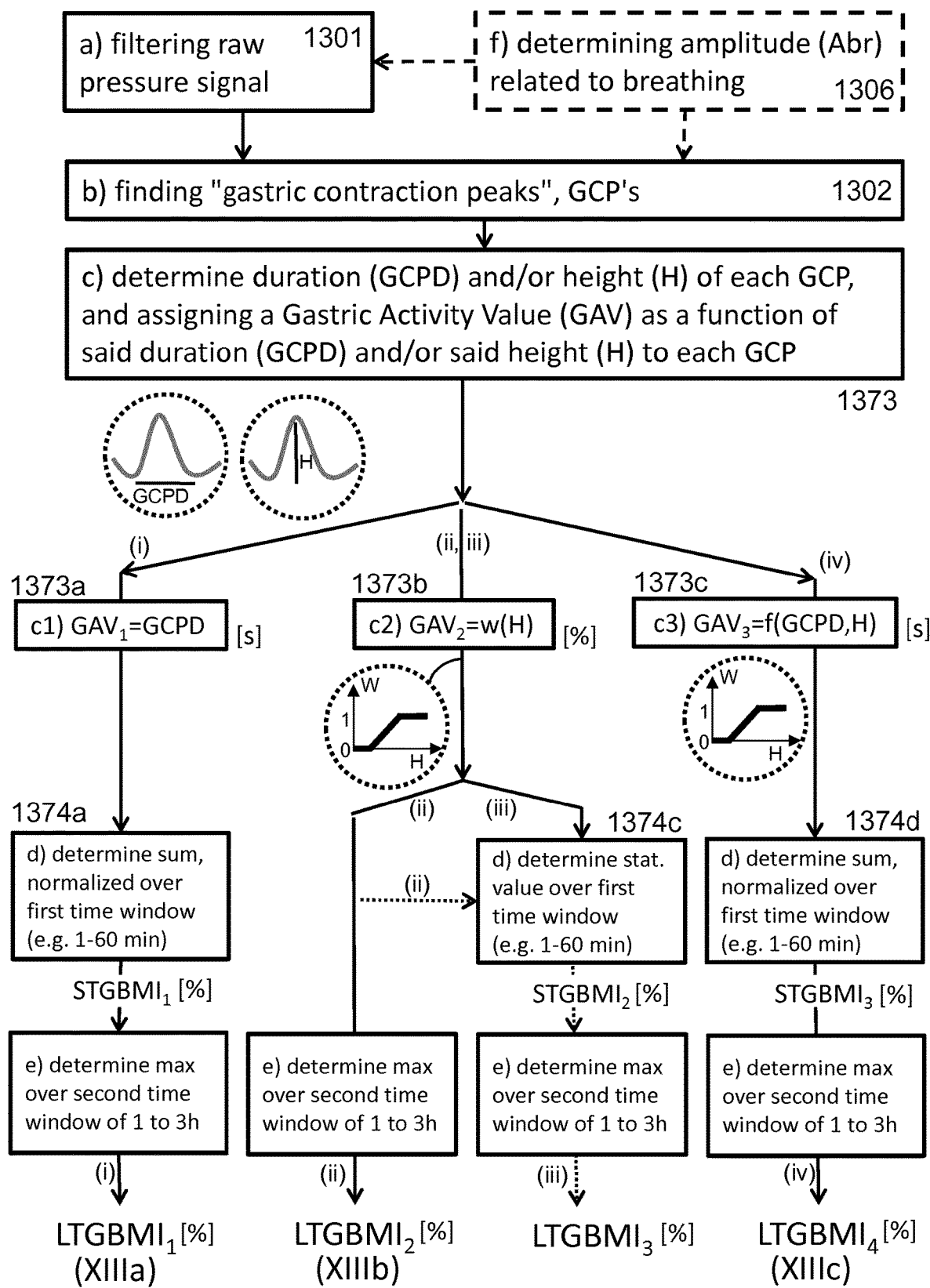
FIG. 13d is a schematic representation of a flow-chart of a general form of the so called "first algorithm" as can be used in embodiments of the present invention.

When reference is made to "gastric motility information" or "gastric-motility-values", reference can be made to one or both of the short-term gastric motility values (abbreviated herein as STGBMI) or long-term gastric-motility values (abbreviated herein as LTGBMI), which may be calculated in different ways (see FIG. 13d).

In this document, the expression "gastric contraction peak duration" and "peak duration" are used as synonyms.

When reference is made to "gastric activity values" (abbreviated as GAV), reference is made to a function of the peak duration and/or the peak height, see for example the specific examples of FIG. 13d.

When reference is made to a "gastric-motility-curve", reference is made to a time-continuous or a time-discrete graphical representation of gastric-motility-values, for example a bar-diagram or a curve as shown for example in FIG. 8b, FIG. 8c, FIG. 9b or FIG. 9c.

When reference is made herein to "short-term-gastric-balloon-motility-value", for example as opposed to "long term motility value" or in the context of displaying relevant information to medical personnel, reference is made to one or more of the STGBMI-values of FIG. 13a to FIG. 13d.

When reference is made herein to "long-term-gastric-balloon-motility-value", for example as opposed to "short-term motility value" or in the context of controlling the food pump, reference is made to a numerical value (e.g. a percentage) calculated as a maximum of GAV-values or as a maximum of STGBMI-values over a second time window of 1 to 3 hours, or 1.5 to 3 hours, or 1.5 to 2.5 hours.

The present invention relates to systems for determining gastric motility, and more in particular to a system comprising or connectable to a balloon catheter comprising a catheter and at least one balloon. The balloon can be inserted (in deflated condition) into the stomach of a patient and can then be inflated, typically with air. The system further comprises at least one pressure sensor in fluid connection with the air inside the balloon, such that mechanical pressure exerted on the surface of the balloon is translated into an increase of air pressure which can be sensed by the pressure sensor. The pressure values are read by the controller which is further adapted with an algorithm for extracting motility information from said pressure values. The motility information can be recorded, and/or visualized. The system may also comprise at least one food pump for providing enteral feeding to the patient. The food pump can provide a configurable volume of nutrients at a configurable flow rate. This volume and this flow rate can be manually entered by an operator via a user interface, and/or can be automatically adjusted (e.g. decreased or stopped, or optionally even increased) dependent on whether the stomach is working well, as reflected by the gastric motility information.

While embodiments of the present invention may work with different kinds of balloon catheters, preferably a balloon catheter is used as described in co-pending patent application WO2019030312, with the title "APPARATUS FOR MEASURING PRESSURE CHANGES IN STOMACH", filed by the same applicant around May 15, 2018, further referred to herein as "the co-pending balloon-application", which document is included herein by reference in its entirety, especially the description of the balloon catheter itself. In case of conflicts between the present invention and statements made in the co-pending application, the present document prevails.

While preferred, it is not absolutely required that the balloon catheter comprised in or connected to or connectable to a system according to the present invention, is insertable via the nose. Systems according to the present invention will also work with a balloon catheter comprising a balloon which is inserted via the mouth. However, in order to obtain sufficiently accurate results, the balloon is preferably adapted for having an overall non-spherical shape with a cylindrical portion, the cylindrical portion having a diameter in the range from 4.0 to 7.0 cm and an overall volume in the range from about 90 ml to about 330 ml (preferably from about 160 to about 235 ml), when inflated by a pressure of 0.20 psi (or 1.379 kPa) in an environment of 20° C. and 1013 mbar absent a counter-pressure, and is preferably made of a material having a durometer of at least 70 shore A. In preferred embodiments, the balloon is made of a polyurethane material having a durometer in the range from 70 to 100 shore A.

Referring to the figures,

FIG. 1 shows a schematic block diagram of a system 100 for monitoring gastric motility of a patient and for feeding said patient based on the determined gastric motility.

FIG. 1 further shows a balloon catheter 130 which may be part of the system 100, or may be connectable thereto. The balloon catheter 130 comprises a catheter and at least one inflatable balloon B1 (only one balloon B1 is shown in FIG.

1). The at least one balloon B1 is adapted to be positioned in a stomach of the person. The first lumen has at least one first opening 131 (schematically illustrated by two line segments and an opening in between), in fluid connection with the inside (or cavity or hollow space) of the balloon B1. The balloon B1 can be inflated by inserting air into the first lumen, and can be deflated by extracting air from the first lumen. The balloon B1 of FIG. 1 also has a second lumen adapted for providing a substantially liquid substance (e.g. nutrients and/or drugs) to the person. The second lumen comprises at least one second opening 132, located outside the balloon B1. The position of the at least one second opening 132 may for example be at a distance from about 0.1 cm to about 5 cm from the balloon B1 if the substance is to be provided in the stomach of the person. In a variant of the balloon catheter 130, the at least one second opening 132 is located at a distance of about 5 cm to about 50 cm from the balloon B1, for providing food directly into the small intestine. The balloon catheter 130 of FIG. 1 has a first connector C1 fluidly connected with the first lumen, and a second connector C2 fluidly connected with the second lumen. The first connector C1 and the second connector C2 may have a different colour and/or a different shape to reduce the risk of incorrect connection to the system.

The system 100 of FIG. 1 comprises a first port P1 connectable or connected to the first lumen of a balloon catheter 130, for example directly by connecting the first connector C1 to the first port P1, or indirectly via a first tube 151. The system further comprises a pressure sensor 114 fluidly connected or connectable to the first port P1 for measuring a pressure of a fluid (e.g. air) inside the balloon B1, when inflated. The system 100 further comprises a controller 110 operatively connected to the pressure sensor 114 for obtaining pressure values indicative of a pressure inside the balloon B1. The system 100 further comprises a second port P2 connected or connectable to the second lumen of the balloon catheter 130, e.g. directly or indirectly via a second tube 152. The system 100 further comprises a food pump 112 connected or connectable to the second port P2, and adapted for providing said substance, e.g. food. The controller 110 is operatively connected to the food pump 112 for configuring or for driving the food pump 112 so as to provide said substance (e.g. containing liquid food and/or drugs) at a configurable flow rate. The controller 110 further contains computer executable instructions comprising first code fragments for performing a first algorithm 1300 (see e.g. FIG. 13a to FIG. 13f) for extracting 603; 703 (see FIG. 6 and FIG. 7) gastric motility information from the measured pressure values, and second code fragments for performing a second algorithm (see e.g. FIG. 10 to FIG. 12) for dynamically adjusting 708 said volume of nutrient to be supplied to the patient and/or said flow rate based on said extracted gastric motility information.

The pressure is preferably sampled at a frequency of at least 1 Hz, for example at a frequency in the range from 1 to 50 Hz, or from 1 to 20 Hz, or from 1 to 10 Hz, for example at 5 Hz or at 10 Hz.

As will be discussed further in FIG. 5, the controller 110, 210, 310, 410, 510 may contain a single computing device such as for example a desktop computer or a laptop computer for mainly performing the "heavy calculations" and an interface device such as for example a DI-245 data acquisition device, commercially available from DATAQ Instruments, Akron, Ohio, USA, for communicating with the pressure sensor and/or the food pump. Alternatively the controller may comprise multiple computing devices, for example said desktop or laptop computer on the one hand, and a micro-controller for interfacing with the pressure sensor and/or the food pump.

The system 100 preferably further comprises output means 142 for displaying 604, 704 the extracted gastric motility information, for example in the form of numerical data (a number or a percentage), or in the form of graphical data on a graphics display (e.g. a bar diagram as shown e.g. in FIG. 8b and FIG. 8c and FIG. 9b and FIG. 9c), or in the form of a color scheme using for example two color lights e.g. two color LEDs (e.g. green for indicating OK or GOOD, and red for indicating NOT OK or BAD), or using a bicolor-LED (with green and red), or in the form of three color lights, e.g. three color LEDs (e.g. green for indicating OK or GOOD, and yellow for indicating MEDIUM or STABLE, and red for indicating NOT OK or BAD).

The system 100 preferably further comprises input means 141 for receiving settings and/or commands to drive the food pump 112. The input means 141 may for example comprise a keyboard or may contain buttons, e.g. push buttons or a slider or a rotation knob, etc. The input means 141 and the output means 142 may be combined, for example in the form of a touch-screen.

In particular embodiments, the man-machine interface may also be provided via an app on a portable device, e.g. on a smart-phone, which communicates wirelessly (e.g. via Bluetooth or via Wifi or in any other suitable way) with the controller. The app may also include a text to speech module to inform a doctor. The app may also include a voice recognition module to receive input from the doctor.

The computer executable instructions to be executed on the controller 110 may further comprise third code fragments for presenting the gastric motility information on said output means 142, and fourth code fragments for receiving said settings and/or commands from the input means 141.

The system 100 may further comprise an air pump 113 connected or connectable to the first port P1 for inflating the balloon B1. The air pump may be controlled manually (e.g. via a push-button, not shown), or via the user interface provided via the controller 110. The controller 110 may be operatively connected to said air pump 113, and may be further adapted for controlling or for driving the air pump for inflating the at least one balloon B1 and/or for deflating the balloon B1, for example with a configurable volume of air (e.g. about 180 ml if the balloon has a "target volume" of 180 ml, as defined in "the co-pending balloon-application", or temporarily to a higher volume for stimulating gastric contractions, or for example with a configurable pressure (e.g. about to 0.2 psi or about 1.38 kPa), or temporarily to a higher pressure for stimulating gastric contractions.

The air pump 113 and the pressure sensor 114 may be connected to the first port P1 via a T-connector (not shown), or via a three-way valve 115 (as shown), or via multiple valves and/or switches (not shown). This valve or switch 115 or these switches may be controlled by the controller 110, or may be controlled manually.

The system 100 may further comprise a non-volatile memory (such as flash) and/or at least one storage device 161 (e.g. a Hard disk, a memory stick) operatively connected or connectable to said controller 110, and the controller 110 may further comprise fifth code fragments for storing the obtained pressure values and/or one or more values derived therefrom (e.g. short-term gastric motility values and/or long-term gastric motility values, as will be described further, e.g. in FIG. 8 and FIG. 9 and FIG. 13a to FIG. 13f), in said memory and/or in said storage device 161. Alternatively or additionally, the controller 110 may further comprise a wireless transceiver (not shown) for transmitting said data to an external device via a wireless link, e.g. to a network attached storage device, known as a "NAS".

In a variant of FIG. 1, the balloon catheter 130 does not necessarily contain the second lumen (with the second opening 132 and the second connector C2), and the system 100 does not necessarily contain the food pump 112 or the second port P2, but does contain the input means 141 and the output means 142, and the controller 110 does contain computer executable instructions comprising: first code fragments for performing the first algorithm 1300 (see e.g. FIG. 13a to FIG. 13f) for extracting 603; 703 (see FIG. 6 and FIG. 7) gastric activity information (GAV) and/or gastric motility information (e.g. STGBMI, LTGBMI) from the measured pressure values, and third code fragments for presenting the gastric motility information on said output means 142, and fourth code fragments for receiving settings and/or commands from the input means 141.

Such a system is very much suitable for monitoring the gastric motility of the patient by measuring the pressure values and visualising this data, or data derived therefrom (for example in particular the short-term-gastric-motility-index (STGBMI) and/or the long-term gastric motility index LTGBMI of FIG. 8 or FIG. 9 or FIG. 13a to FIG. 13f), and optionally storing this data.

Even if the food pump 112 is present, and even if the balloon catheter comprises the second lumen, the controller 110 does not necessarily have to control the food pump 112, but the food pump may be controlled manually. Such a balloon catheter and such a system offer the advantage of allowing to provide nutrients to the patient (manually or semi-automatically via the manually configured food pump), while having the benefit of being able to monitor and/or store gastric motility.

Figure 2:
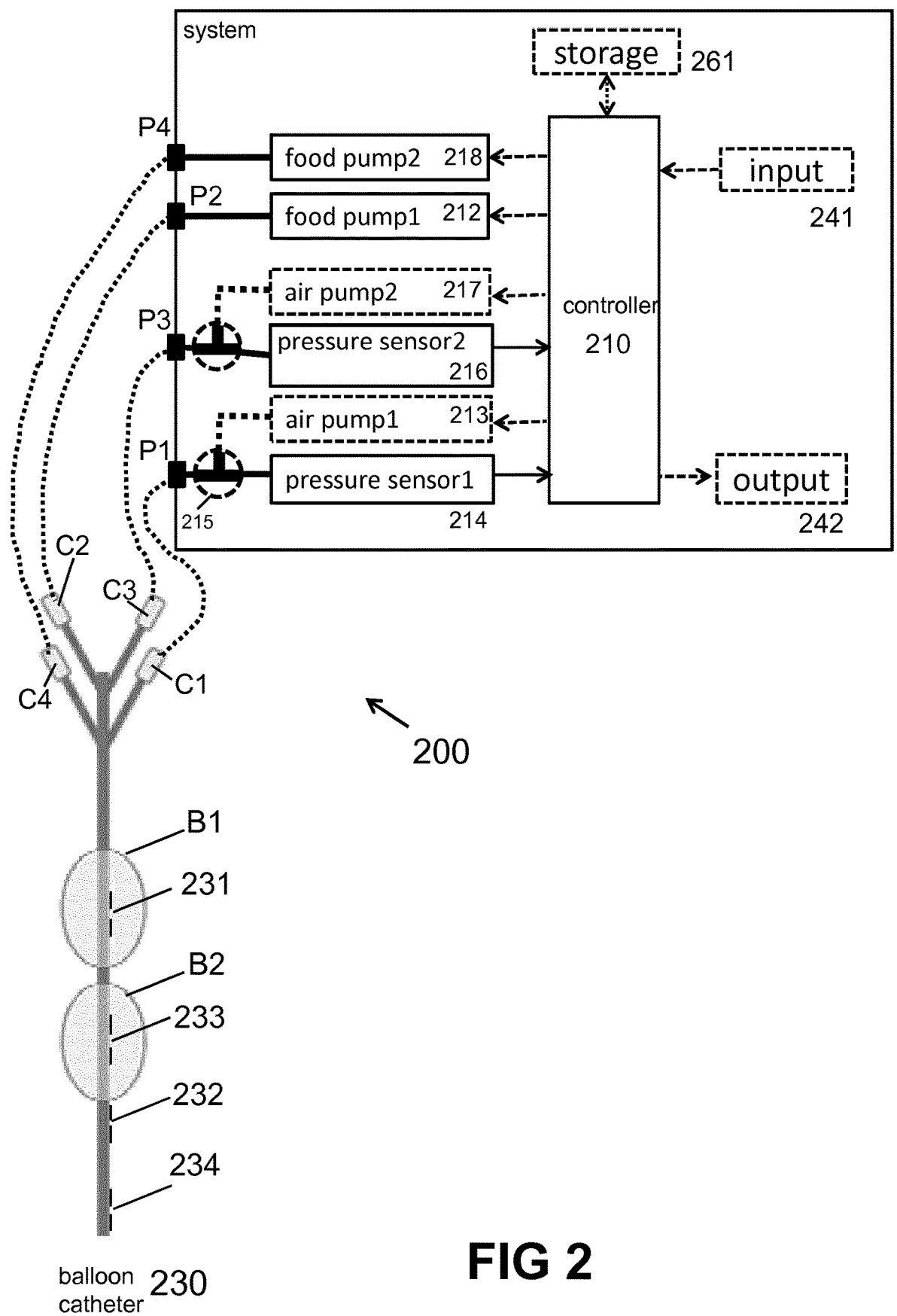
FIG. 2 shows a schematic block diagram of a system according to an embodiment of the present invention. The system comprises or is connectable to a balloon catheter with two balloons and having two lumen for feeding.

FIG. 2 shows a schematic block diagram of a system 200 according to an embodiment of the present invention comprising or connectable to a balloon catheter 230 having a first balloon B1 fluidly connected to a first lumen and accessible via a first connector C1, and a second balloon B2 fluidly connected to a third lumen accessible via a third connector C3, and having a second lumen with at least one opening 232 outside the balloons for providing a substance to the stomach via a second connector C2, and having a fourth lumen with at least one opening 234 outside the balloons for providing a substance into the small intestine via a fourth connector C4.

The system 200 of FIG. 2 can be seen as a variant of the system 100 of FIG. 1, with the main differences being that the system 200 has:
  two pressure sensors: a first pressure sensor 214 for measuring a pressure in the first balloon B1, and a second pressure sensor 216 for measuring a pressure in the second balloon B2;
  two air pumps: a first air pump 213 for inflating and/or deflating the first balloon B1 and a second air pump 217 for inflating and/or deflating the second balloon B2;
  two food pumps: a first food pump 212 for providing food into the second lumen towards the stomach via the second connector C2, and a second food pump 218 for providing food into the fourth lumen towards the small intestine via the fourth connector C4;
  the balloon catheter 230 has two separate balloons, or has a single balloon with two compartments which are substantially separate, so that the pressure in the first and second compartment may be different, but absolute hermetic sealing is not required, some leakage (for example in the order of 1 ml per minute at a pressure difference of about 1 psi between the two compartments is acceptable);
  the balloon catheter 230 has four lumen, and four connectors C1 to C4;

Everything described above for the system 100 of FIG. 1 is also applicable for the system 200 of FIG. 2 mutatis mutandis. For example, the four connectors C1 to C4 may be given a different size and/or a different color in order to avoid misconnection; the first air pump 213 and the first pressure sensor 214 may be directly connected to the first port P1 via a T-connector, or via a switch or a valve 215; the second air pump 217 and the second pressure sensor 216 may be directly connected to the third port P3 via a T-connector, or via a switch or a valve; etc.

However, the system 200 of FIG. 2 offers further advantages (over the system 100 of FIG. 1):
  i) Since there are two balloons B1, B2 and two pressure sensors 214, 216, the system 200 can measure two pressure signals. While it is expected that the two pressure signals will reveal more or less the same gastric motility information but slightly shifted in time, the system 200 can detect the direction of the gastric contractions, for example towards the esophagus (which is a bad sign) or towards the small intestine (which is a good sign).
  ii) this system contains some redundancy, which may allow to detect errors, and/or may allow to provide more accurate results, e.g. by averaging the extracted gastric activity values (GAV) and/or the gastric motility values (e.g. STGBMI, LTGBMI) extracted from the first pressure signal with the corresponding gastric activity values (GAV) and/or gastric motility values (e.g. STGBMI, LTGBMI) extracted from the second pressure signal.

It is contemplated that a single air pump may be sufficient to selectively inflate the first and the second balloon B1, B2, one after the other, if suitable routing and switching is provided to selectively operatively connect the single air pump to the first port P1 and the third port P3. It is preferred however to have two separate air pumps, because this simplifies the control, the risk of incorrectly operating them is drastically reduced, and in case of emergency, having two air pumps allows to deflate the two balloons faster than is possible with a single pump.

Figure 4:
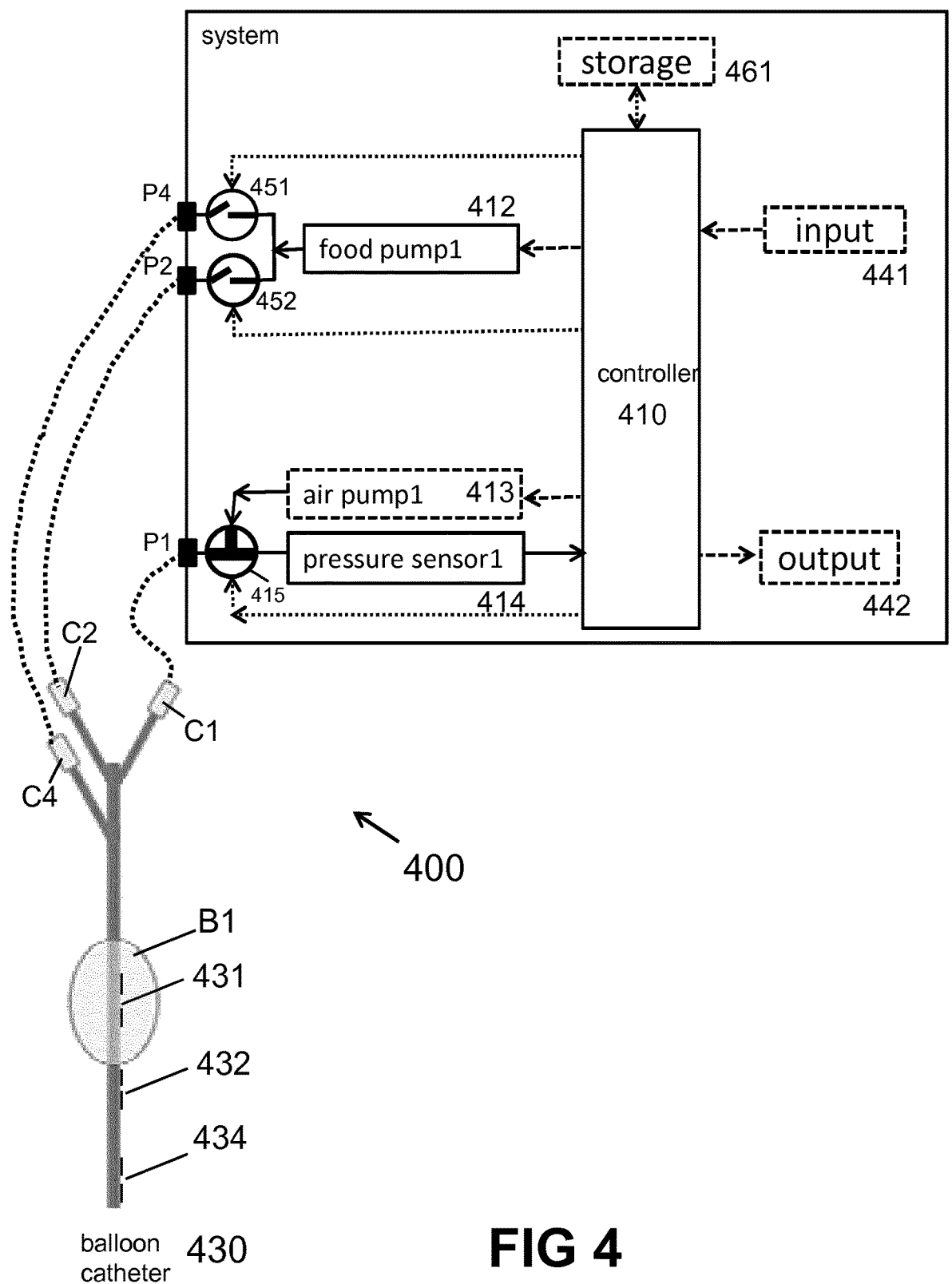
FIG. 4 shows a schematic block diagram of a system according to an embodiment of the present invention. The system comprises or is connectable to a balloon catheter with one balloon and having two lumen for feeding.

It is contemplated that a single food pump may be sufficient to selectively provide food either into the stomach (via the second port P2, the second connector C2, the second lumen and the second opening 232) or into the small intestine (via the fourth port P4, the fourth connector C4, the fourth lumen and the fourth opening 234). A single food pump is actually preferred, because if the stomach is working well, food is preferably supplied into the stomach and not into the small intestine, and if the stomach is not working well, food is preferably supplied into the small intestine and not into the stomach. In fact, this sub-circuit is shown in FIG. 4, and the skilled person can easily modify the block-diagram of FIG. 2 accordingly.

If the system 200 comprises output means 242, it is contemplated that controller 210 may provide two values or two graphs (one for each pressure signal); or a single value or a single graph (for one of the pressure signals or a combined value, for example an averaged value, or an average value after time-shift correction), or a single value or a single graph and a confidence level. The confidence level would be high if the motility index obtained from the first and second pressure signal are quite similar (e.g. deviate less than a predefined value, e.g. less than 5% or less than 10% or less than 15% or less than 20%), and the confidence level would be low if the motility index obtained from the first and second pressure signal deviate substantially (e.g. deviate more than said predefined value).

In a variant of the system of FIG. 2, the balloon catheter 230 contains two balloons, but no lumen for feeding, and the system does not contain any food pump. Such a system can be used for monitoring gastric motility.

Figure 3:
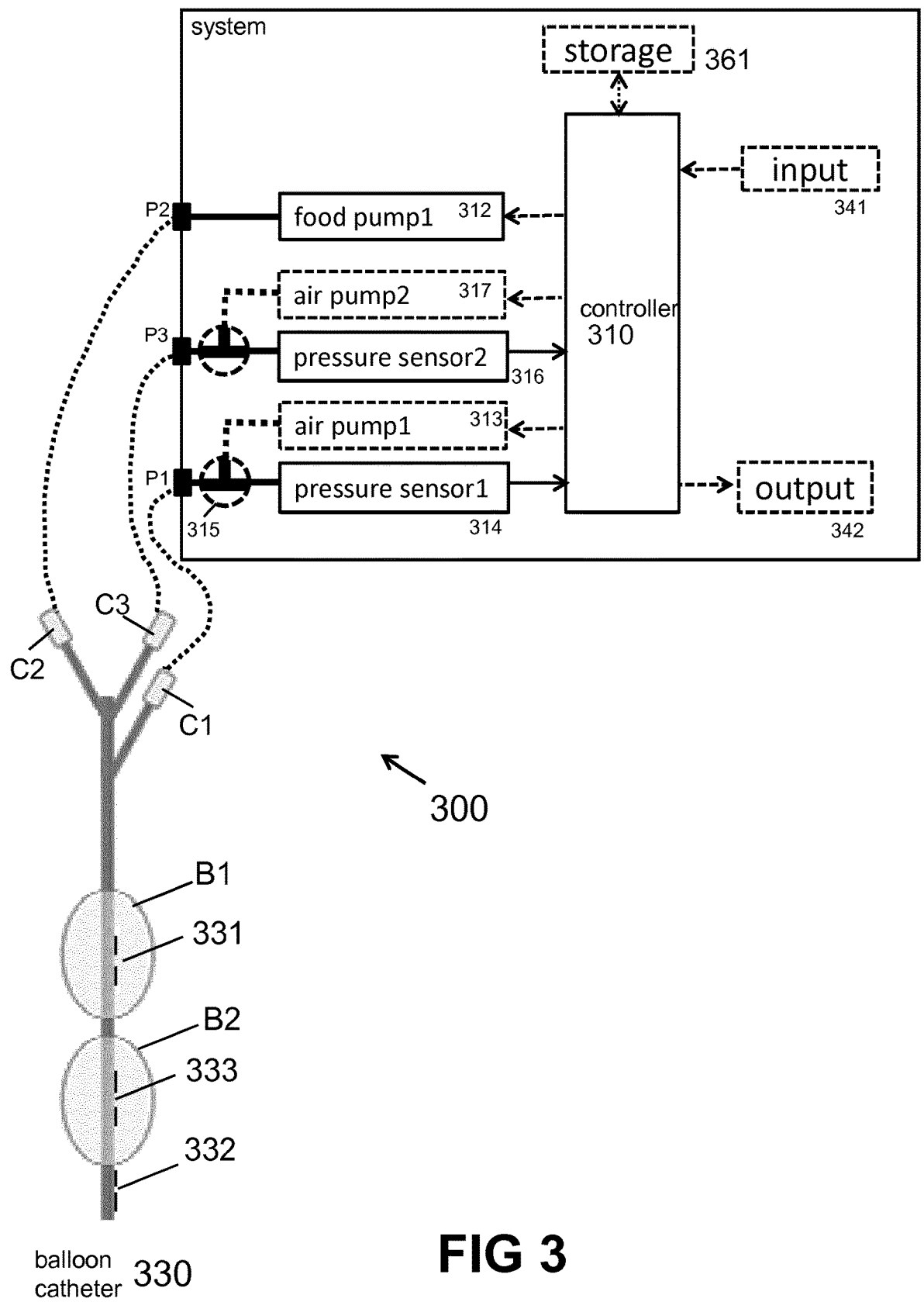
FIG. 3 shows a schematic block diagram of a system according to an embodiment of the present invention. The system comprises or is connectable to a balloon catheter with two balloons and having one lumen for feeding.

FIG. 3 shows a schematic block diagram of a system 300 that can be seen as a variant of the system 200 shown in FIG. 2, where the second food pump 218, and the fourth port P4 are omitted, and wherein the balloon catheter 330 does not have the fourth lumen with the fourth connector C4 and the fourth opening 234 towards the small intestine, but does have the opening(s) 232 towards the stomach. Everything else described above for the system 200 of FIG. 2 is also applicable for the system 300 of FIG. 3 mutatis mutandis.

In another variant of FIG. 2, (not shown), the first food pump 211, and the second port P2 are omitted, and the balloon catheter does not have the second lumen with the second connector C2 and the second opening 232 towards to stomach, but does have the opening(s) 234 towards the small intestine. Everything described above for the system 200 of FIG. 2 is also applicable for this variant, mutatis mutandis.

The skilled person will understand that these two systems (the one shown in FIG. 3 and the other variant of FIG. 2 described in the previous paragraph) are very similar, and that the main difference between them is the position of the opening of the balloon catheter for providing food into the stomach or into the small intestine. The electronics and software of these systems can be identical.

FIG. 4 shows a schematic block diagram of a system 400 that can be seen as a variant of the system 100 of FIG. 1, where a fourth lumen with a fourth connector C4 and one or more opening(s) 434 towards the small intestine are added; and wherein one or more switches 451, 452 or a valve are added to selectively couple the food pump 412 to the second port P2 towards the stomach and to the fourth port P4 towards the small intestine, and where the controller 410 may be provided with additional code fragments for controlling said valves or said switches. Everything else described above for the system 100 of FIG. 1 is also applicable for the system 400 of FIG. 4 mutatis mutandis.

Or the block-diagram of FIG. 4 can also be seen as yet another variant of the system 200 of FIG. 2, wherein the second air pump 217 and the third port P3 are omitted; and wherein the balloon catheter 430 does not have the third lumen with the third connector C3 and the third opening(s) 233 towards the second balloon B2; and wherein the second food pump 218 is omitted. Everything else described above for the system 200 of FIG. 2 is also applicable for the system 400 of FIG. 4 mutatis mutandis.

As already described above, while it is technically possible to provide two food pumps (as in the block-diagram of FIG. 2), it is preferred to have only a single food pump 412 to selectively provide food to either the second port P2, which leads to the opening(s) 432 in the stomach, or to the fourth port P4, which leads to the opening(s) 434 in the small intestine.

In the block-diagrams of FIG. 1 to FIG. 4, the "controller" is represented by a single block, and the blocks "storage", "input" and "output" are shown as separate blocks.

In an embodiment, these four blocks may be implemented by a laptop computer with appropriate software (as will be described further, see e.g. FIG. 6 and FIG. 7 and FIG. 13a to FIG. 13f), and an extension board for interfacing with the pressure sensor(s) and/or the food pump(s) and/or the switch(es) or valve(s). But that is not the only possible implementation.

Figure 5:
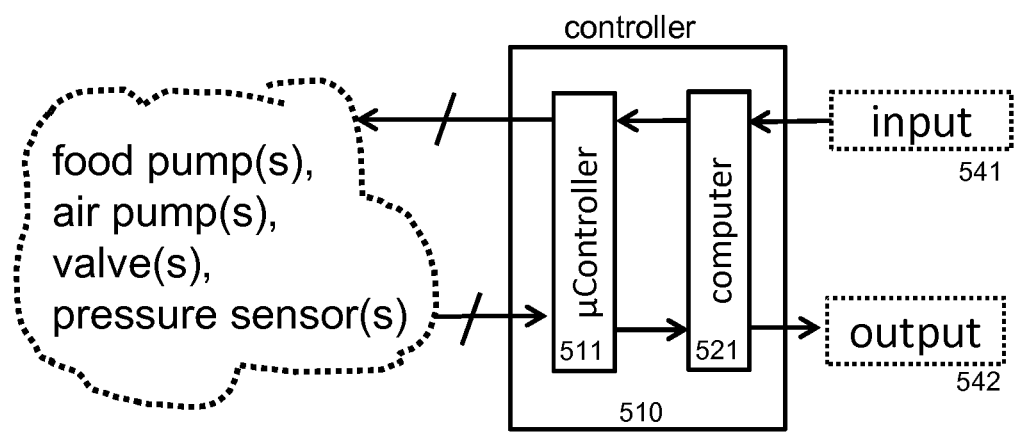
FIG. 5 shows a schematic block diagram of a controller as can be used in a system according to embodiments of the present invention.

The block "controller" may comprise multiple devices or multiple subsystems, for example, as illustrated in FIG. 5, where the controller 510 comprises a first computing device 511 and a second computing device 521. In the configuration shown in FIG. 5, the first computing device takes care of the interfacing with the one or more pressure sensor(s) and the one or more food pump(s) if present, and the one or more switch(es) and/or valve(s) if present, while the second computing device 521 takes care of interfacing with the input 541 and output means 542, which may be external to the second computing device (e.g. in case of a desktop computer or a motherboard etc.) or may be incorporated in the second computing device (e.g. in case of a laptop). The first computing device may for example comprise a simple 8-bit or 16-bit microcontroller with limited resources in terms of clock-speed (e.g. in the order of 20 to 40 MHz), RAM (typically less than 1 MByte), internal or external flash or ROM space (typically less than 16 MByte). The second computing device may contain a processor (e.g. an AMD or INTEL processor) running at a clock speed of at least 1.0 GHz, at least 4 GByte of RAM, at least 256 GBytes of storage capacity, etc. As will become clear further, the second computing device 521 is much better suited for performing what is referred to herein as "the first algorithm" (e.g. in step 603 and step 703), and for optionally displaying the results graphically (e.g. in step 604 and step 704).

Of course other hardware configurations or topologies are possible, e.g. a dedicated printed circuit board PCB with a Digital Signal Processor (DSP), or with a Field Programmable Gate Array (FPGA) or even with an Application Specific Integrated Circuit (ASIC). The skilled person having the benefit of the present disclosure, can easily find other topologies.

FIG. 6 is a flow diagram showing two methods 600a and 600b that can be performed by a system according to an embodiment of the present invention. Or stated differently, the controller of these systems is adapted for performing one or both of these methods.

In embodiments without a food pump (e.g. systems only intended for monitoring and visualising and optionally storing gastric activity), the controller would be provided only with code fragments for performing the method 600a (loop1). In embodiments with a food pump, the controller would be provided with code fragments for performing both the method 600a (loop1) and the method 600b (loop2), and an operator can manually set or configure a flow rate for feeding a patient, for example at least partly based on the displayed gastric-motility values.

The method 600a comprises at least the following steps:
a) measuring 601 pressure values, and storing or buffering the pressure values at least temporarily in a memory (e.g. RAM);
c) calculating 603 gastric motility values (e.g. one or more of STGBMI, LTGBMI) based on said pressure values;
d) presenting 604 one or more of the gastric motility values (e.g. one or more of STGBMI, LTGBMI), optionally accompanied with a recommendation.

An example of the result of step 604 is given in FIG. 8(b), FIG. 8(c), FIG. 9(b) and FIG. 9(c).

More detailed examples of step 603 will be provided in FIG. 13a, FIG. 13b and in FIG. 13c, but the present invention is not limited to these examples. The algorithm behind step c) of FIG. 6 is one of the underlying ideas of the present invention, and is referred to herein as "the first algorithm".

The method 600a may further comprise the following step:

b) displaying 602 the (raw) pressure values.

An example of the result of this step is shown in FIG. 8(a) and FIG. 9(a) and FIG. 22(b).

One of the underlying problems which the present invention tries to solve is that the raw pressure signals are not easy to interpret, due to several reasons (e.g. influence of breathing, sneezing), differences between individuals and/or situations, especially if the gastric activity is less active than the examples shown here, which were taken from perfectly healthy people. The present invention provides a solution that transforms the raw pressure signal into objective information that is easy to understand, yet is highly robust (e.g. independent of a person's weight and/or position) and/or highly insensitive to disturbances caused by e.g. breathing, coughing, sneezing, etc.

Assuming that at least one food pump is present, the controller may be further adapted to also perform the method 600b represented by the second loop "loop2", comprising the following steps:

e) initialising 605 one or more settings (or parameters) to disable the food pump. This is how the system normally starts up.

f) testing 606 whether new settings are available, for example by polling the input means (e.g. one or more push buttons, a slider, a rotation knob, a touch-screen, a mouse button, etc.), and if no new settings are available, maintaining 608 the current settings in step h);

and if new settings are available, reading or receiving 607 the new settings, e.g. via the input means, in step g);

i) controlling or driving 609 the at least one food pump based on the settings 609.

In an embodiment, the "settings" comprise at least one parameter, being the "flow rate" of the at least one food pump. In an embodiment, the "settings" comprise at least two parameters, comprising "a volume" to be administered to a patient, and an "initial flow rate" of the food pump.

As can be seen in FIG. 6, there is no coupling between the first loop and the second loop. The idea behind this "monitoring system" or "monitoring and feeding system" is that a doctor can see the Gastric Motility information provided by the system (in step 604), and can take an informed decision based on this information, for example to start providing enteral feeding to the patient into the stomach, or into the small intestine, or to increase or decrease the flow rate, or to stop providing enteral feeding, e.g. after considering the gastric motility-information (e.g. STGBMI, LTGBMI), especially based on the short-term gastric motility information (STGBMI) and/or the long term motility information (LTGBMI). The commands can be (e.g. manually) input into the system via the input means. It is a major advantage of this system that it allows to monitor the gastric activity of the patient, and that "the first algorithm" interprets this data, and may even provide a recommendation to start or stop feeding the patient. The system takes care of the difficult interpretation of the raw pressure data, and converts this data into a gastric motility value or curve which is easier to understand. By doing so, it allows the medical staff to take an informed decision. It is important to note that, in this system, the medical staff is the one who takes all decisions and provides corresponding instructions for the system. The second loop executes these instructions by controlling the food pump(s) as instructed. Since re-assessment of the feeding protocol typically takes place only once or a couple of times per day, this means in practice that the settings are fixed for a longer period (e.g. 12 to 24 hours), which is not ideal.

Figure 7:
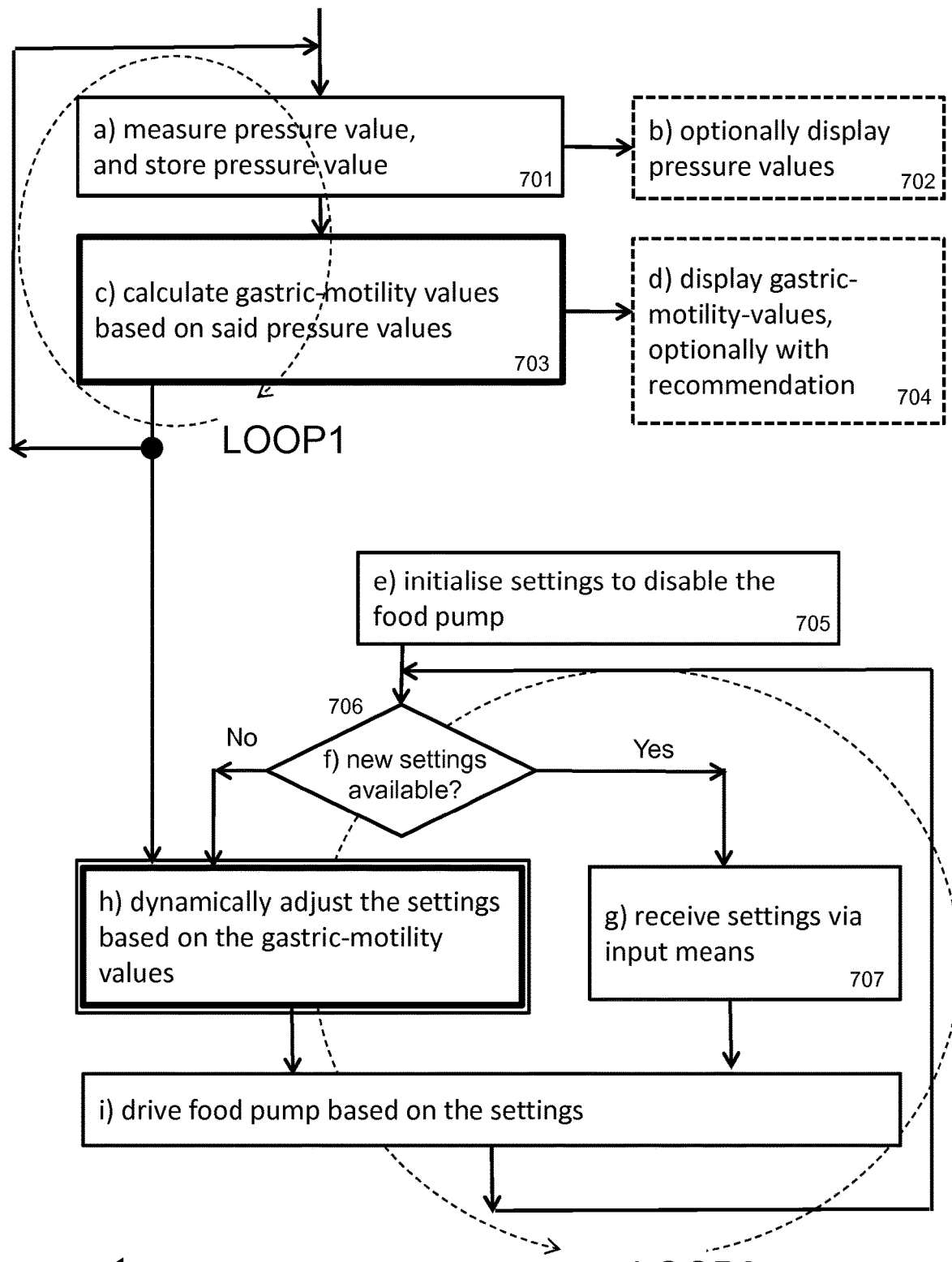
FIG. 7 is a flow diagram of a method that can be performed by a system according to an embodiment of the present invention, where an operator can configure an initial flow rate for feeding a patient, but where the system can adjust the settings and/or the flow rate, depending on the measured gastric motility.

FIG. 7 is a flow diagram of a method 700 which can be performed by a system according to an embodiment of the present invention. Or stated differently, the controller of these systems is adapted for performing this method.

The method of FIG. 7 is a variant of the combined methods of FIG. 6, and can only be performed by a system that comprises at least one food pump. The main differences with the combined methods of FIG. 6 are:

step d) of displaying 704 the Gastric Motility Information is not mandatory, but optional;

an output of step c) is provided as input for the second loop. This is a major change, the impact of which should not be underestimated;

step h) of the second loop takes the gastric motility information calculated in step c) as input, and can use it to dynamically adjust 708 the settings.

In contrast to the method of FIG. 6, in the method of FIG. 7 there is a clear coupling between the first loop and the second loop. The examples of FIG. 8 and FIG. 9 are still applicable.

In preferred embodiments, the optional step d) is present.

The idea behind this "monitoring and feeding system" is that the medical staff can still see the gastric motility information provided by the system (in step 704), and can still take an informed decision based on this information, to start providing enteral feeding to the patient, or to stop providing enteral feeding, and to (optionally) determine an initial location of feeding (e.g. into the stomach or into the small intestine), and to determine an initial flow rate for the food pump. And these commands or instructions can still be input into the system. And the "first algorithm" (in step 703) still interprets the pressure data, and can still provide a recommendation to the medical staff (in step 704), and the important decisions are still taken by the medical staff, but the main benefit of this system is that, in between the medical staff visits, the system may dynamically adjust the settings based on the gastric motility information obtained in the first loop, for example by slightly decreasing the flow rate if the gastric motility index is not very good, or to stop the flow rate if the gastric motility index is bad, or even to slightly increase the flow rate if the gastric motility index is very good.

In embodiments where the balloon catheter has a second lumen for feeding into the stomach and a fourth lumen for feeding into the small intestine, the controller may also take the decision to switch the feeding location, for example from feeding into the stomach to feeding into the small intestine (which is safer) in case the gastric motility information is not so good, or even for switching from feeding into the small intestine to feeding into the stomach if the gastric motility information is very good.

The main advantage of this (more intelligent) system of FIG. 7 is that the system can react much faster than between visits of the medical staff. In practice this means for example that an adjustment is possible after about 1-2 hours instead of only after 24 hours. While this fast reaction time is important in itself (it may prevent major complications), the potential positive impact may actually be much larger, because today, a very conservative approach is taken concerning enteral nutrition, because feedback is only received after an extensive period (e.g. 24 hours) when measuring the residue through gastric residual volume determination. However, with a system according to the present invention, a somewhat less conservative approach can be made, and the medical staff can for example "try" to start feeding into the stomach sooner, or "try" to increase the flow rate sooner in the curing process, knowing that the system will only maintain this attempt if the motility index is good, and especially knowing that the system will adjust the settings to safer settings if the motility index is not so good. This may have a major impact on the patient's recovery time, and thus also on hospital costs.

Of course, the method shown in FIG. 7 is only a simplified flow-chart, and many refinements are possible in an actual implementation. For example, the system may have a graphical user interface allowing medical staff to enable or disable automatic adjustments (meaning for example to switch between the behaviour of FIG. 6 and FIG. 7), or to enable only "downscaling" towards safer settings (e.g. from feeding into the stomach to feeding into the small intestine, but not the other way around; e.g. decreasing or stopping the flow rate, but not increasing), or to enable also "upscaling" (e.g. from feeding into the small intestine to feeding into the stomach; and/or to increase the flow rate).

The skilled person having the benefit of the present disclosure can easily provide several other obvious modifications.

FIG. 8(a) shows a first example of a raw pressure signal as can be obtained by a system according to an embodiment of the present invention, in particular a system 100, 200, 300, 400 as shown in any of FIG. 1 to FIG. 4 comprising or in cooperation with a gastric catheter such as the gastric catheters 130, 230, 330, 430 shown in FIG. 1 to FIG. 4. More details about preferred gastric catheters can be found in the "co-pending balloon application", but other suitable gastric balloon catheters (e.g. of the type to be introduced via the mouth) may also be used. In the system 200 of FIG. 2 and the system 300 of FIG. 3, two such pressure waveforms can be obtained, one for each pressure sensor. It cannot readily be seen in FIG. 8(a) whether the stomach activity is good or bad, let alone how good or how bad in a quantitative manner, hence human interpretation of the pressure signal is very difficult and highly subjective.

FIG. 8(b) and FIG. 8(c) show an example of gastric motility information extracted from the signal of FIG. 8(a), referred to herein as "short-term Gastric Balloon Motility Index" with acronym STGBMI and "long-term Gastric Balloon Motility Index" with acronym LTGBMI, respectively.

As can be appreciated from FIG. 8(b) and FIG. 8(c) a numerical value from 0.0 to 1.0, or a percentage value from 0% to 100%, or a bar diagram, or a graph showing such values at different moments in time (e.g. every 5 minutes, or every 10 minutes or every 15 minutes or every 20 minutes, or every 25 minutes, or every 30 minutes) are much easier to understand for medical personnel.

As will be described further (when discussing FIG. 13a to FIG. 13d), these short-term and long-term gastric motility-values can be automatically derived from the raw pressure signal of FIG. 8(a).

Figure 10:
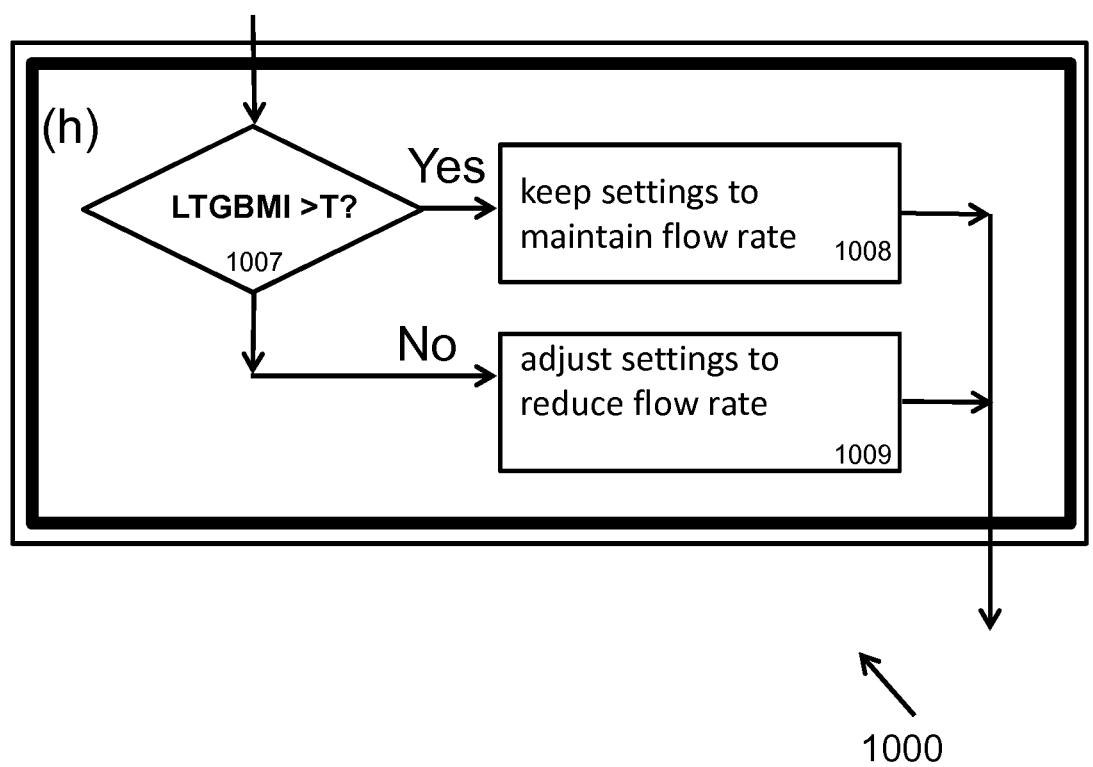
FIG. 10 to FIG. 12 are examples of routines to adjust the flow rate for feeding the patient, as can be used in step h) of FIG. 7.
Figure 11:
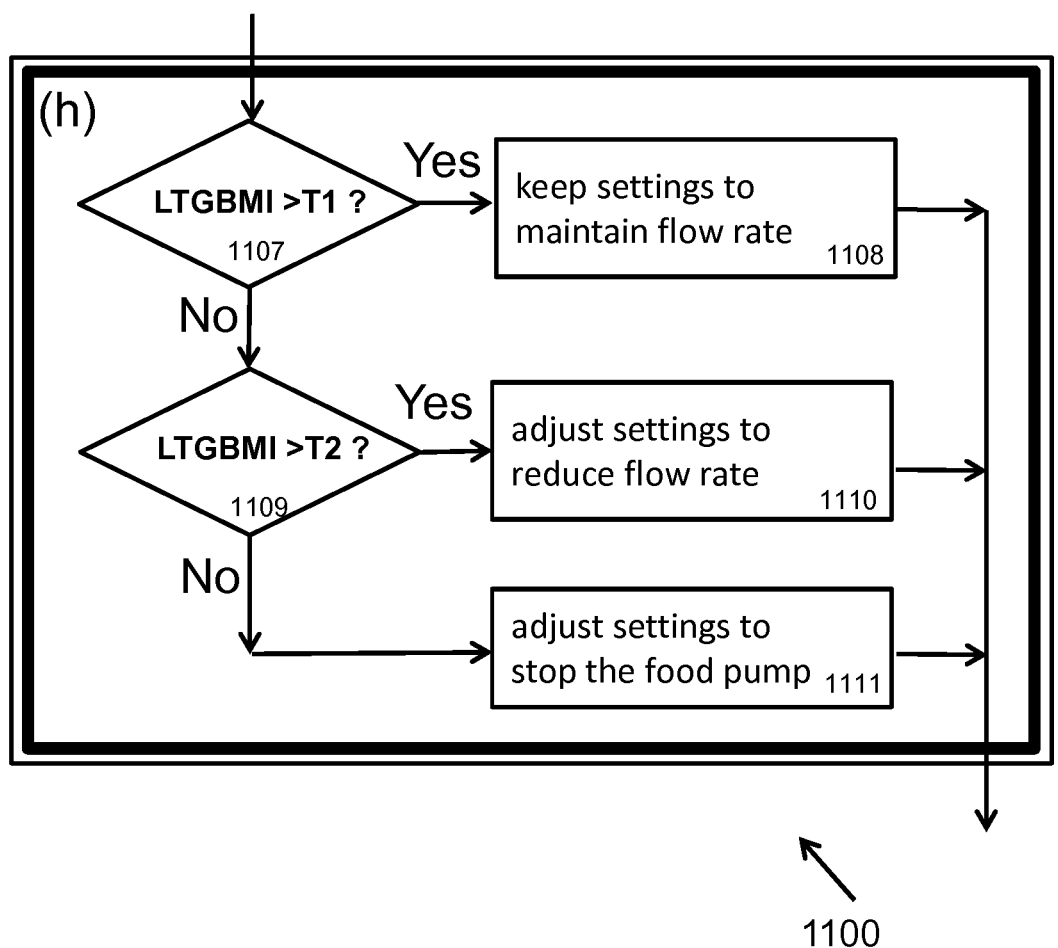
Figure 12:
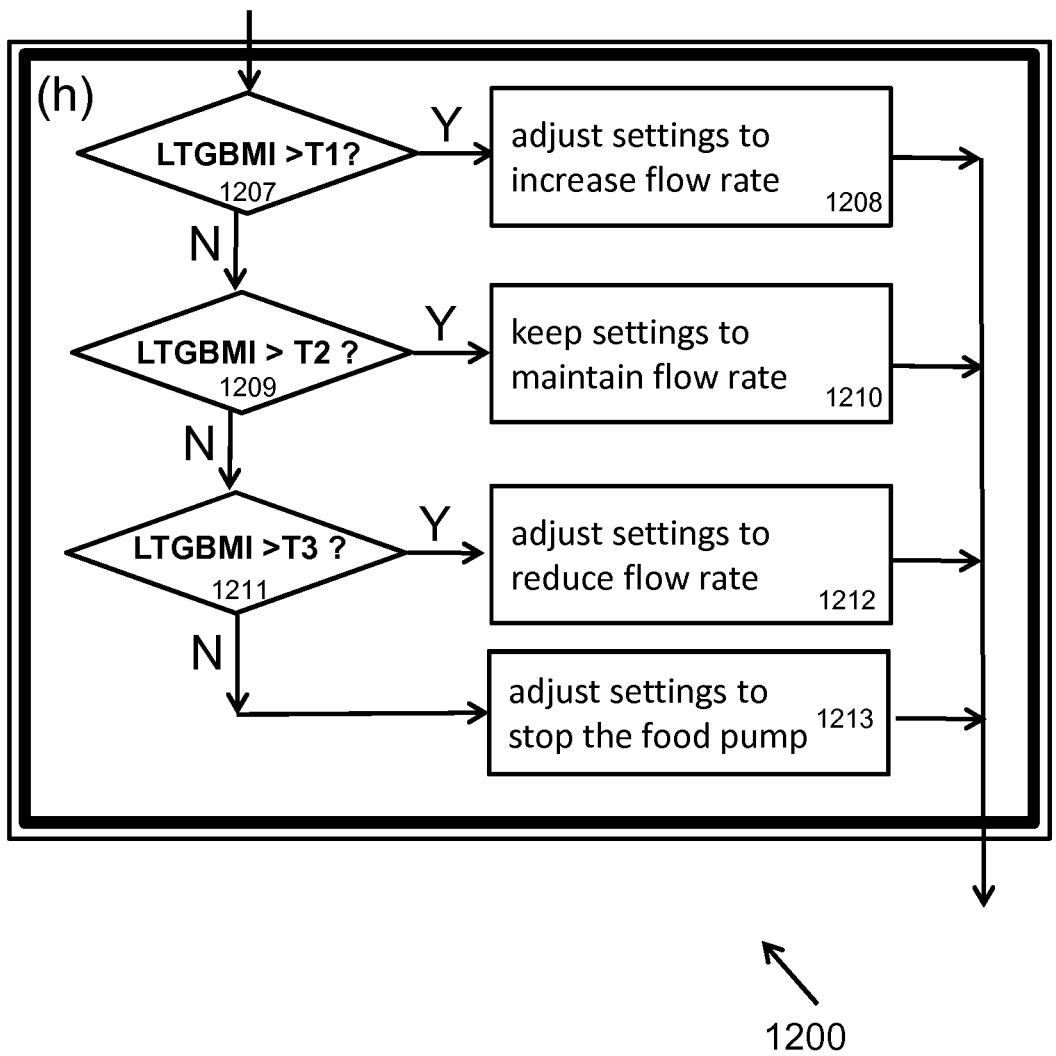

Optionally, one or more of the gastric-motility-values may be displayed together with one or more thresholds for reasons which will become clear when discussing FIG. 10 to FIG. 12. In the example of FIG. 8 two threshold values T1, T2 are shown, T1 being equal to 60% and T2 being equal to 20% in this example, but the present invention is not limited thereto, and more than two or less than two threshold values may be used, and/or other threshold values may be used.

Optionally, the gastric-motility-values are accompanied with a suggestion or warning message, e.g. depending on whether the short-term-values and/or the long-term-values are below or above certain thresholds, or within a certain threshold range (see also FIG. 10 to FIG. 12).

In the specific example of FIG. 8, the waveform of FIG. 8(a) was first filtered to remove a breathing signal and to remove short pulses related to coughing and sneezing etc. Then gastric contraction peaks were detected in the filtered waveform of FIG. 8(a) and a duration GCPD of each gastric-contraction-peak was determined. Short-term gastric-motility-values (STGBMI), e.g. as shown in FIG. 8(b) were calculated as a ratio of a cumulative duration (or sum of durations) of the gastric-contraction-peaks normalized over a first time window of 30 minutes, and long-term gastric-motility values LTGBMI, e.g. as shown in FIG. 8(c), were calculated as a maximum of these short-term-gastric-motility values STGBMI over a second time-window of 2 hours.

This algorithm will be described in FIG. 13a, and corresponds to the first branch (i) of FIG. 13d, but the present invention is not limited to this particular algorithm, and several variants of this algorithm will be described in FIG. 13b to FIG. 13d.

FIG. 13d shows an overview of various motility values, and ways of calculating them, as can be used in embodiments of the present invention. As will become clear further, the algorithm of FIG. 13a can be seen as a special case of the algorithm of FIG. 13c, in case each gastric-contraction-peak is given an equal weight, independent on the Height. Or stated differently, the algorithm of FIG. 13c can be seen as a more general case where the duration of gastric contraction peaks with a larger height can be given more weight than gastric contraction peaks with a smaller height.

Referring back to FIG. 8, in the example of FIG. 8(c), a new STGBMI value is calculated every 30 minutes, and the LTGBMI is calculated as a maximum of these STGBMI-values over the last 2 hours, but the present invention is not limited thereto, and the first time period may be shorter or longer than 30 minutes (e.g. a time period from 1 to 60 minutes, or from 2 to 55 minutes), and the second time period may be shorter or longer than 2 hours (e.g. a time period from 1 hour to 3 hours).

It is noted that in step i) of FIG. 7, the flow rate of the food pump is preferably not directly related (e.g. proportional) to the STGBMI or LTGBMI, but preferably the settings, e.g. the volume and/or the flow rate is incrementally or stepwise adjusted 708 based on the LTGBMI in step h) of FIG. 7, except for example, when the LTGBMI indicates a bad situation, in which case the food-pump can be stopped. This will be further described in FIG. 10 to FIG. 12.

In some embodiments having two balloons and having provisions for detecting the direction of the gastric contractions, the food pump may also be stopped if it is detected that the direction of the gastric contractions are in the wrong direction (towards the esophagus).

Since the food pump is controlled based on the long term motility index (LTGBMI), the calculation and/or display of the short term motility indices (STGBMI) is optional, yet it is believed that the short-term-gastric-motility values also provide interesting information about the patient. Therefore, it is preferred to show both the long-term-gastric-motility-index and a short-term-gastric-motility-index in step 704, optionally accompanied with a textual recommendation.

FIG. 9(a) shows a second example of a raw pressure signal as can be obtained by a system according to an embodiment of the present invention. FIG. 9(b) shows the short-term-gastric-motility-values (STGBMI), and FIG. 9(c)

shows the long term motility values (LTGBMI), as determined by the "first algorithm" described in FIG. 13*a*.

In the examples of FIG. 8(*b*) and FIG. 9(*b*) the system also provides the textual suggestion that it is "OK to feed" when the STGBMI is larger than the first threshold T1, but this is just an example.

FIG. 10 to FIG. 12 are examples of routines to dynamically adjust 708 the flow rate of the food pump for feeding the patient, as can be used in step h) in FIG. 7.

In step 1007 of FIG. 10 the long-term Gastric Balloon Motility Index (LTGBMI) is compared to a single threshold value T, and if the value of the LTGBMI is larger than T, (Yes-branch), the settings are kept 1008 so as to maintain the flow rate of the food pump; and if the value of LTGBMI is smaller than T (No-branch), the settings are adjusted 1009 so as to reduce the flow rate.

In a variant of FIG. 10, not only the flow-rate is reduced in step 1009, but also the (total) volume to be supplied to the patient is reduced.

In a variant of the method shown in FIG. 10, applicable to the system 200 of FIG. 2, the block 1009 may further comprise the test whether the food is being provided to the stomach via the second port P2, and if the outcome of this test is true, to stop the first food pump 212 (e.g. by setting the flow rate of the first food pump to zero), and to start the second food pump with the reduced flow rate.

In another variant of the method shown in FIG. 10, applicable to the system 400 of FIG. 4, the block 1009 may further comprise a test whether the food is being provided to the stomach via the second port P2 (i.e. that switch 452 is open and switch 451 is closed), and if the outcome of this test is true, to close the switch 452 and to open the switch 451 such that the food is no longer provided via the second port P2 into the stomach, but instead will be provided into the small intestine via the fourth port P4.

Many variants are possible, for example depending on the value of T, and/or depending on how strongly the flow rate is reduced (e.g. with 50% or with 25%), and/or whether a timing aspect is taken into account, for example choosing immediately that the food is no longer provided to the stomach but to the small intestine, or choosing this different routing only after for example 1 hour, if the long-term gastric motility-value LTGBMI is still below the threshold T.

The method 1000 is explained using an if-then statement, but can also be implemented in other ways, for example using a look-up table.

In FIG. 11 the long-term-gastric-motility index LTGBMI is compared with two threshold values T1 and T2. This method 1100 can be seen as a more sophisticated variant of the method 1000 of FIG. 10 using two threshold values instead of only one.

In step 1107 it is tested whether the LTGBMI is larger than threshold T1, and if the outcome of this test is true, the settings of the food pump are maintained in step 1108, otherwise it is tested in step 1109 whether LTGBMI is larger than T2, and if the outcome of this test is true, the settings are adjusted to reduce the flow rate of the food pump in step 1110, otherwise, the settings are adjusted to stop the food pump in step 1111. The main advantage of the method 1100 of FIG. 11 is that it allows to stop the food pump if the LTGBMI-value is below threshold T2.

The method 1100 is explained using an if-then-else statement, but can also be implemented in other ways, for example using a look-up table.

In FIG. 12 the long-term-gastric-motility index LTGBMI is compared with three threshold values T1, T2 and T3. This method 1200 can be seen as a further variant of the method of FIG. 11 using three threshold values T1, T2, T3 instead of only two threshold values T1, T2.

In step 1207 it is tested whether the LTGBMI is larger than threshold T1, and if the outcome of this test is true, the settings of the food pump are adjusted so as to increase the flow rate in step 1208, otherwise it is tested in step 1209 whether LTGBMI is larger than T2, and if the outcome of this test is true, the settings of the food pump are maintained in step 1210, otherwise it is tested in step 1211 whether the LTGBMI is larger than T3, and if the outcome of this test is true, the settings of the food pump are adjusted so as to reduce the flow rate in step 1212, otherwise the settings are adjusted to stop the food pump in step 1213.

The main advantage of the method of FIG. 12 over the method of FIG. 11 is that it allows to increase the flow rate if the LTGBMI-value is higher than T1. As described above, not all doctors may allow an increase of the flow rate, because an increase is not always safe. Therefore, practical implementations may have this feature implemented, but may request additional enabling or authorization to make this feature effective.

In a variant of the method shown in FIG. 12, applicable to the system 200 of FIG. 2, the block 1008 may further comprise a test whether the food is being provided to the small intestine via the fourth port P4, and if the outcome of this test is true, to stop the second food pump 214 (e.g. by setting the flow rate of the second food pump 218 to zero), and to start the first food pump 212 with the increased flow rate.

As can be seen, all embodiments shown in FIG. 10 to FIG. 12 have in common that if the LTGBMI-value is below a predefined threshold, the flow rate is reduced or stopped, and if the LTGBMI-value is higher than said threshold, the flow rate is maintained or increased. The methods of FIG. 10 to FIG. 12 are relatively simple implementations of step (h) of FIG. 6 and FIG. 7, also referred to herein as the "second algorithm", but more sophisticated control can also be used.

FIG. 13*a* shows a specific embodiment of an algorithm (referred to herein as "the first algorithm") for converting raw pressure data, as can be measured by the pressure sensors 114, 214, 216, 314, 316, 414 of the systems 100, 200, 300, 400 of FIG. 1 to FIG. 4, when coupled to a balloon catheter 130, 230, 330, 430, when the at least one balloon B1, B2 is inflated, and when mechanical pressure is exerted on the surface of the at least one balloon, into a value (or actually a value that changes over time), which is highly correlated with the degree of a "good working stomach".

As mentioned before, the method 1300 of FIG. 13*a* can be used to determine two gastric-motility values: a so called Short-Term Gastric Balloon Motility Index STGBMI, and a so called Long Term Gastric Balloon Motility Index LTGBMI.

In the method of FIG. 6, it would suffice to provide (e.g. display) only the STGBMI, because either there is no food pump, or there is a food pump, but it is controlled based upon instructions from the doctor (or other medical personnel).

Figure 23:
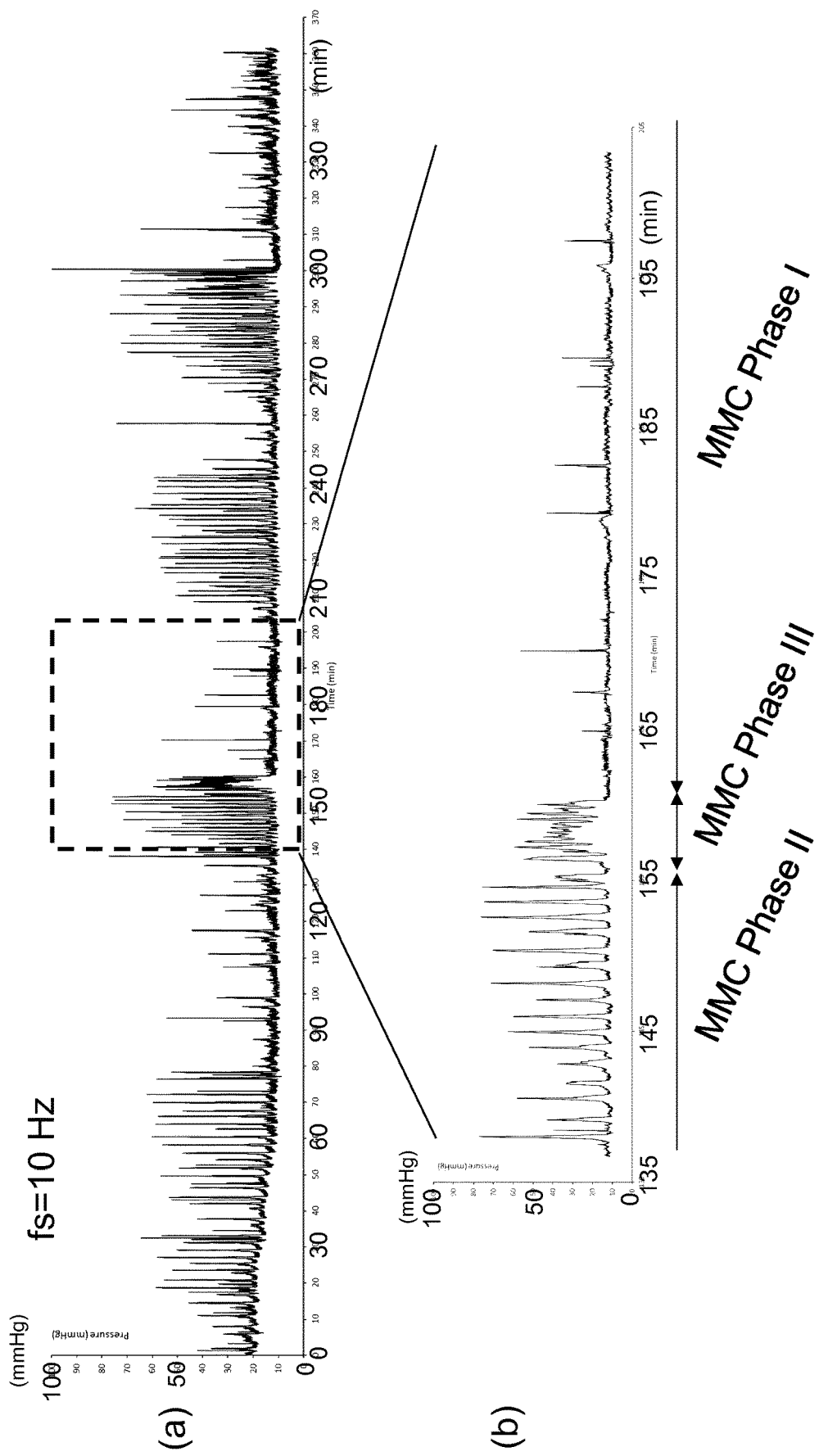
FIG. 23(a) shows an example of a raw pressure signal as can be obtained by a system according to an embodiment of the present invention. This pressure signal has a duration of about 6 hours, and was sampled at a frequency of 5 to 10 Hz.
FIG. 23(b) shows an enlarged portion thereof, with an indication of a (Migrating Motor Complex) MMC Phase I, Phase II and Phase III.

In the method of FIG. 7, the STGBMI would not be a good value to use for adjusting the settings of step h), because it is perfectly normal that a good working (empty) stomach shows no noticeable gastric contractions for a period up to 60 or even up to 110 minutes. This period is known as "MMC Phase I", and in the example of FIG. 23 it takes about 45 minutes (from T=about 160 to about 205 minutes). That is why a long-term index is calculated in step e) of FIG. 13*a*, which long-term index can indeed be used to automatically adjust the flow rate of the food pump, as one of the settings or derived settings in "loop2" of FIG. 7.

FIG. 13a shows a flow-chart of an algorithm 1300 comprising the following steps:
a) filtering 1301 the raw pressure signal 1310 (measured e.g. in step 601 or step 701). This step is intended to reduce or substantially remove at least pressure changes related to breathing, but preferably also other influences unrelated to gastric motility, such as e.g. caused by coughing, etc. Examples of possible implementations of such filtering will be discussed further in FIG. 14, FIG. 18 and FIG. 19, but the present invention is not limited to only these examples, and other or additional filtering may also be used.
b) finding 1302 "gastric contraction peaks" in the filtered pressure signal. Examples of possible implementations will be discussed further in FIG. 15 to FIG. 17 and FIG. 20, without limiting the present invention thereto.
c) determining 1303 a "peak duration" GCPD for each "gastric contraction peak" found in step b). An example of a peak duration is shown in FIG. 20. Step c) may be a separate step, or may be part of step b).
d) determining 1304 "short-term-gastric-motility-values" STGBMI as a sum of GDPD-values, normalized over a first time window TW1, for example according to the following formula:

$$\text{STGBMI} = \Sigma_{TW1}(\text{GCPD})/TW1 \quad [1]$$

where TW1 is the duration of the first time window, e.g. having a duration of 1 to 60 minutes, or 1 to 45 minutes, or 2 to 55 minutes, or 1 to 30 minutes. This value of STGBMI represents a percentage of the time during which gastric contraction peaks occurred during said first time window, or stated otherwise, as a ratio of a cumulative duration of the gastric-contraction peaks over said first time window.
e) determining 1305 "long-term-gastric-motility-values" LTGBMI based on the "short-term-gastric-motility-values", for example as a maximum of a plurality of STGBMI-values over a second time window TW2 having a duration of 1 hour to 3 hour, e.g. equal to about 2 hours. This can be expressed in mathematical form as:

$$\text{LTGBMI} = \max_{TW2}(\text{STGBMI}) \quad [2]$$

An example hereof is already shown in FIG. 8(c) and FIG. 9(c), where the LTGBMI is calculated as a maximum of the STGBMI-signal over a predefined time interval of 2 hours, but the present invention is not limited thereto, and another time-interval TW2 larger than 2 hours, or smaller than 2 hours can also be used, for example a duration from 1 hour to 3 hours, or from 1.5 hours to 2.5 hours.

Preferably the algorithm 1300 of FIG. 13a further comprises the following step:
f) determining 1306 a "pressure amplitude related to breathing", also referred to herein as "breathing amplitude" Abr. It is rather strange that the amplitude relating to breathing is first determined, and subsequently filtered away, which makes it not-trivial. The main advantage hereof is that the breathing amplitude Abr can be used to determine a minimum height value "Hmin" for qualifying a peak as a gastric contraction peak, according to the following formula or an equivalent formula:

$$\text{Hmin} = K*\text{Abr} \quad [3]$$

where K is a predefined value in the range from 0.5 to 5.0, or in the range from 0.7 to 3.0, or in the range from 0.70 to 2.50, or in the range from 0.70 to 0.95 or in the range from 1.05 to 5.0, for example equal to about 0.75, or about 0.80 or about 0.85 or about 0.90 or about 0.95, or about 1.0, or about 1.05, or about 1.1, or about 1.15, or about 1.2 or about 1.25 (=5/4) or about 1.3 or about 1.33 (=4/3) or about 1.4 or about 1.5 (=3/2) or about 1.6 or about 1.66 (=5/3) or about 1.7 or about 1.75 (=7/8) or about 1.8 or about 1.9, or about 2.0 or about 2.1 or about 2.2 or about 2.3 or about 2.5 or about 3.0 or about 3.5 or about 4.0 or about 4.5 or about 5.0.

Tests have shown that it is very difficult to choose a fixed value for the minimum peak height Hmin (for qualifying a peak as a valid gastric contraction peak) that works well for every individual, but that choosing the minimum peak height proportional to the breathing amplitude works surprisingly well, probably because it automatically takes into account several anatomical aspects of the particular individual.

In the example shown in FIG. 13a, a new STGBMI-value is provided periodically at a first update-frequency, for example once every 5 minutes, and a new LTGBMI-value is provided periodically at a second update frequency, for example once every 30 minutes, but other update frequencies can also be used. The first update period (at which STGBMI-values are provided) may be smaller than or equal to the first time window (e.g. 5 minutes and 30 minutes respectively). The second update period (at which LTGBMI-values are updated) may be smaller than or equal to the second time window (e.g. 30 minutes and 2 hours respectively). This is also true for other embodiments.

It is noted that the algorithm of FIG. 13a corresponds to the first branch (i) of FIG. 13d.

FIG. 13b shows a flow-chart of a method 1350 according to another embodiment of the "first algorithm", which can be used for extracting long-term-gastric-motility information LTGBMI and optionally also short-term-gastric-motility information from raw pressure data as can be measured by the systems 100, 200, 300, 400 of FIG. 1 to FIG. 4, when coupled to a balloon catheter.

The method 1350 of FIG. 13b is a variant of the method 1300 of FIG. 13a, where step a) and b) and optional step f) are identical to those of FIG. 13a, but step c) to e) are different.

More specifically, the method 1350 of FIG. 13b comprises a first variant (indicated by ii), comprising the following steps:
a) filtering 1301 the raw pressure signal 1310, in order to reduce or remove pressure changes unrelated to gastric motility, such as e.g. pressure changes caused by breathing;
b) finding 1302 "gastric contraction peaks" in the filtered pressure signal;
c) determining 1353 a height H of each of said gastric contraction peaks, and assigning a gastric activity value GAV defined as a function w(H) of said height H to each gastric contraction peak. The peak height H can be defined for example as illustrated in FIG. 20, but variants hereof are also possible. The function w(H) is referred to herein as "weighting function" or fraction, and can be written as:

$$w(H) \quad [4]$$

In a preferred embodiment, the result of this function is a value in the range from 0.0 to 1.0 depending on the peak height as will be described further in FIG. 13e and FIG. 13f.

In the first variant, step d) can be omitted.
e) determining 1355 a long-term-gastric-motility-value LTGBMI as a maximum of a plurality of said GAV-values, the maximum being taken over a second time window of 1 hours to 3 hours (e.g. 2 hours), or written in mathematical form:

$$\text{LTGBMI} = \max\nolimits_{TW2}(\text{GAV}) \quad [5]$$

where $\max_{TW2}(\ )$ means a maximum over the second time window.

While not absolutely required for driving the food pump, the method 1350 may further comprise step d) of calculating a short term motility value STGBMI for visualization purposes, which value can be calculated as a function of a plurality of GAV-values over a first time window, for example as a statistical function (e.g. an average or a median) of a plurality of GAV-values over a first time window TW1 of 1 to 60 minutes, or 2 to 55 minutes, or 5 to 45 minutes, e.g. equal to 30 minutes. This can be written in mathematical form as:

$$\text{STGBMI} = \text{AVG}_{TW1}(\text{GAV}) \quad [6]$$

In another specific implementation, the statistical function is a median over the first time-window TW1 of 1 to 60 minutes, or 2 to 55 minutes, or 5 to 45 minutes, e.g. equal to 30 minutes, written as:

$$\text{STGBMI} = \text{Median}_{TW1}(\text{GAV}) \quad [7]$$

Like the method 1300 of FIG. 13*a*, the method 1350 of FIG. 13*b* preferably further comprises step f) of determining 1306 a "pressure amplitude related to breathing", also referred to herein as "breathing amplitude" Abr, and preferably this breathing amplitude Abr is used in step b) of finding the gastric contraction peaks (e.g. by dynamically defining the minimum peak height to qualify as a gastric contraction peak). The breathing amplitude may also be used to filter the raw pressure signal.

The values of STGBMI in branch (ii) of FIG. 13*b* are only indicative of the peak height, not of the peak duration, and will usually be different from the values obtained from the algorithm of FIG. 13*a*.

FIG. 13*b* also shows a method 1360, indicated by branch (iii) on the right side of FIG. 13*b*. The steps a), b), c) and d) are identical to those of the method 1350 described above, but now step d) is mandatory. Step e) is different, in that the long-term gastric motility value LTGBMI is calculated 1365 as the maximum value of the short-term-gastric motility values, over the second time period TW2 of about 1 to 3 hours, or 1.5 to 3.0 hours, or 1.5 to 2.5 hours. This can be written as follows:

$$\text{LTGBMI} = \max\nolimits_{TW2}(\text{STGBMI}) \quad [8]$$

The method 1360 may further comprise step f), as described above. The algorithms 1350 and 1360 are schematically indicated in FIG. 13*d* as branch (ii) and (iii) respectively.

FIG. 13*c* shows a flow-chart of a method 1380 according to another embodiment of the "first algorithm", which can be used for extracting short-term-gastric-motility information STGBMI and long-term-gastric-motility information LTGBMI from raw pressure data, as can be measured by the systems 100, 200, 300, 400 of FIG. 1 to FIG. 4, when coupled to a balloon catheter.

The method 1380 of FIG. 13*c* can be seen as a variant of the method 1300 of FIG. 13*a* or as a variant of the method 1360 of FIG. 13*b*, where step c) to e) are different but steps a), b) and f) may be identical.

More specifically, the method 1380 of FIG. 13*c* comprises the following steps:

a) filtering 1301 the raw pressure signal 1310, in order to reduce or remove pressure changes unrelated to gastric motility, such as e.g. pressure changes caused by breathing;

b) finding 1302 "gastric contraction peaks" in the filtered pressure signal;

c) determining 1383 a duration GCPD and a peak height H of each gastric contraction peak GCP, and assigning a fraction of the duration, using a weighting function w(H) of the height H, as Gastric Activity Value GAV to each gastric contraction peak GCP. In a preferred embodiment, the function is the product of the gastric peak duration GCPD and the weight value w(H), which can be expressed in mathematical form as:

$$\text{GAV} = \text{GCPD} * w(H) \quad [9]$$

where GCPD is the gastric contraction peak duration, H is the peak height, and w(H) is a weighting function of the height (also referred to herein as "fraction").

d) calculating 1384 a short term motility value STGBMI as a sum or as a cumulative value of a plurality of GAV-values over a first time window of 1 to 60 minutes, e.g. 2 to 55 minutes, or 5 to 45 minutes, e.g. equal to 30 minutes, normalized to said first time window TW1. This can be expressed in mathematical form as:

$$\text{STGBMI} = \Sigma_{TW1}(\text{GAV})/\text{TW1} \quad [10]$$

or, if calculated directly from the peak durations and heights, as follows:

$$\text{STGBMI} = \Sigma_{TW1}[\text{GCPD}*w(H)]/\text{TW1} \quad [11]$$

e) determining 1385 a long-term-gastric-motility-value LTGBMI as a maximum of a plurality of said STGBMI-values, the maximum being taken over a second time window TW2 of 1 hours to 3 hours, or 1.5 to 3 hours, or 1.5 to 2.5 hours, e.g. equal to about 2 hours, or written in mathematical form:

$$\text{LTGBMI} = \max\nolimits_{TW2}(\text{STGBMI}) \quad [12]$$

where $\max_{TW2}(\ )$ means a maximum over the second time window TW2.

For completeness, the method 1380 may further comprise step f) of determining 1306 a "pressure amplitude related to breathing", similar as described above.

FIG. 13*a*, the two variants of FIG. 13*b*, and FIG. 13*c* are four examples of possible implementations of the "first algorithm", but the present invention is not limited thereto, and other embodiments are also envisioned, as illustrated in FIG. 13*d*.

FIG. 13*d* is a schematic representation of steps a) to f) of envisioned embodiments of the "first algorithm", comprising inter alia the methods of FIG. 13*a*, FIG. 13*b* and FIG. 13*c*, but not limited thereto. As can be seen, all embodiments have step a) b) and c) and optional step f). Step c) comes in several flavours, depending on whether the peak duration, the peak height, or both the peak duration and the peak height are used to calculate the gastric activity values GAV. Steps d) is present in branches (i), (iii) and (iv), but is optional in branch (ii). In all cases, the LTGBMI is calculated as a maximum value over the second time-window of 1 to 3 hours. FIG. 13*d* clearly shows that embodiments of branch (i) are a special case of embodiments of branch (iv), in case the weighting function is equal to 1.0 for all gastric contraction peaks.

Figure 13E:
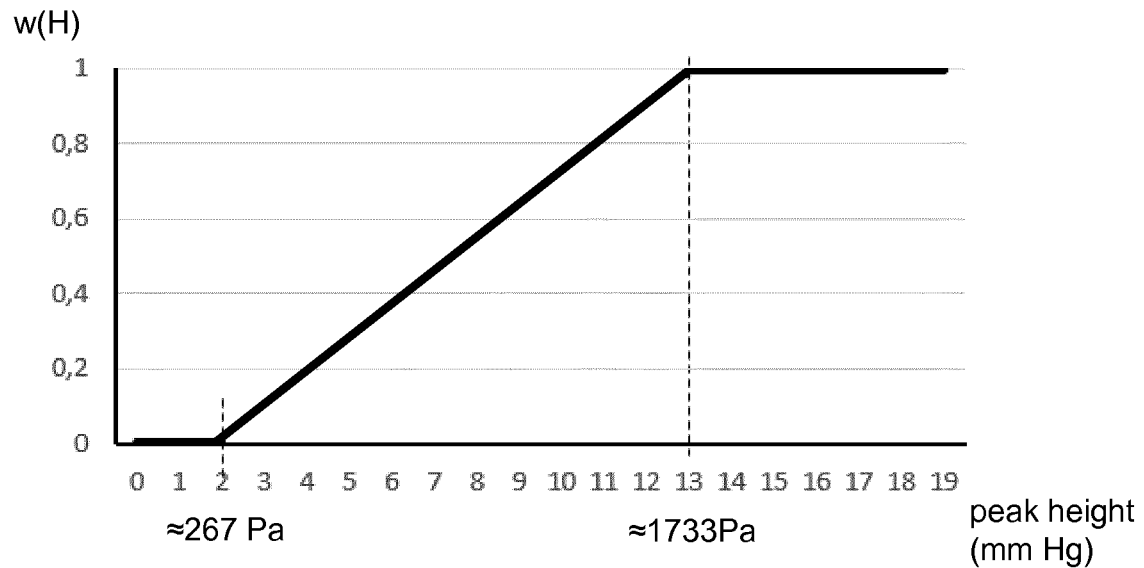
FIG. 13e and FIG. 13f show two exemplary weight functions (or "fraction function") as can be used in certain embodiments of the present invention, for example in the algorithm of FIG. 13b, FIG. 13c and FIG. 13d.

FIG. 13*e* shows an exemplary weight function which can be used to determine a weight factor for a given "height"- value. As can be seen, this weight function is a piece-wise-linear function having three line segments. The weight factor W is zero if the peak-height is smaller than a first predefined pressure value (in the example chosen as 2 mm Hg, or about 267 Pa), and the weight factor W is one if the peak-height is larger than a second predefined pressure value (in the example chosen as 13 mmHg, or about 1733 Pa), and is a value between 0.0 and 1.0 for peak-heights between the first and second pressure value.

But of course, the present invention is not limited to this particular example, and the first pressure value (also referred to herein as "relatively weak pressure value") can for example be a value in the range from 100 to 700 Pa, or in the range from 200 to 600 Pa, for example equal to about 400 Pa. The second pressure value (also referred to herein as "relatively strong pressure value") can for example be a value in the range from 1000 to 3000 Pa, or in the range from 1300 to 2500 Pa, or in the range from 1750 to 2500 Pa, for example equal to about 1750 Pa or about 2000 Pa or about 2250 Pa. And weight functions with more than three line segments, for example with four or five line segments, or weight functions with a non-linear curve, for example with a second order or third order polynomial curve can also be used.

Embodiments using a weight function may provide slightly better results than embodiments not using a weight function, because it was found that completely ignoring the height of gastric-contraction-peaks is not ideal. While it is true that the gastric-contraction peaks having a peak height above a relatively high pressure value (e.g. the above mentioned second predefined pressure of about 1733 Pa) can be considered as "equally good", and gastric contraction peaks having a peak height smaller than a relatively low pressure value (e.g. the above mentioned first predefined pressure of about 267 Pa) are to be considered as "equally bad" or "insignificant", it was found that more accurate results can be achieved by assigning a larger weight factor to peaks having a height closer to said second pressure value, and by assigning a lower weight factor to peaks having a height closer to said first pressure value, as this better reflects good or bad working of the stomach.

Figure 13F:
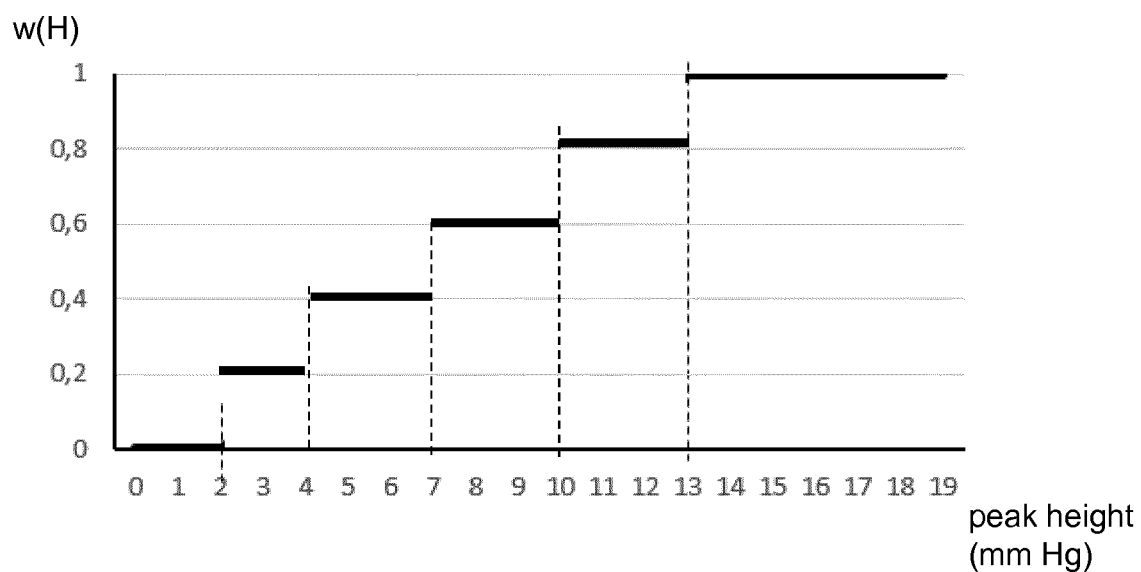

FIG. 13f show another exemplary weight function (or "fraction function") as can be used in embodiments of the present invention, to illustrate that the weight function need not be a continuous function. As can be appreciated from FIG. 13e and FIG. 13g, the shape of the weighting function is not critical for the invention, and skilled persons having the benefit of the present disclosure can easily find other weighting functions.

FIG. 14 shows an example of several "filtering" techniques as can be used in step a) of FIG. 13a to FIG. 13d. Indeed, the balloon pressure signal as measured by the pressure sensor is typically influenced by various physiological processes such as breathing, abdominal pressure, heart rate, physical movement, gagging, coughing, sneezing and gastric motility. Various filters can be used to reduce or preferably completely remove influences other than gastric motility-induced pressure changes. Several techniques can be used, for example filtering in the time domain, and/or filtering in the frequency domain.

Figure 18:
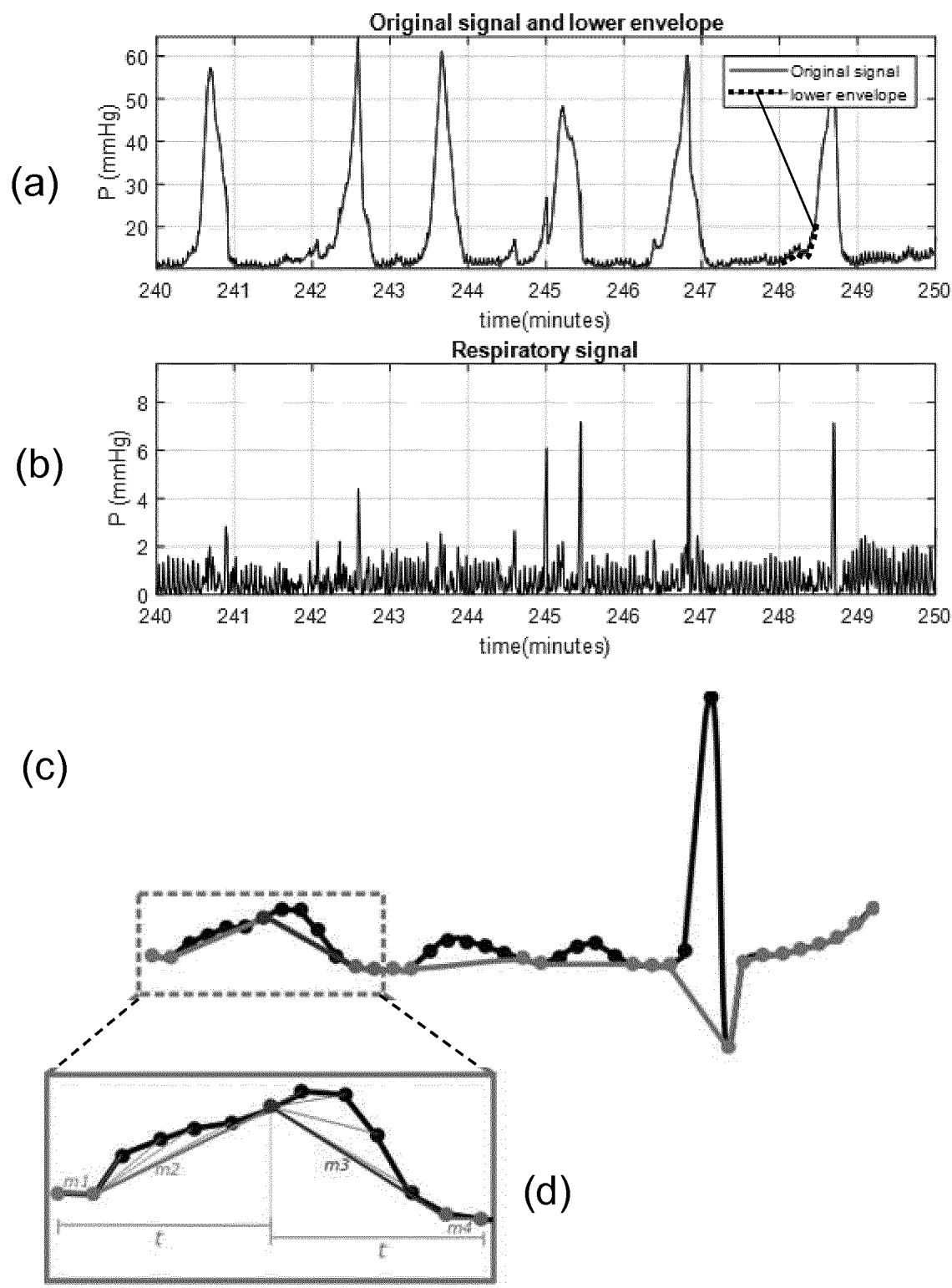
FIG. 18 illustrates an algorithm for determining a breathing amplitude, as may be used in step f) of FIG. 13a to FIG. 13d, which amplitude can then be used for reducing or substantially removing the influence of breathing from the raw pressure signal in step a), and/or for determining a minimum peak height to qualify as a gastric contraction peaks in step c).

In FIG. 18 a possible implementation to remove signal ripple in the pressure signal related to breathing (which ripple is typically relatively small), will be described in more detail.

Figure 19:
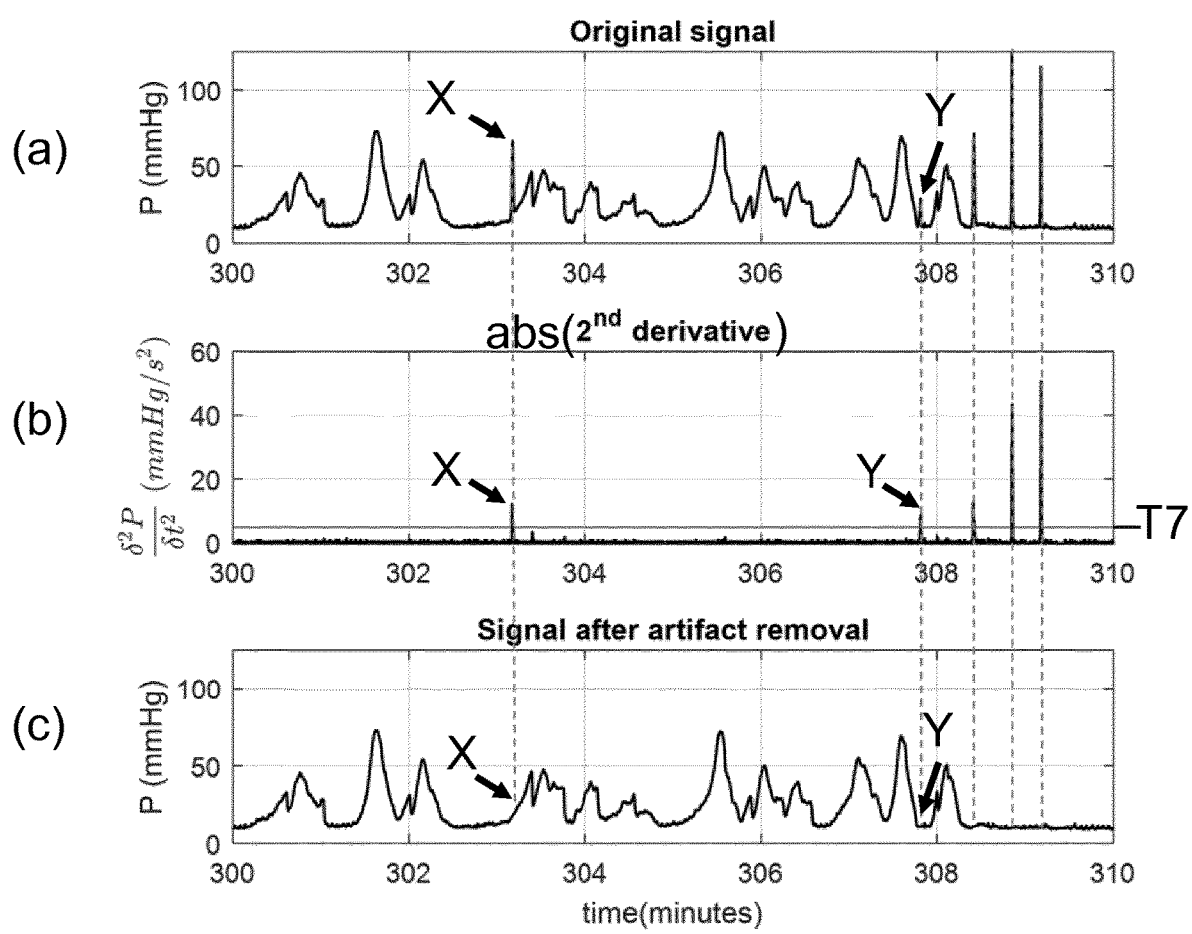
FIG. 19 illustrates an example how certain artefacts can be removed from a raw pressure signal.
Figure 20:
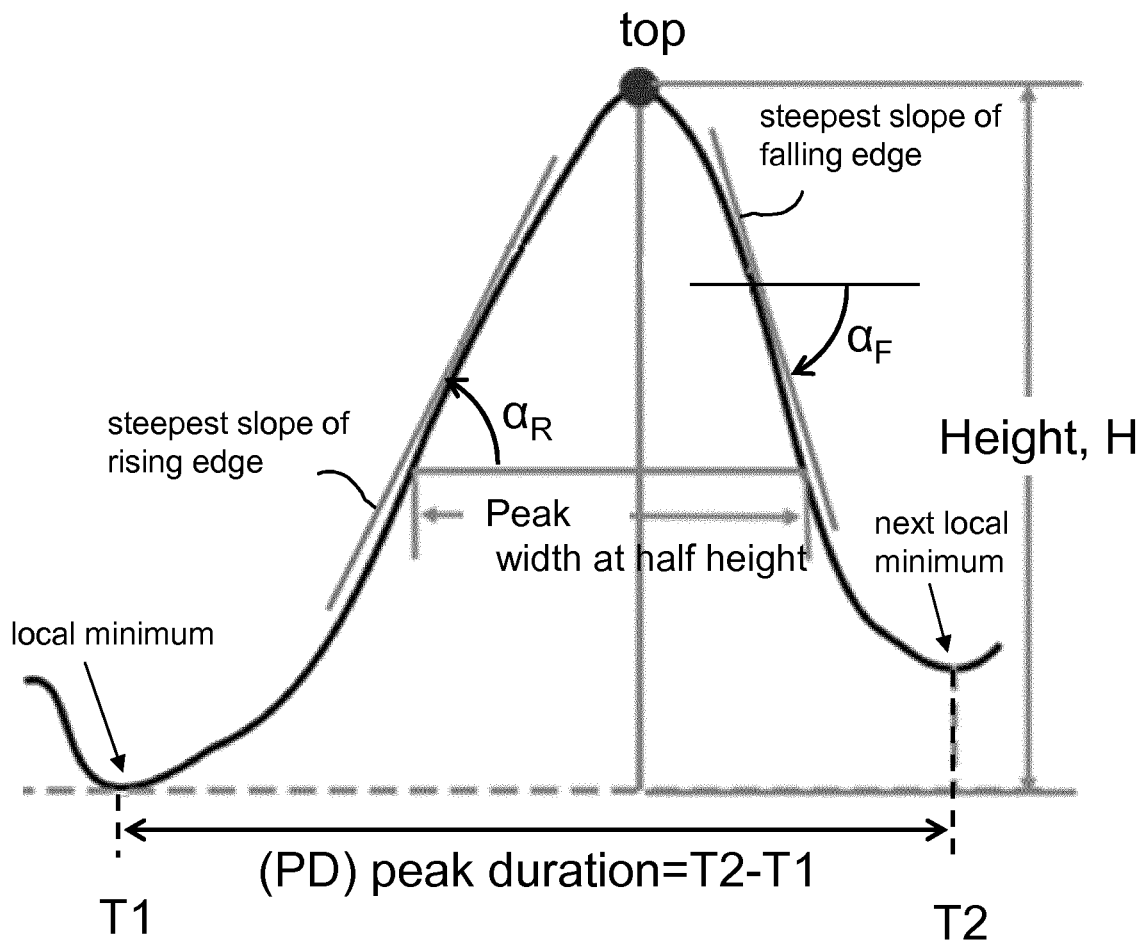
FIG. 20 shows an exemplary peak waveform as may be encountered in the raw pressure signal, and shows some characteristics of this peak which can be taken into account for evaluating whether this peak qualifies as a valid Gastric Contraction Peak, and which can be used for determining (e.g. calculating) a gastric activity value (GAV) associated with this peak.

In FIG. 19 a possible implementation to remove peaks related to coughing, sneezing, hiccups, etc. (which are typically relatively large) will be described in more detail.

Preferably, the filtering 1301 also comprises low-pass filtering or smoothing, preferably performed after the removing of the breathing signal, and after removal of the peaks related to coughing etc. In an embodiment, a Butterworth filter is used, but other low-pass filters may also be used, such as for example a Chebyshev filter, or an elliptic filter.

It is pointed out however that the present invention is not limited to these specific filters, and that other or additional filtering techniques may also be used, provided that no significant gastric contraction information is lost, and that no significant errors are introduced into the signal, which may lead to misinterpretation of the gastric contraction peaks.

While "filtering"-techniques per se are known in the art, it turned out not to be a trivial task to find a good working filter. But now that the pitfalls are known, and a working solution has been found, the skilled person having the benefit of the present disclosure, can easily find other solutions.

Figure 15:
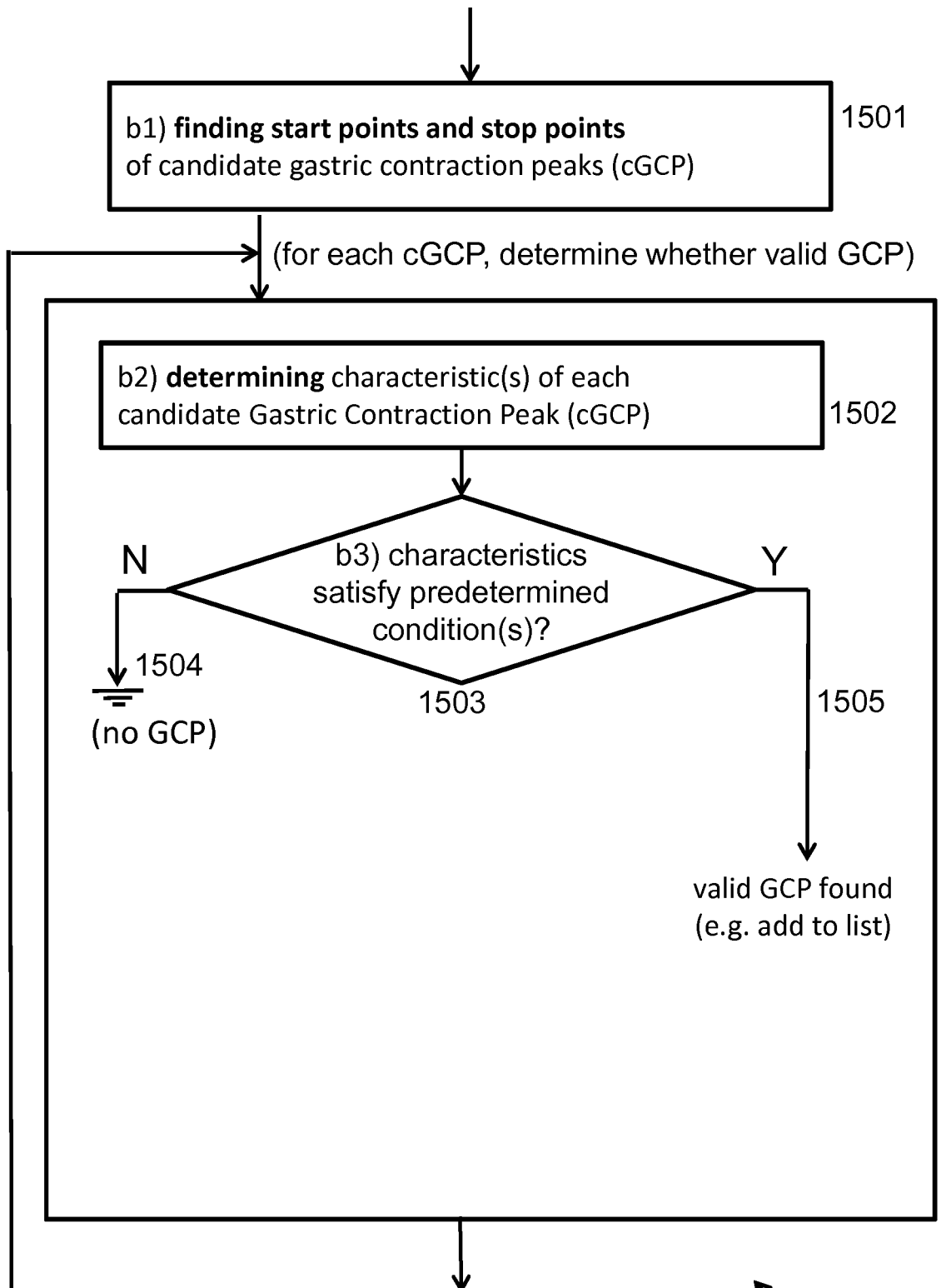
FIG. 15 shows a first example of an algorithm for "finding Gastric Contraction Peaks", as can be used in step b) of FIG. 13a to FIG. 13d.

FIG. 15 shows a first example of an algorithm for "finding Gastric Contraction Peaks", as can be used in step b) of FIG. 13a to FIG. 13d. In order to better understand the underlying problem and the solution proposed by the procedure of FIG. 15, the reader is referred to the exemplary pressure signal of FIG. 23(a) and FIG. 23(b), and to the exemplary waveform of FIG. 20. The inventors came to the idea of taking a two-step approach, where in a first step peaks of any kind (referred to herein as "candidate gastric contraction peaks" abbreviated as cGCP's) are located, and where in a second step it is determined whether the cGCPeak is an actual gastric contraction peak GCP, or not.

The method of FIG. 15 comprises the following steps:
b1) finding 1501 start points and stop points of candidate gastric contraction peaks (cGCP's);
b2) determining 1502 at least one characteristic of the waveform of each candidate gastric contraction peak;
b3) testing 1503 whether said at least one characteristic satisfies a predetermined condition (or set of conditions), and if an outcome of this test is true, considering 1505 this candidate gastric contraction peak as a valid gastric contraction peak, and if the outcome of the test is false, discarding 1504 this candidate gastric contraction peak (e.g. by not taking its peak duration and/or its height into account in the calculation of the short-term and long-term motility values STGBMI, LTGBMI values.

The method of FIG. 15 can be implemented in several ways, two more detailed examples will be described next, but the present invention is not limited hereto.

In a first example, illustrated in FIG. 20, step b1) comprises: finding local minima of the filtered pressure signal, and considering each waveform between consecutive local minima as a candidate gastric contraction peak, and considering the time between these minima as the "peak duration"; and step b2) comprises: finding a minimum pressure and finding a maximum pressure of the candidate gastric contraction peak between the local minima, and considering a difference between the maximum pressure and the minimum pressure as the height H of the candidate gastric contraction peak; and step b3) comprises: testing whether said height H is larger than a given height value Hmin and testing whether said peak duration is a value in a predefined range, e.g. in the range from 10 to 80 seconds.

Figure 21:
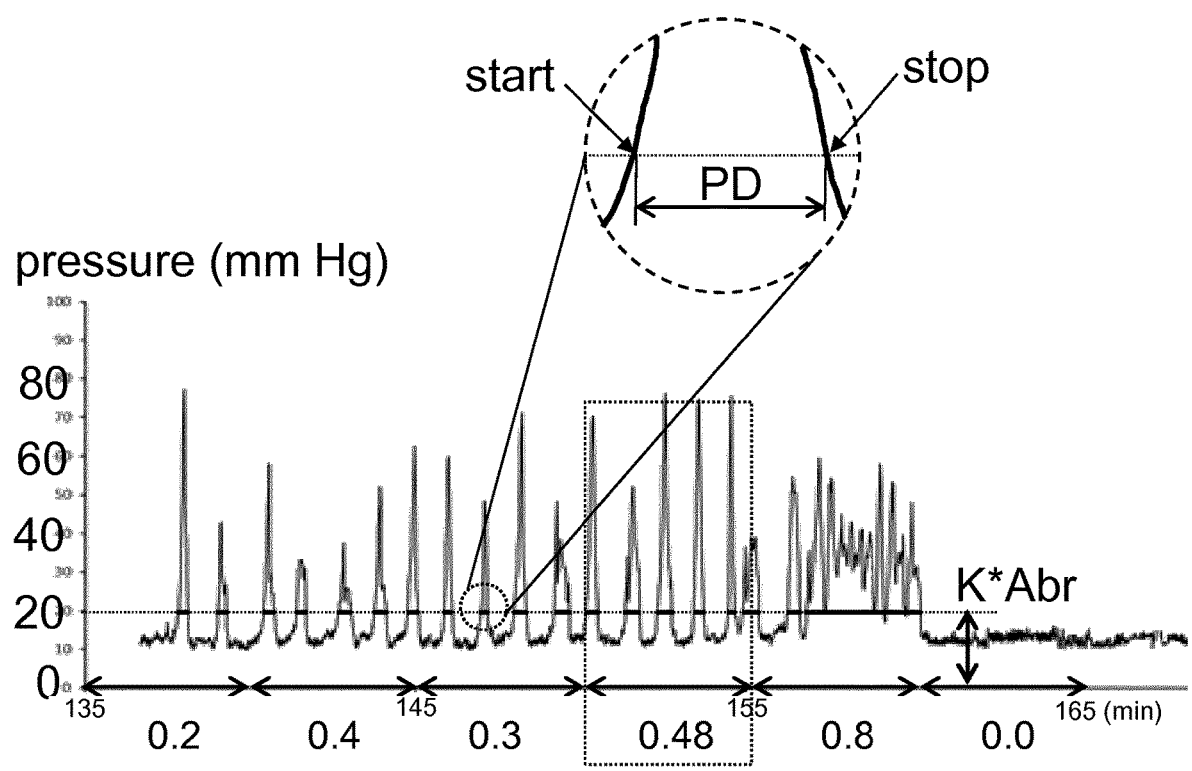
FIG. 21 shows an exemplary waveform having peaks, and a possible definition of start and end points of said peak.

In a second example, illustrated in FIG. 20 and FIG. 21, step b1) comprises: finding local minima of the filtered pressure signal, and considering each waveform between consecutive local minima as a candidate gastric contraction peak, and considering the pressure difference between the lowest local minimum and the top as the peak height (H); and step b2) comprises: finding a minimum height (Hmin) as a function of the breathing amplitude (Abr), for example a local breathing amplitude, for example in a range from ±1 to ±7 minutes around the peak, for example according to the function: Hmin=K*Abr, where K is a predefined constant; and step b3) comprises: testing whether the peak height H is larger than Hmin.

In another example, illustrated in FIG. 21, step b1) comprises finding a start point at a crossing of a rising edge of the filtered pressure signal and a given height value "Hmin", and finding a stop point at a crossing of a falling edge of the filtered pressure signal and the given height value "Hmin", and considering each waveform between said start point and said stop point as a candidate gastric contraction peak cGCP, and considering the time between the start point and the stop point as the peak duration PD; and step b2) comprises: finding a minimum pressure and finding a maximum pressure of the candidate gastric contraction peak between the start point and the stop point, and considering a difference between the maximum pressure and the minimum pressure as the height H of the candidate gastric contraction peak; and step b3) comprises: testing whether said pulse duration is a value in a predefined range, e.g. in the range from 10 to 80 seconds.

Figure 16:
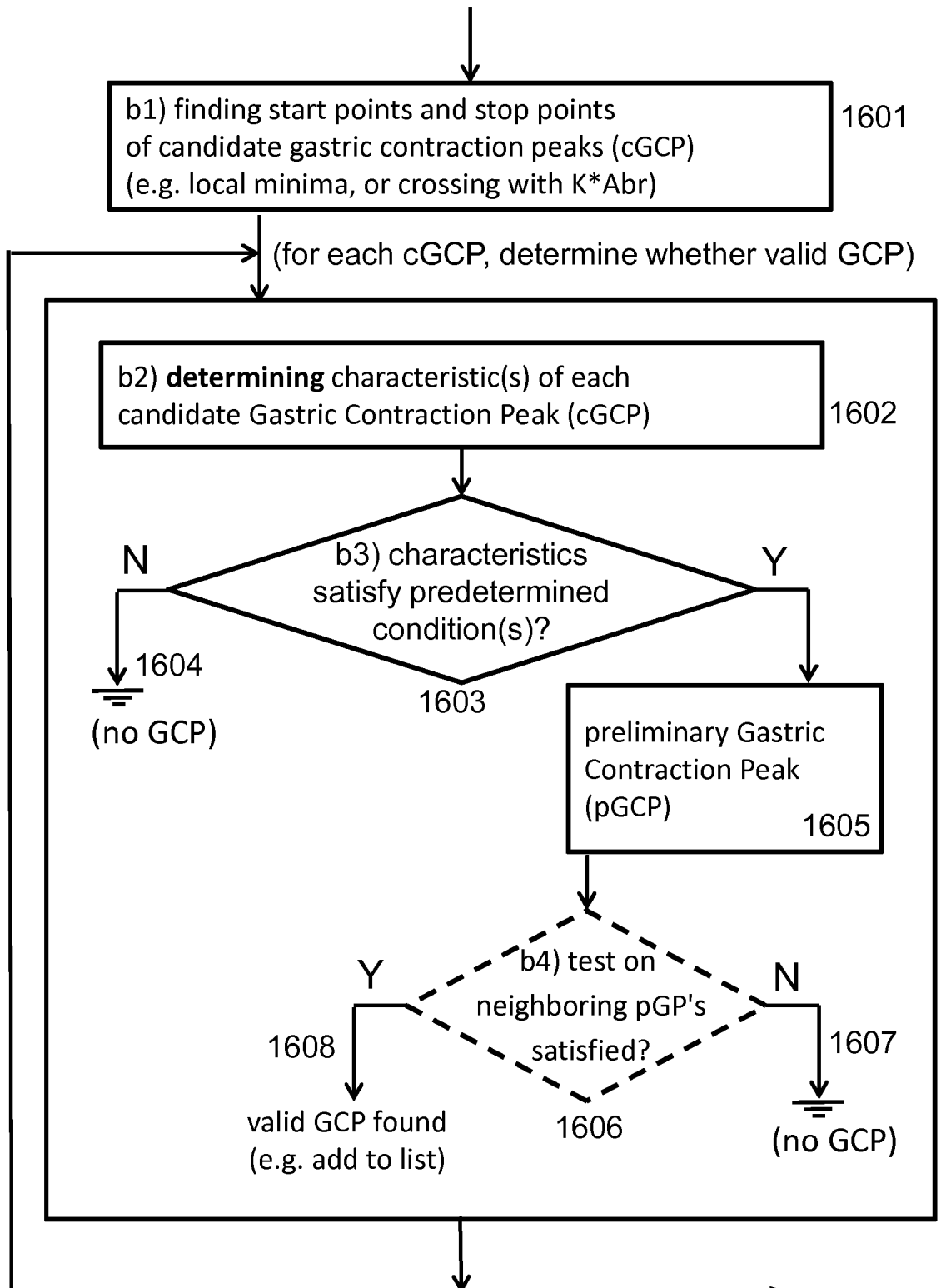
FIG. 16 shows an optional further improvement of the method of FIG. 15, by the addition of a post-processing step.

FIG. 16 shows a possible further improvement of the method 1500 of FIG. 15, by the addition of a post-processing step in the Yes-branch 1505 of FIG. 5. In the method 1600, step b3) comprises: testing 1603 whether said at least one characteristic satisfies a predetermined condition (or set of conditions), and if an outcome of this test is true, considering 1605 this candidate gastric contraction peak cGCP as a preliminary gastric contraction peak; and the algorithm further comprises step b4) of testing 1606 whether recently considered preliminary gastric contraction peaks satisfy a predetermined condition (or set of conditions), and if an outcome of this test is true, to consider 1608 the recently found preliminary gastric contraction peaks as real or valid gastric contraction peaks, and if the outcome of this test is false, to consider 1607 at least one of the recently found preliminary gastric contraction peaks to be invalid. In the latter case, recently added preliminary GCP's may be re-evaluated, and one or more pGCP's with a lower likelihood of being a real GCP may be discarded, e.g. based on how far the characteristics of said pGCP is removed from the boundary. In a particular embodiment, the pGCP with the lowest height is discarded. In another embodiment, the pGCP with the smallest surface under the curve is discarded. But the skilled person having the benefit of the present disclosure can easily find other alternatives.

FIG. 17 shows examples of characteristics that may be used in step b3) of FIG. 15 and FIG. 16 to evaluate whether the peak qualifies as a valid Gastric Contraction Peak. Most of these characteristics are shown in FIG. 20. Any one or more of the tests 1701 to 1706 shown in FIG. 17 can be used in the test of step b3) of FIG. 15 and FIG. 16.

Test 1703 and 1704 may comprise that the absolute value of the steepest rising slope and steepest falling slope should be a value in a predefined range, e.g. from 0.04 mmHg/s to 25 mmHg/s, in order to qualify as a gastric contraction peak, that is from about 5.3 Pa/s to about 3.3 kPa/s.

The criterion 1706, related to the "distance between two gastric contraction peaks" can for example be implemented as follows: it is tested whether the distance between two neighbouring Gastric Contraction Peaks is smaller than a predefined minimum distance, and if the outcome of this test is true, one of the peaks is preserved and the other is discarded. In an embodiment, the highest peak is preserved and the smaller peak is discarded.

FIG. 18 illustrates an algorithm for detecting the breathing amplitude Abr in the raw pressure signal, as may be used in step f) of FIG. 13*a* to FIG. 13*d*, but the same algorithm (or a portion thereof) can also be used for reducing or removing the breathing signal in step a) of FIG. 13*a* to FIG. 13*d*.

FIG. 18(*a*) shows an exemplary raw pressure signal, and a "lower envelope signal" which is used as a kind of baseline signal. In FIG. 18(*a*) the original pressure signal and the "lower envelope signal" seem to coincide (due to the scaling of the drawing), but the difference becomes more clear in FIG. 18(*c*) and FIG. 18(*d*).

FIG. 18(*b*) shows the signal obtained by subtracting the original pressure signal and the lower envelope signal. The difference signal is referred to herein as the "respiratory signal" or the "breathing signal", even though in reality it is only an approximation thereof, but the approximation is good enough for the purposes of the present invention, namely to extract a breathing amplitude Abr, and to filter out this signal without significantly influencing the gastric peak information.

FIG. 18(*c*) and FIG. 18(*d*) illustrate the lower envelope technique in more detail. In this example, a secant technique is used to find the segment with the lowest slope within a window of a given length, but the present invention is not limited thereto, and other techniques can be used as well.

While the technique shown in FIG. 18 allows to provide the approximate breathing signal of FIG. 18(*b*), it also provides a small amount of relatively high peaks (see FIG. 18*b*), which are considered as artefacts or outliers of the breathing signal.

The value of the "breathing amplitude" Abr can for example be calculated using (1) a median filter that rejects 25% of the smallest values and 25% of the highest values, and keeps the other 50% of the values in between, and using (2) an averaging filter that calculates the average of the remaining 50% of values. The breathing amplitude Abr is preferably calculated over a time-window of about 1 to 15 minutes.

Removing the breathing signal from the raw pressure signal can be implemented by subtracting the "breathing signal" of FIG. 18(*b*) from the raw pressure signal of FIG. 18(*a*), and optionally correcting for potential signal dips caused by the peaks in FIG. 18(*b*), which can easily be recognized as outliers of the breathing signal, for example by searching for peaks in the signal of FIG. 18(*b*) having an amplitude larger than a predefined value (e.g. value=Abr*1.95), and by considering them as outliers.

In the example shown in FIG. 18, both the determination of the breathing amplitude Abr, and the removal of the breathing signal from the raw pressure signal are performed in the time domain, but the invention is not limited thereto, and one or both of these steps may also be performed in the frequency domain, for example by using a band-pass filter to determine the breathing amplitude Abr, and/or by using a band-rejection filter to filter out the breathing signal.

A skilled person having the benefit of the present disclosure, can easily find alternative techniques for obtaining the breathing amplitude Abr and/or for filtering out the breathing signal from the raw pressure data.

FIG. 19 illustrates by way of an example, how some "short and intense" artefacts, for example related to coughing or sneezing, can be detected and can be removed from the pressure signal.

FIG. 19(*a*) shows an exemplary raw pressure signal with five such short and intense peaks, two of which are labelled with the letters X and Y for illustrative purposes.

FIG. 19(*b*) shows the absolute value of the second derivative of the pressure signal of FIG. 19(*a*) versus time. As can be seen, the locations of the "short and intense artefacts" in the original signal substantially coincide with the locations where the absolute value of the second derivative function is larger than a predefined threshold value T7. It is noted that this technique not only works for "short and intense" artefacts having an amplitude larger than the gastric contraction peaks (e.g. X), but also works for "short and intense" artefacts that are smaller than the gastric contraction peaks (e.g. Y).

FIG. 19(*c*) shows the signal of FIG. 19(*a*) without the artefact, as can be obtained for example by replacing the values of the pressure signal of FIG. 19(*a*) by interpolated values for the pressure samples located at or near the "short and intense" artefact (e.g. in a 2.0 s time window centred around the location corresponding to the maximum of the second derivative). Interpolation offers the advantage of replacing a portion of the original pressure curve by a linear line segments, without introducing a local minimum or a local maximum.

The main advantage of removing such artefacts is that the signal of FIG. 19(*c*) becomes cleaner, and preferably only shows gastric contraction peaks, the amplitude of which and the duration of which can then be better assessed. It is noted that the removal of these artefacts in the specific example of FIG. 19 (which was taken from a healthy individual) would probably not have made a big difference for the detection of the Gastric Contraction Peaks (step 1302 of FIG. 13*a* to FIG. 13*d*) and the calculation of their duration (step 1303, 1353, 1383, 1373) and the calculation of the short term or long term motility values, but it can make an important difference for pressure signals obtained from ill patients, where the gastric contraction peaks are weak.

FIG. 20 shows an exemplary peak waveform as may be encountered in a raw pressure signal, and shows some characteristics of this peak which can be taken into account for evaluating whether this peak qualifies as a valid Gastric Contraction Peak, and which can be used in the calculation of the gastric activity value GAV, the short-term-gastric-motility Index STGBMI and the long term Gastric Balloon Motility Index LTGBMI, in particular the peak duration PD, and the peak height H.

FIG. 21 was already discussed above.

Figure 22:
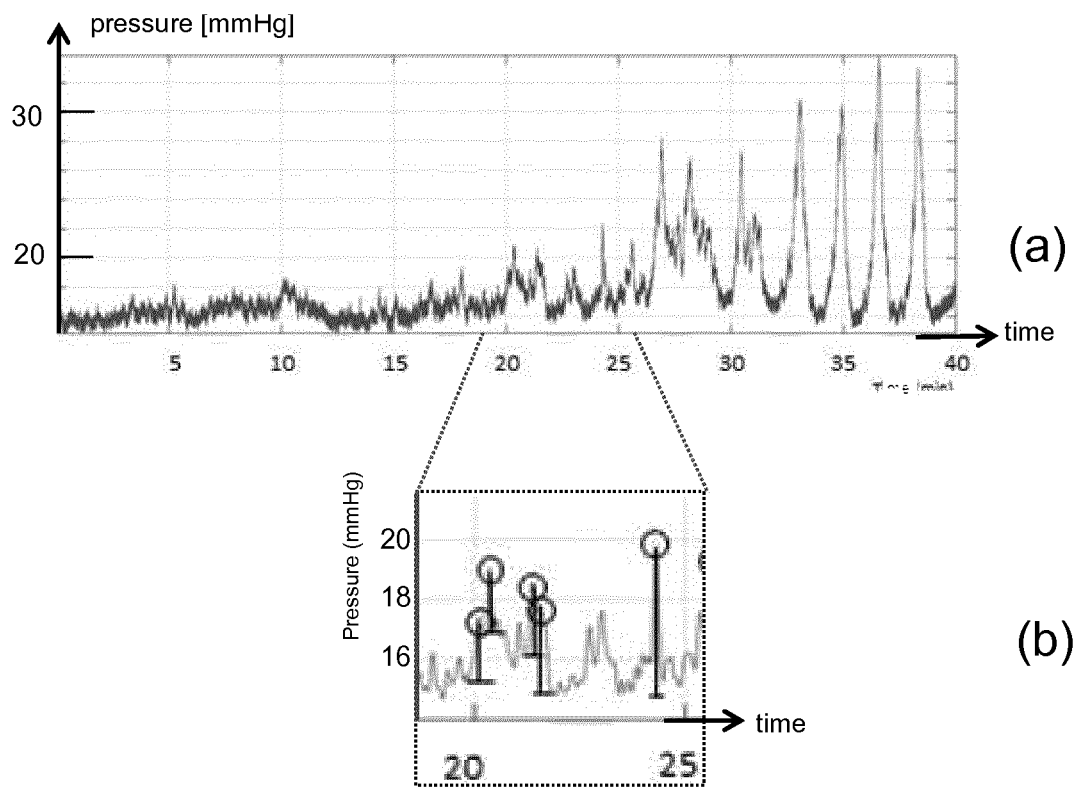
FIG. 22 shows another exemplary waveform (with relatively weak peaks) for which numerical values of the GAV and STGBMI are calculated according to the algorithm of FIG. 13a and FIG. 13c, for example to allow a comparison between these algorithms.

FIG. 22 shows a numerical example of how the GAV and STGBMI values can be calculated according to the algorithm of FIG. 13*a*, and FIG. 13*c*.

In the method of FIG. 13*a*, the GAV is equal to the gastric contraction peak duration GCPD. (see also step c1 of FIG. 13*d*). As described above, the Gastric Contraction Peak Duration "GCPD" can be defined as the time-difference ΔT between the start point and stop point of a Gastric Contraction Peak, which may coincide with local minima of the pressure curve. And the STGBMI is determined as a value indicative of a percentage of time during which gastric contraction peaks occur, measured in a first time-window TW1 having a predefined duration of 1 to 60 minutes, e.g. 2 to 55 minutes, or 1 to 45 minutes, or 15 to 45 minutes, or 1 to 30 minutes.

More specifically, the STGBMI can be calculated as the ratio of the sum or cumulative duration of the Gastric Contraction Peak Durations of valid Gastric Contraction Peaks over the duration of said first time-window TW1.

Reference is made to formula [1] described above, repeated here for convenience of the reader: $STGBMI = \Sigma_{TW1}(GCPD)/TW1$, where STGBMI is a short-term gastric balloon motility index (a value from 0% to 100%), TW1 is the first time window, and GCPD is the duration of the i-th Gastric Contraction Peak Duration inside the first time window.

In the example of FIG. 22, the STGBMI-value for the time-slot of 5 minutes, between 20 and 25 minutes (indicated by the dotted rectangle) can be calculated as follows:

GCPD1=first peak duration=10 s,

GCPD2=second peak duration=12 s,

GCPD3=third peak duration=13 s,

GCPD4=fourth peak duration=10 s,

GCPD5=fifth peak duration=9 s, cumulative duration=(10+12+13+10+9) s=54 s

STGBMI=54 s/300 s=18%

In step 1313 of FIG. 13*a* the STGBMI may be calculated in consecutive (non-overlapping) time-windows, each having a duration of 5 minutes (=300 s), but the invention is not limited thereto, and another window duration in the range from 1 to 60 minutes can also be used, for example a window duration in the range from 2 to 55 min, or a window duration in the range from 1 to 30 minutes, e.g. equal to about 3 min, about 4 min, about 5 min, about 6 min, about 7 min, about 8 min, about 9 min, about 10 min, about 12 min, about 15 min, about 20 min, about 25 min, about 30 min, about 35 min, about 40 min, about 45 min, about 50 min.

In an embodiment, non-overlapping first time-windows of 15 minutes are used, and one new STGBMI-value is provided every 15 minutes.

In another embodiment, overlapping first time-windows are used. This would allow for example to provide one new STGBMI-value every 2 minutes, even if the first time-window itself has a duration of for example 5 minutes.

For completeness it is mentioned that also a "sliding window" may be used. This would e.g. allow to provide a new STGBMI-value every second, even if the time-window itself has a duration of for example 5 minutes.

In an embodiment, a graphical output with a bar diagram is provided, showing one bar every 10 minutes (6 per hour), or every 12 minutes (5 per hour) or every 15 minutes (4 per hour). In this case the first time-window preferably also has a duration of 10, 12 and 15 minutes respectively, although that is not absolutely necessary, and a longer or a shorter first time-window may also be used.

Using the same example of FIG. 22, according to the algorithm of FIG. 13*c* using the weighting function w(H) of FIG. 13*e*, the individual peaks for the time-slot of 5 minutes, between 20 and 25 minutes (in the dotted rectangle) would be assigned the following gastric activity values:

GAV1=GCPD1*w(*H*1)=(10 s)*weight of (17.5−15.4=2.1 mmHg)=10s*0.01=0.1s

GAV2=GCPD2*w(*H*2)=(12 s)*weight of (19.1−16.9=2.2 mmHg)=12s*0.02=0.24s

GAV3=GCPD3*w(*H*3)=(13 s)*weight of (18.7−16=2.7 mmHg)=13s*0.07=0.91s

GAV4=GCPD4*w(H4)=(10 s)*weight of (17.9–14.9=3.0 mmHg)=10s*0.09=0.9s

GAV5=GCPD5*w(H5)=(9 s)*weight of (19.8–14.7=5.1 mmHg)=9s*0.28=2.52s sum(GAV1 to GAV5)=(0.1+0.24+0.91+0.9+2.52)=4.67 seconds The STGBMI-value over this time-window can then be calculated using formulas [10] or [11] mentioned above, as: STGBMI=4.67 s/300 s=1.56%, which is much lower than 18% in this example, because the peaks in the example were very weak peaks.

In an embodiment, the STGBMI is calculated in consecutive time-windows, each having a duration of 5 minutes (=300 s), but the invention is not limited thereto, and another window duration in the range from 1 to 60 minutes can also be used, for example a window duration in the range from 2 to 55 min, or a window duration in the range from 1 to 30 minutes, e.g. equal to about 3 min, about 4 min, about 5 min, about 6 min, about 7 min, about 8 min, about 9 min, about 10 min, about 12 min, about 15 min, about 20 min, about 25 min, about 30 min, about 35 min, about 40 min, about 45 min, about 50 min.

In an embodiment, non-overlapping time-windows of 15 minutes are used, and one new STGBMI-value is provided every 15 minutes.

In another embodiment, overlapping time-windows are used. This would allow for example to provide one new STGBMI-value every 2 minutes, even if the time-window itself has a duration of for example 5 minutes.

For completeness it is mentioned that also a "sliding window" may be used. This would e.g. allow to provide a new STGBMI-value every second, even if the time-window itself has a duration of for example 5 minutes.

In an embodiment, a graphical output with a bar diagram is provided, showing one bar every 10 minutes (6 per hour), or every 12 minutes (5 per hour) or every 15 minutes (4 per hour). In this case the time-window preferably also has a duration of 10, 12 and 15 minutes respectively, although that his not absolutely necessary, and a longer or a shorter time-window may also be used FIG. 23(a) shows an example of a raw pressure signal as can be obtained by a system according to an embodiment of the present invention. This pressure signal has a duration of about 6 hours, and was sampled at a frequency of 10 Hz.

FIG. 23(b) shows an enlarged portion thereof, with an indication of an MMC Phase I, Phase II and Phase III. As can be appreciated, it would be very difficult for a doctor to interpret the raw pressure curve, and the interpretation would be very subjective. The present invention solves that problem by providing (and optionally displaying) an objective value which is easy to interpret. This value has a high correlation with the degree of a good working stomach, and can be used to automatically adjust enteral feeding.

Figure 24:
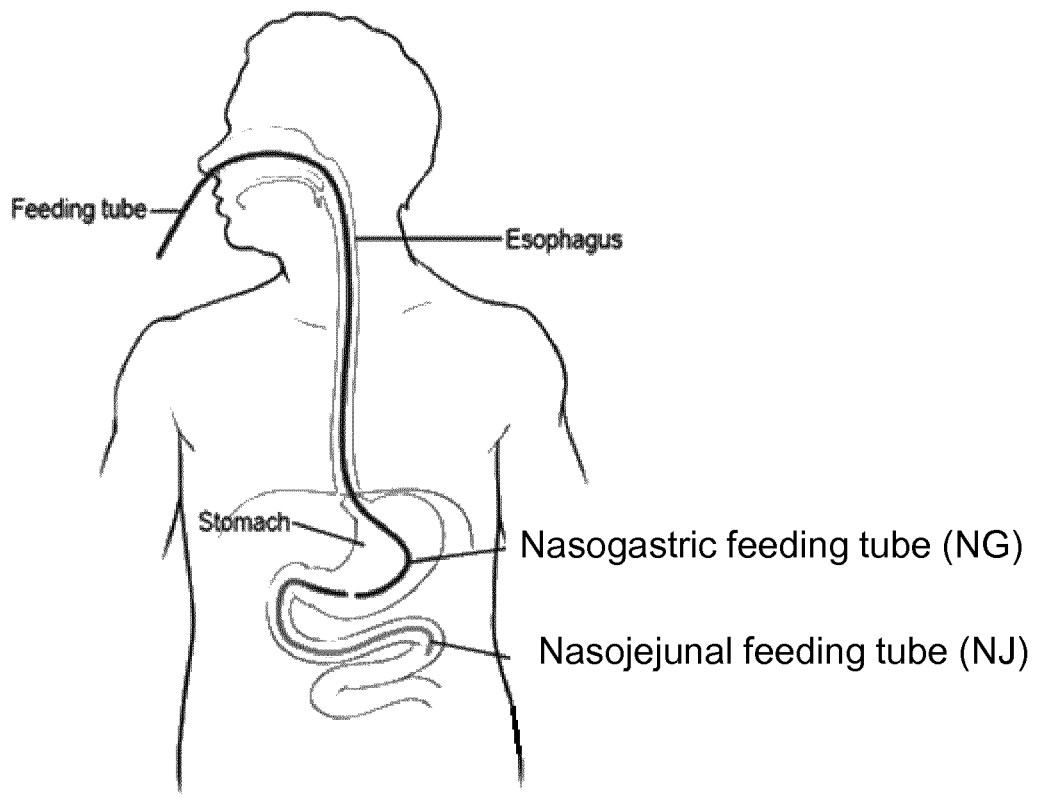
FIG. 24 shows an example of a nasogastric feeding tube, and a nasojejunal feeding tube, known in the art.

FIG. 24 shows an example of a nasogastric feeding tube, and a nasojejunal feeding tube, known in the art.

The invention claimed is:

1. A system for monitoring gastric motility and for artificially feeding a patient, the system comprising or connectable to a balloon catheter, the balloon catheter comprising an inflatable balloon, a first lumen in fluid connection with the inflatable balloon, and a second lumen for providing food to the patient, the second lumen having at least one second opening located outside the balloon, the system comprising:
 a pressure sensor fluidly connected or connectable to the first lumen for measuring a pressure of a fluid inside the at least one balloon;
 a food pump fluidly connected or connectable to the second lumen, and adapted for providing food;
 a controller operatively connected to the pressure sensor for obtaining the measured pressure values, and operatively connected to the food pump for driving the food pump so as to provide food at a configurable flow rate;
wherein the controller contains computer executable instructions comprising:
 first code fragments for performing a first algorithm for extracting gastric motility information from the measured pressure values, and
 second code fragments for performing a second algorithm for dynamically adjusting the flow rate of the food pump based on the extracted gastric motility information;
wherein the first algorithm is adapted for:
 (a) filtering the raw pressure signal to reduce or preferably completely remove influences other than gastric motility-induced pressure changes;
 (b) finding gastric contraction peaks in the filtered pressure signal;
 (c) determining a duration and/or a height of the gastric contraction peaks, and assigning a gastric activity value to each gastric contraction peak indicative of gastric activity based on the duration and/or the height;
 (d) optionally determining a short-term-gastric-motility value by calculating a sum of a plurality of the gastric activity values normalized over a first time window of 1 to 60 minutes, or by calculating a statistical value of a plurality of the gastric activity values over the first time window;
 (e) determining a long-term-gastric-motility-value as a maximum over a second time window of 1 hours to 3 hours of the gastric activity values or as a maximum of the short-term-gastric-motility values; and
wherein the second algorithm is adapted for:
 (f) comparing the long-term gastric motility value with at least one threshold, and if the long-term gastric motility value is lower than the at least one threshold, to reduce the flow-rate or to set the flow-rate to zero, and if the long-term gastric motility value is higher than the at least one threshold, to maintain or to increase the flow rate.

2. The system according to claim 1, wherein step (c) to step (e) perform one of options (i) to (iv):
 (i) wherein:
  step (c) comprises determining a duration of the gastric contraction peaks, and assigning a value equal to the duration as the gastric activity value; and
  step (d) comprises determining short-term-gastric-motility values by calculating a sum of a plurality of the gastric activity values normalized over the first time window; and
  step (e) comprises determining the long-term-gastric-motility-value as a maximum of the short-term-gastric-motility-values; or
 (ii) wherein:
  step (c) comprises determining a height of the gastric contraction peaks, and assigning a value in the range from 0.0 to 1.0 as a weight function of the height as the gastric activity value; and
  step (d) optionally comprises: determining a short-term-gastric-motility value by calculating a statistical value of a plurality of the gastric activity values over the first time window; and step (e) comprises determining the long-term-gastric-motility-value as a maximum of the gastric activity values; or (iii) wherein:
step (c) comprises determining a height of the gastric contraction peaks, and assigning a value in the range from 0.0 to 1.0 as a weight function of the height as the gastric activity value; and step (d) comprises: determining a short-term-gastric-motility value by calculating a statistical value of a plurality of the gastric activity values over the first time window; and step (e) comprises determining the long-term-gastric-motility-value as a maximum of the short-term-gastric-motility values; or (iv) wherein:
step (c) comprises determining a duration and a height of the gastric contraction peaks, and assigning a fraction of the duration using a weight function of the height as the gastric activity value; and step (d) comprises determining short-term-gastric-motility values by calculating a sum of a plurality of the gastric activity values normalized over the first time window; and step (e) comprises determining the long-term-gastric-motility-value as a maximum of the short-term-gastric-motility values.

3. The system according to claim 1, wherein step (a) comprises filtering the raw pressure signal to reduce or preferably completely remove pressure changes related to one or more of breathing, heart beats, gagging, coughing, sneezing, and hiccups.

4. The system according to claim 1, wherein step (b) comprises:
(b1) finding start points and stop points of candidate gastric contraction peaks;
(b2) determining at least one characteristic of the waveform of each candidate gastric contraction peak;
(b3) testing whether the at least one characteristic satisfies a predetermined condition, and:
  if an outcome of this test is true, considering this candidate gastric contraction peak as a valid gastric contraction peak or considering this candidate gastric contraction peak as a preliminary gastric contraction peak, and
  if the outcome of the test is false, discarding this candidate gastric contraction peak by not taking its duration and/or its height into account in the calculation of the gastric activity value, the optional short-term-gastric-motility value, and the long-term gastric motility value.

5. The system according to claim 4, wherein:
step (b1) comprises finding local minima of the filtered pressure signal and considering each waveform between consecutive local minima as a candidate gastric contraction peak;
step (c) comprises considering the time between these minima as the peak duration;
step (b2) comprises finding a minimum pressure and finding a maximum pressure of the candidate gastric contraction peak between the local minima and considering a difference between the maximum pressure and the minimum pressure as the height of the candidate gastric contraction peak;
step (b3) comprises testing whether the height of the candidate gastric contraction peak is larger than a given height value, and testing whether the peak duration is a value in a predefined range.

6. The system according to claim 4, wherein:
step (b1) comprises finding a start point at a crossing of a rising edge of the filtered pressure signal and a given height value, and finding a stop point at a crossing of a falling edge of the filtered pressure signal and the given height value, and considering each waveform between the start point and the stop point as a candidate gastric contraction peak, and considering the time between the start point and the stop point as the peak duration;
step (b2) comprises finding a minimum pressure and finding a maximum pressure of the candidate gastric contraction peak between the start point and the stop point, and considering a difference between the maximum pressure and the minimum pressure as the height of the candidate gastric contraction peak; and
step (b3) comprises testing whether the peak duration is a value in a predefined range.

7. The system according to claim 4, wherein:
step (b3) comprises: testing whether the at least one characteristic satisfies a predetermined condition or set of predetermined conditions, and if an outcome of this test is true, considering this candidate gastric contraction peak as a preliminary gastric contraction peak; and
the algorithm further comprises step (b4) of testing whether recently considered preliminary gastric contraction peaks satisfy a predetermined condition or set of predetermined conditions, and if an outcome of this test is true, to consider at least some of the recently considered preliminary gastric contraction peaks as valid gastric contraction peaks, and if the outcome of this test is false, to consider at least one of the recently considered preliminary gastric contraction peaks as invalid.

8. The system according to claim 4, wherein:
step (b2) further comprises determining a first slope as the maximum slope of the rising edge of the candidate gastric peak; and
step (b3) further comprises testing whether the first slope is smaller or larger than a predefined value, and if the first slope is larger than the predefined value, discarding the candidate gastric contraction peak.

9. The system according to claim 4, wherein:
step (b2) further comprises determining a second slope as the minimum slope of the falling edge of the candidate gastric contraction peak; and
step (b3) further comprises testing whether an absolute value of the second slope is smaller or larger than a predefined value, and if the absolute value of the second slope is larger than the predefined value, discarding the candidate gastric contraction peak.

10. The system according to claim 5, wherein:
the first algorithm further comprises a step of determining a pressure amplitude related to breathing; and
the given height value is dynamically calculated as a function of this pressure amplitude related to breathing.

11. The system according to claim 1, wherein:
the system further comprises output means for displaying at least the long-term gastric motility information and/or values derived herefrom, and optionally also the short-term-gastric-motility information and/or values derived herefrom; and the computer executable instructions further comprise third code fragments for presenting the gastric motility information on the output means, for example as graphical objects.

12. The system according to claim 1, further comprising input means for receiving settings and/or commands to drive the food pump, wherein the computer executable instructions further comprise fourth code fragments for receiving the settings and/or commands from the input means.

13. The system according to claim 1, wherein step (e) comprises:
testing whether the long term gastric motility value is larger than or optionally equal to a predefined threshold value; and
if an outcome of this test is true, maintaining the current flow rate; and
if an outcome of this test is false, reducing the current flow rate.

14. The system according to claim 1, wherein step (e) comprises:
testing in a first test whether the long term gastric motility value is larger than or optionally equal to a first predefined threshold value; and
if an outcome of this first test is true, maintaining the current flow rate, and
if an outcome of this first test is false, continuing as follows:
testing in a second test whether the long term gastric motility value is larger than or optionally equal to a second predefined threshold value; and
if an outcome of this second test is true, reducing the current flow rate; and
if an outcome of this second test is false, setting the flow rate to zero.

15. The system according to claim 1, wherein step (e) comprises:
testing in a first test whether the long term gastric motility value is larger than or optionally equal to a first predefined threshold value; and
if an outcome of this first test is true, increasing the current flow rate; and
if an outcome of this first test is false, continuing as follows:
testing in a second test whether the long term gastric motility value is larger than or optionally equal to a second predefined threshold value; and
if an outcome of this second test is true, maintaining the current flow rate; and
if an outcome of this second test is false, continuing as follows:
testing in a third test whether the long term gastric motility value is larger than or optionally equal to a third predefined threshold value; and
if an outcome of this third test is true, reducing the current flow rate; and
if an outcome of this third test is false, setting the flow rate to zero.

16. The system according to claim 1, further comprising an air pump fluidly connected or connectable to the first port, wherein the controller is operatively connected to the air pump and is further adapted for driving the air pump for inflating the at least one balloon and/or for deflating the balloon.

17. The system according to claim 1, wherein:
the balloon catheter further comprises a second balloon fluidly connected to a third lumen having at least a third opening located inside the second balloon, the second balloon being separately inflatable from the first balloon, and being located at a distal position of the balloon catheter;
the system further comprises a third port connectable to the third lumen of the balloon catheter, and further comprises a second pressure sensor fluidly connectable to the third port for measuring a pressure of a fluid inside the second balloon;
the controller is operatively connected to the second pressure sensor and further adapted for obtaining the measured pressure values related to the second balloon;
the first algorithm is further adapted for determining a direction of the gastric contractions as being towards or away from the small intestine; and
the flow rate is set at zero in the second algorithm if the determined direction of the gastric contractions is away from the small intestine.

18. The system according to claim 1, wherein:
the balloon catheter further comprises a fourth lumen having at least a fourth opening located at a distal end of the balloon catheter outside the first balloon and if present also outside the second balloon, for providing food directly into a small intestine;
the system further comprises a fourth port connected or connectable to the fourth lumen of the balloon catheter;
the system further comprises at least one valve operatively connected between the food pump and the second port and the fourth port for selectively providing food into the stomach via the second port or into the small intestine via the fourth port; and
the second algorithm is further adapted for dynamically adjusting a position of the valve for providing food via the fourth port if the long term gastric motility information is lower than a predefined threshold; and for maintaining the position of the valve otherwise.

19. The system according to claim 1, further comprising a memory and/or a storage device operatively connected to the controller, and wherein the controller further contains fifth code fragments for storing in the memory and/or in the storage device one or more of the following: the raw pressure values, the location and/or duration and/or height of the gastric contraction peaks, the amplitude of the breathing signal, the gastric activity values, the short-term-gastric-motility-values, and the long-term gastric motility values.

20. A computer program product as can be used in a system according to claim 1, the computer program product comprising at least the first code fragments and the second code fragments.

* * * * *